United States Patent
Ferrera et al.

(10) Patent No.: US 11,337,714 B2
(45) Date of Patent: May 24, 2022

(54) RESTORING BLOOD FLOW AND CLOT REMOVAL DURING ACUTE ISCHEMIC STROKE

(71) Applicant: Covidien LP, Mansfield, MA (US)

(72) Inventors: David Ferrera, Redondo Beach, CA (US); Andrew Cragg, Edina, MN (US); John Fulkerson, San Clemente, CA (US)

(73) Assignee: COVIDIEN LP, Mansfield, MA (US)

( * ) Notice: Subject to any disclaimer, the term of this patent is extended or adjusted under 35 U.S.C. 154(b) by 300 days.

(21) Appl. No.: 16/561,915

(22) Filed: Sep. 5, 2019

(65) Prior Publication Data

US 2019/0388108 A1 Dec. 26, 2019

Related U.S. Application Data

(63) Continuation of application No. 14/611,564, filed on Feb. 2, 2015, now Pat. No. 10,413,310, which is a
(Continued)

(51) Int. Cl.
*A61B 17/221* (2006.01)
*A61M 25/09* (2006.01)
(Continued)

(52) U.S. Cl.
CPC .......... *A61B 17/221* (2013.01); *A61F 2/013* (2013.01); *A61M 25/09* (2013.01);
(Continued)

(58) Field of Classification Search
CPC .......... A61B 17/221; A61B 2017/2212; A61B 2017/2215; A61B 2017/2217; A61M 25/09; A61M 25/09025; A61F 2/013
See application file for complete search history.

(56) References Cited

U.S. PATENT DOCUMENTS 3,174,851 A 3/1965 Buehler et al.
3,351,463 A 11/1967 Rozner et al.
(Continued)

FOREIGN PATENT DOCUMENTS

BR 9604566 A 9/1998
CN 101061970 A 10/2007
(Continued)

OTHER PUBLICATIONS

"Penumbra, Inc. Emolls First Patients in PULSE Clinical Trial to Evaluate a Fully Retrievable, Dense Mesh Temporary Stent for Immediate Flow Restoration in Interventional Acute Ischemic Stroke Treatment," Business Wire, Nov. 1, 2010, downloaded at http://www.businesswire.com/news/home/20101101006991/en/Penumbra-Emolls--Patients-PULSE-Clinical-Trial-Evaluate.
(Continued)

*Primary Examiner* — Tuan V Nguyen
(74) *Attorney, Agent, or Firm* — Fortem IP LLP; Mary Fox

(57) ABSTRACT

Devices for restoring blood flow to facilitate lysis of clots and/or enable capture of clots are disclosed. The devices can be configured to be disposed within a lumen of a microcatheter that is inserted within neurovasculature above a carotid siphon to a location of a clot. The devices can include an elongate pusher member and a self-expandable capturing member coupled to a distal end of the elongate pusher member. The capturing member can comprise a generally cylindrical body having an cell structure that is configured to compress the clot against an inner wall of the neurovasculature and capture the clot at least partially on a surface of the generally cylindrical body upon deployment of the capturing member from the microcatheter, thereby restoring blood flow to the neurovasculature downstream of the clot.

17 Claims, 51 Drawing Sheets

Related U.S. Application Data continuation of application No. 13/341,186, filed on Dec. 30, 2011, now Pat. No. 8,945,172, which is a continuation of application No. 12/475,389, filed on May 29, 2009, now Pat. No. 8,088,140, which is a continuation-in-part of application No. 12/422,105, filed on Apr. 10, 2009, now Pat. No. 8,545,514, and a continuation-in-part of application No. 12/182,370, filed on Jul. 30, 2008, now Pat. No. 9,220,522, and a continuation-in-part of application No. 12/123,390, filed on May 19, 2008, now Pat. No. 9,198,687, said application No. 13/341,186 is a continuation-in-part of application No. 12/123,390, filed on May 19, 2008, now Pat. No. 9,198,687.

(60) Provisional application No. 61/166,725, filed on Apr. 4, 2009, provisional application No. 61/057,613, filed on May 30, 2008, provisional application No. 61/044,392, filed on Apr. 11, 2008, provisional application No. 61/019,506, filed on Jan. 7, 2008, provisional application No. 61/015,154, filed on Dec. 19, 2007, provisional application No. 60/989,422, filed on Nov. 20, 2007, provisional application No. 60/987,384, filed on Nov. 12, 2007, provisional application No. 60/980,736, filed on Oct. 17, 2007.

(51) Int. Cl.
  *A61F 2/01*         (2006.01)
  *A61B 17/3207*      (2006.01)
  *A61B 17/22*        (2006.01)

(52) U.S. Cl.
  CPC ............... *A61M 25/09025* (2013.01); *A61B 17/320783* (2013.01); *A61B 2017/2212* (2013.01); *A61B 2017/22039* (2013.01); *A61B 2017/22094* (2013.01); *A61F 2002/016* (2013.01); *A61F 2230/0069* (2013.01); *A61F 2230/0076* (2013.01); *A61F 2230/0097* (2013.01)

(56) References Cited

U.S. PATENT DOCUMENTS

| | | | |
|---|---|---|---|
| 3,506,171 | A | 4/1970 | Rupert |
| 3,753,700 | A | 8/1973 | Harrison et al. |
| 3,998,938 | A | 12/1976 | Szegvari |
| 4,046,150 | A | 9/1977 | Schwartz et al. |
| 4,299,255 | A | 11/1981 | Miller |
| 4,347,846 | A | 9/1982 | Dormia |
| 4,403,612 | A | 9/1983 | Fogarty |
| 4,611,594 | A | 9/1986 | Grayhack et al. |
| 4,612,931 | A | 9/1986 | Dormia |
| 4,650,466 | A | 3/1987 | Luther |
| 4,655,771 | A | 4/1987 | Wallsten |
| 4,733,665 | A | 3/1988 | Palmaz |
| 4,739,762 | A | 4/1988 | Palmaz |
| 4,793,348 | A | 12/1988 | Palmaz |
| 4,890,611 | A | 1/1990 | Monfort et al. |
| 4,993,481 | A | 2/1991 | Kamimoto et al. |
| 4,998,539 | A | 3/1991 | Delsanti |
| 5,035,686 | A | 7/1991 | Crittenden et al. |
| 5,057,114 | A | 10/1991 | Wittich et al. |
| 5,071,407 | A | 12/1991 | Termin et al. |
| 5,100,423 | A | 3/1992 | Fearnot |
| 5,102,417 | A | 4/1992 | Palmaz |
| 5,190,058 | A | 3/1993 | Jones et al. |
| 5,192,286 | A | 3/1993 | Phan et al. |
| 5,195,984 | A | 3/1993 | Schatz |
| 5,197,978 | A | 3/1993 | Hess |
| 5,217,484 | A | 6/1993 | Marks |
| 5,222,964 | A | 6/1993 | Cooper |
| 5,222,971 | A | 6/1993 | Willard et al. |
| 5,275,622 | A | 1/1994 | Lazarus et al. |
| 5,327,885 | A | 7/1994 | Griffith |
| 5,330,482 | A | 7/1994 | Gibbs et al. |
| 5,344,395 | A | 9/1994 | Whalen et al. |
| 5,354,295 | A | 10/1994 | Guglielmi et al. |
| 5,370,653 | A | 12/1994 | Cragg |
| 5,411,549 | A | 5/1995 | Peters |
| 5,423,829 | A | 6/1995 | Pham et al. |
| 5,425,739 | A | 6/1995 | Jessen |
| 5,449,372 | A | 9/1995 | Schmaltz et al. |
| 5,456,667 | A | 10/1995 | Ham et al. |
| 5,490,859 | A | 2/1996 | Mische et al. |
| 5,496,330 | A | 3/1996 | Bates et al. |
| 5,501,694 | A | 3/1996 | Ressemann et al. |
| 5,527,282 | A | 6/1996 | Segal |
| 5,527,326 | A | 6/1996 | Hermann et al. |
| 5,540,680 | A | 7/1996 | Guglielmi et al. |
| 5,540,707 | A | 7/1996 | Ressemann et al. |
| 5,569,245 | A | 10/1996 | Guglielmi et al. |
| 5,571,122 | A | 11/1996 | Kelly et al. |
| 5,573,520 | A | 11/1996 | Schwartz et al. |
| 5,624,449 | A | 4/1997 | Pham et al. |
| 5,643,309 | A | 7/1997 | Myler et al. |
| 5,649,906 | A | 7/1997 | Gory et al. |
| 5,653,743 | A | 8/1997 | Martin |
| 5,669,933 | A | 9/1997 | Simon et al. |
| 5,681,336 | A | 10/1997 | Clement et al. |
| 5,683,449 | A | 11/1997 | Marcade |
| 5,690,667 | A | 11/1997 | Gia |
| 5,695,519 | A | 12/1997 | Summers et al. |
| 5,718,724 | A | 2/1998 | Goicoechea et al. |
| 5,720,764 | A | 2/1998 | Naderlinger |
| 5,743,905 | A | 4/1998 | Eder et al. |
| 5,749,883 | A | 5/1998 | Halpern |
| 5,759,192 | A | 6/1998 | Saunders |
| 5,769,882 | A | 6/1998 | Fogarty et al. |
| 5,792,145 | A | 8/1998 | Bates et al. |
| 5,792,157 | A | 8/1998 | Mische et al. |
| 5,795,322 | A | 8/1998 | Boudewijn |
| 5,800,454 | A | 9/1998 | Jacobsen et al. |
| 5,800,457 | A | 9/1998 | Gelbfish |
| 5,800,519 | A | 9/1998 | Sandock |
| 5,800,520 | A | 9/1998 | Fogarty et al. |
| 5,800,525 | A | 9/1998 | Bachinski et al. |
| 5,814,064 | A | 9/1998 | Daniel et al. |
| 5,824,037 | A | 10/1998 | Fogarty et al. |
| 5,827,304 | A | 10/1998 | Hart |
| 5,827,324 | A | 10/1998 | Cassell et al. |
| 5,836,868 | A | 11/1998 | Ressemann et al. |
| 5,848,964 | A | 12/1998 | Samuels |
| 5,851,206 | A | 12/1998 | Guglielmi et al. |
| 5,853,419 | A | 12/1998 | Imran |
| 5,855,578 | A | 1/1999 | Guglielmi et al. |
| 5,882,329 | A | 3/1999 | Patterson et al. |
| 5,888,201 | A | 3/1999 | Stinson et al. |
| 5,891,126 | A | 4/1999 | Osborn, III et al. |
| 5,895,398 | A | 4/1999 | Wensel et al. |
| 5,897,567 | A | 4/1999 | Ressemann et al. |
| 5,904,698 | A | 5/1999 | Thomas et al. |
| 5,911,717 | A | 6/1999 | Jacobsen et al. |
| 5,911,734 | A | 6/1999 | Tsugita et al. |
| 5,913,895 | A | 6/1999 | Burpee et al. |
| 5,916,235 | A | 6/1999 | Guglielmi |
| 5,919,187 | A | 7/1999 | Guglielmi et al. |
| 5,922,019 | A | 7/1999 | Hankh et al. |
| 5,925,037 | A | 7/1999 | Guglielmi et al. |
| 5,925,061 | A | 7/1999 | Ogi et al. |
| 5,928,226 | A | 7/1999 | Guglielmi et al. |
| 5,928,260 | A | 7/1999 | Chin et al. |
| 5,935,139 | A | 8/1999 | Bates |
| 5,938,671 | A | 8/1999 | Katoh et al. |
| 5,938,697 | A | 8/1999 | Killion et al. |
| 5,941,869 | A | 8/1999 | Patterson et al. |
| 5,941,895 | A | 8/1999 | Myler et al. |
| 5,944,714 | A | 8/1999 | Guglielmi et al. |
| 5,947,962 | A | 9/1999 | Guglielmi et al. |
| 5,947,995 | A | 9/1999 | Samuels |
| 5,948,016 | A | 9/1999 | Jang |

(56) References Cited

U.S. PATENT DOCUMENTS

| | | |
|---|---|---|
| 5,951,599 A | 9/1999 | Mccrory |
| 5,954,743 A | 9/1999 | Jang |
| 5,961,547 A | 10/1999 | Razavi |
| 5,964,797 A | 10/1999 | Ho |
| 5,968,013 A | 10/1999 | Smith et al. |
| 5,968,088 A | 10/1999 | Hansen et al. |
| 5,972,016 A | 10/1999 | Morales |
| 5,972,019 A | 10/1999 | Engelson et al. |
| 5,972,219 A | 10/1999 | Habets et al. |
| 5,976,120 A | 11/1999 | Chow et al. |
| 5,976,126 A | 11/1999 | Guglielmi |
| 5,976,131 A | 11/1999 | Guglielmi et al. |
| 5,980,514 A | 11/1999 | Kupiecki et al. |
| 5,984,929 A | 11/1999 | Bashiri et al. |
| 6,001,118 A | 12/1999 | Daniel et al. |
| 6,010,449 A | 1/2000 | Selmon et al. |
| 6,010,498 A | 1/2000 | Guglielmi |
| 6,010,521 A | 1/2000 | Lee et al. |
| 6,013,093 A | 1/2000 | Nott et al. |
| 6,015,424 A | 1/2000 | Rosenbluth et al. |
| 6,039,721 A | 3/2000 | Johnson et al. |
| 6,051,020 A | 4/2000 | Goicoechea et al. |
| 6,059,814 A | 5/2000 | Ladd |
| 6,063,070 A | 5/2000 | Eder |
| 6,063,100 A | 5/2000 | Diaz et al. |
| 6,063,104 A | 5/2000 | Villar et al. |
| 6,063,111 A | 5/2000 | Hieshima et al. |
| 6,066,149 A | 5/2000 | Samson et al. |
| 6,066,158 A | 5/2000 | Engelson et al. |
| 6,077,260 A | 6/2000 | Wheelock et al. |
| 6,083,220 A | 7/2000 | Guglielmi et al. |
| 6,093,199 A | 7/2000 | Brown et al. |
| 6,096,034 A | 8/2000 | Kupiecki et al. |
| 6,096,053 A | 8/2000 | Bates |
| 6,099,549 A | 8/2000 | Bosma et al. |
| 6,106,548 A | 8/2000 | Roubin et al. |
| 6,110,198 A | 8/2000 | Fogarty et al. |
| 6,117,167 A | 9/2000 | Goicoechea et al. |
| 6,118,001 A | 9/2000 | Owen et al. |
| 6,123,115 A | 9/2000 | Greenhalgh |
| 6,123,714 A | 9/2000 | Gia et al. |
| 6,129,755 A | 10/2000 | Mathis et al. |
| 6,138,006 A | 10/2000 | Foti |
| 6,146,396 A | 11/2000 | Konya et al. |
| 6,156,061 A | 12/2000 | Wallace et al. |
| 6,159,238 A | 12/2000 | Killion et al. |
| 6,159,239 A | 12/2000 | Greenhalgh |
| 6,164,339 A | 12/2000 | Greenhalgh |
| 6,165,178 A | 12/2000 | Bashiri et al. |
| 6,165,213 A | 12/2000 | Goicoechea et al. |
| 6,168,592 B1 | 1/2001 | Kupiecki et al. |
| 6,168,603 B1 | 1/2001 | Leslie et al. |
| 6,168,604 B1 | 1/2001 | Cano |
| 6,179,857 B1 | 1/2001 | Diaz et al. |
| 6,179,861 B1 | 1/2001 | Khosravi et al. |
| 6,187,017 B1 | 2/2001 | Gregory, Jr. |
| 6,190,358 B1 | 2/2001 | Fitzmaurice et al. |
| 6,190,394 B1 | 2/2001 | Lind et al. |
| 6,192,944 B1 | 2/2001 | Greenhalgh |
| 6,193,708 B1 | 2/2001 | Ken et al. |
| 6,193,745 B1 | 2/2001 | Fogarty et al. |
| 6,203,552 B1 | 3/2001 | Bagley et al. |
| 6,210,364 B1 | 4/2001 | Anderson et al. |
| 6,214,025 B1 | 4/2001 | Thistle et al. |
| 6,217,609 B1 | 4/2001 | Haverkost |
| 6,221,096 B1 | 4/2001 | Aiba et al. |
| 6,231,598 B1 | 5/2001 | Berry et al. |
| 6,238,412 B1 | 5/2001 | Dubrul et al. |
| 6,238,430 B1 | 5/2001 | Klumb et al. |
| 6,241,746 B1 | 6/2001 | Bosma et al. |
| 6,245,089 B1 | 6/2001 | Daniel et al. |
| 6,254,571 B1 | 7/2001 | Hart |
| 6,254,628 B1 | 7/2001 | Wallace et al. |
| 6,264,686 B1 | 7/2001 | Rieu et al. |
| 6,264,687 B1 | 7/2001 | Tomonto |
| 6,267,777 B1 | 7/2001 | Bosma et al. |
| 6,273,900 B1 | 8/2001 | Nott et al. |
| 6,277,125 B1 | 8/2001 | Barry et al. |
| 6,277,126 B1 | 8/2001 | Barry et al. |
| 6,280,413 B1 | 8/2001 | Clark et al. |
| 6,283,940 B1 | 9/2001 | Mulholland |
| 6,283,992 B1 | 9/2001 | Hankh et al. |
| 6,290,720 B1 | 9/2001 | Khosravi et al. |
| 6,302,906 B1 | 10/2001 | Goicoechea et al. |
| 6,305,436 B1 | 10/2001 | Andersen et al. |
| 6,306,141 B1 | 10/2001 | Jervis |
| 6,312,463 B1 | 11/2001 | Rourke et al. |
| 6,322,585 B1 | 11/2001 | Khosravi et al. |
| 6,325,815 B1 | 12/2001 | Kusleika et al. |
| 6,325,820 B1 | 12/2001 | Khosravi et al. |
| 6,325,822 B1 | 12/2001 | Chouinard et al. |
| 6,336,934 B1 | 1/2002 | Gilson et al. |
| 6,344,041 B1 | 2/2002 | Kupiecki et al. |
| 6,361,558 B1 | 3/2002 | Hieshima et al. |
| 6,371,969 B1 | 4/2002 | Tsugita et al. |
| 6,379,329 B1 | 4/2002 | Naglreiter et al. |
| 6,383,205 B1 | 5/2002 | Samson et al. |
| 6,390,993 B1 | 5/2002 | Cornish et al. |
| 6,402,771 B1 | 6/2002 | Palmer et al. |
| 6,409,721 B1 | 6/2002 | Wheelock et al. |
| 6,425,893 B1 | 7/2002 | Guglielmi |
| 6,425,914 B1 | 7/2002 | Wallace et al. |
| 6,428,558 B1 | 8/2002 | Jones et al. |
| 6,432,122 B1 | 8/2002 | Gilson et al. |
| 6,443,971 B1 | 9/2002 | Boylan et al. |
| 6,443,972 B1 | 9/2002 | Bosma et al. |
| 6,454,775 B1 | 9/2002 | Demarais et al. |
| 6,454,780 B1 | 9/2002 | Wallace |
| 6,458,139 B1 | 10/2002 | Palmer et al. |
| 6,468,266 B1 | 10/2002 | Bashiri et al. |
| 6,468,301 B1 | 10/2002 | Amplatz et al. |
| 6,475,236 B1 | 11/2002 | Roubin et al. |
| 6,485,500 B1 | 11/2002 | Kokish et al. |
| 6,491,719 B1 | 12/2002 | Fogarty et al. |
| 6,511,492 B1 | 1/2003 | Rosenbluth et al. |
| 6,514,273 B1 | 2/2003 | Voss et al. |
| 6,533,811 B1 | 3/2003 | Ryan et al. |
| 6,537,294 B1 | 3/2003 | Boyle et al. |
| 6,551,342 B1 | 4/2003 | Shen et al. |
| 6,554,849 B1 | 4/2003 | Jones et al. |
| 6,554,856 B1 | 4/2003 | Doorly et al. |
| 6,558,405 B1 | 5/2003 | Mcinnes |
| 6,562,066 B1 | 5/2003 | Martin |
| 6,569,193 B1 | 5/2003 | Cox et al. |
| 6,572,648 B1 | 6/2003 | Klumb et al. |
| 6,575,995 B1 | 6/2003 | Huter et al. |
| 6,575,997 B1 | 6/2003 | Palmer et al. |
| 6,589,265 B1 | 7/2003 | Palmer et al. |
| 6,592,607 B1 | 7/2003 | Palmer et al. |
| 6,592,615 B1 | 7/2003 | Marcade et al. |
| 6,610,077 B1 | 8/2003 | Hancock et al. |
| 6,616,617 B1 | 9/2003 | Ferrera et al. |
| 6,629,953 B1 | 10/2003 | Boyd |
| 6,632,241 B1 | 10/2003 | Hancock et al. |
| 6,635,081 B2 | 10/2003 | Khosravi et al. |
| 6,638,294 B1 | 10/2003 | Palmer |
| 6,641,590 B1 | 11/2003 | Palmer et al. |
| 6,645,224 B2 | 11/2003 | Gilson et al. |
| 6,652,505 B1 | 11/2003 | Tsugita |
| 6,652,548 B2 | 11/2003 | Evans et al. |
| 6,652,576 B1 | 11/2003 | Stalker |
| 6,656,214 B1 | 12/2003 | Fogarty et al. |
| 6,660,014 B2 | 12/2003 | Demarais et al. |
| 6,660,021 B1 | 12/2003 | Palmer et al. |
| 6,663,607 B2 | 12/2003 | Slaikeu et al. |
| 6,663,650 B2 | 12/2003 | Sepetka et al. |
| 6,666,829 B2 | 12/2003 | Cornish et al. |
| 6,669,723 B2 | 12/2003 | Killion et al. |
| 6,673,025 B1 | 1/2004 | Richardson et al. |
| 6,673,106 B2 | 1/2004 | Mitelberg et al. |
| 6,679,893 B1 | 1/2004 | Tran |
| 6,685,722 B1 | 2/2004 | Rosenbluth et al. |
| 6,685,738 B2 | 2/2004 | Chouinard et al. |
| 6,692,508 B2 | 2/2004 | Wensel et al. |

(56) References Cited

U.S. PATENT DOCUMENTS

| | | |
|---|---|---|
| 6,695,813 B1 | 2/2004 | Boyle et al. |
| 6,702,782 B2 | 3/2004 | Miller et al. |
| 6,702,843 B1 | 3/2004 | Brown et al. |
| 6,709,440 B2 | 3/2004 | Callol et al. |
| 6,716,178 B1 | 4/2004 | Kilpatrick et al. |
| 6,716,238 B2 | 4/2004 | Elliott |
| 6,723,108 B1 | 4/2004 | Jones et al. |
| 6,723,112 B2 | 4/2004 | Ho et al. |
| 6,730,104 B1 | 5/2004 | Sepetka et al. |
| 6,733,519 B2 | 5/2004 | Lashinski et al. |
| 6,743,236 B2 | 6/2004 | Barry et al. |
| 6,746,468 B1 | 6/2004 | Sepetka et al. |
| 6,764,506 B2 | 7/2004 | Roubin et al. |
| 6,773,454 B2 | 8/2004 | Wholey et al. |
| 6,790,237 B2 | 9/2004 | Stinson |
| 6,795,979 B2 | 9/2004 | Fournier |
| 6,802,851 B2 | 10/2004 | Jones et al. |
| 6,811,560 B2 | 11/2004 | Jones et al. |
| 6,818,013 B2 | 11/2004 | Mitelberg et al. |
| 6,818,015 B2 | 11/2004 | Hankh et al. |
| 6,821,291 B2 | 11/2004 | Bolea et al. |
| 6,824,558 B2 | 11/2004 | Parodi |
| 6,833,002 B2 | 12/2004 | Stack et al. |
| 6,833,003 B2 | 12/2004 | Jones et al. |
| 6,840,958 B2 | 1/2005 | Nunez et al. |
| 6,878,151 B2 | 4/2005 | Carrison et al. |
| 6,881,220 B2 | 4/2005 | Edwin et al. |
| 6,887,268 B2 | 5/2005 | Butaric et al. |
| 6,893,413 B2 | 5/2005 | Martin |
| 6,913,612 B2 | 7/2005 | Palmer et al. |
| 6,921,414 B2 | 7/2005 | Klumb et al. |
| 6,945,977 B2 | 9/2005 | Demarais et al. |
| 6,949,620 B2 | 9/2005 | Aida et al. |
| 6,953,468 B2 | 10/2005 | Jones et al. |
| 6,953,472 B2 | 10/2005 | Palmer et al. |
| 6,955,685 B2 | 10/2005 | Escamilla et al. |
| 6,960,228 B2 | 11/2005 | Mitelberg et al. |
| 6,963,227 B2 | 11/2005 | Murakami et al. |
| 6,974,473 B2 | 12/2005 | Barclay et al. |
| 6,989,020 B2 | 1/2006 | Jones et al. |
| 6,991,841 B2 | 1/2006 | Cowelchuk et al. |
| 6,994,723 B1 | 2/2006 | Mcmahon |
| 7,001,422 B2 | 2/2006 | Escamilla et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,018,401 B1 | 3/2006 | Hyodoh et al. |
| 7,029,688 B2 | 4/2006 | Hubbell et al. |
| 7,037,329 B2 | 5/2006 | Martin |
| 7,037,331 B2 | 5/2006 | Mitelberg et al. |
| 7,041,116 B2 | 5/2006 | Goto et al. |
| 7,048,014 B2 | 5/2006 | Hyodoh et al. |
| 7,052,500 B2 | 5/2006 | Bashiri et al. |
| 7,056,328 B2 | 6/2006 | Arnott |
| 7,056,336 B2 | 6/2006 | Armstrong et al. |
| 7,058,456 B2 | 6/2006 | Pierce |
| 7,060,091 B2 | 6/2006 | Killion et al. |
| 7,089,218 B1 | 8/2006 | Visel |
| 7,097,653 B2 | 8/2006 | Freudenthal et al. |
| 7,101,380 B2 | 9/2006 | Khachin et al. |
| 7,112,217 B1 | 9/2006 | Kugler et al. |
| 7,118,600 B2 | 10/2006 | Dua et al. |
| 7,125,419 B2 | 10/2006 | Sequin et al. |
| 7,128,073 B1 | 10/2006 | Van Der Burg et al. |
| 7,128,736 B1 | 10/2006 | Abrams et al. |
| 7,144,421 B2 | 12/2006 | Carpenter et al. |
| 7,147,655 B2 | 12/2006 | Chermoni |
| 7,147,659 B2 | 12/2006 | Jones |
| 7,147,660 B2 | 12/2006 | Chobotov et al. |
| 7,156,869 B1 | 1/2007 | Pacetti |
| 7,156,871 B2 | 1/2007 | Jones et al. |
| 7,160,317 B2 | 1/2007 | McHale et al. |
| 7,169,165 B2 | 1/2007 | Belef et al. |
| 7,172,575 B2 | 2/2007 | El-Nounou et al. |
| 7,172,617 B2 | 2/2007 | Colgan et al. |
| 7,175,607 B2 | 2/2007 | Lim et al. |
| 7,179,273 B1 | 2/2007 | Palmer et al. |
| 7,179,276 B2 | 2/2007 | Barry et al. |
| 7,179,284 B2 | 2/2007 | Khosravi et al. |
| 7,182,774 B2 | 2/2007 | Barry et al. |
| 7,195,648 B2 | 3/2007 | Jones et al. |
| 7,201,769 B2 | 4/2007 | Jones et al. |
| 7,201,770 B2 | 4/2007 | Johnson et al. |
| 7,223,284 B2 | 5/2007 | Khosravi et al. |
| 7,232,432 B2 | 6/2007 | Fulton, III et al. |
| 7,238,197 B2 | 7/2007 | Sequin et al. |
| 7,240,516 B2 | 7/2007 | Pryor |
| 7,241,301 B2 | 7/2007 | Thramann et al. |
| 7,264,628 B2 | 9/2007 | Jones et al. |
| 7,270,674 B2 | 9/2007 | Jones et al. |
| 7,279,003 B2 | 10/2007 | Berra et al. |
| 7,279,292 B2 | 10/2007 | Imam et al. |
| 7,285,126 B2 | 10/2007 | Sepetka et al. |
| 7,294,123 B2 | 11/2007 | Jones et al. |
| 7,294,147 B2 | 11/2007 | Hartley |
| 7,300,458 B2 | 11/2007 | Henkes et al. |
| 7,303,572 B2 | 12/2007 | Melsheimer et al. |
| 7,306,619 B1 | 12/2007 | Palmer |
| 7,306,622 B2 | 12/2007 | Jones et al. |
| 7,309,345 B2 | 12/2007 | Wallace |
| 7,309,351 B2 | 12/2007 | Escamilla et al. |
| 7,311,726 B2 | 12/2007 | Mitelberg et al. |
| 7,323,000 B2 | 1/2008 | Monstdt et al. |
| 7,323,005 B2 | 1/2008 | Wallace et al. |
| 7,323,006 B2 | 1/2008 | Andreas et al. |
| 7,326,240 B1 | 2/2008 | Caro et al. |
| 7,344,550 B2 | 3/2008 | Carrison et al. |
| 7,344,556 B2 | 3/2008 | Seguin et al. |
| 7,344,558 B2 | 3/2008 | Lorenzo et al. |
| 7,351,255 B2 | 4/2008 | Andreas |
| 7,354,455 B2 | 4/2008 | Stinson |
| 7,357,809 B2 | 4/2008 | Jones et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,402,169 B2 | 7/2008 | Killion et al. |
| 7,407,509 B2 | 8/2008 | Greenberg et al. |
| 7,435,254 B2 | 10/2008 | Chouinard et al. |
| 7,438,720 B2 | 10/2008 | Shaked |
| 7,455,646 B2 | 11/2008 | Richardson et al. |
| 7,473,272 B2 | 1/2009 | Pryor |
| 7,481,821 B2 | 1/2009 | Fogarty et al. |
| 7,485,122 B2 | 2/2009 | Teoh |
| 7,494,474 B2 | 2/2009 | Richardson et al. |
| 7,510,565 B2 | 3/2009 | Gilson et al. |
| 7,517,352 B2 | 4/2009 | Evans et al. |
| 7,524,319 B2 | 4/2009 | Dubrul |
| 7,534,252 B2 | 5/2009 | Sepetka et al. |
| 7,549,974 B2 | 6/2009 | Nayak |
| 7,553,314 B2 | 6/2009 | Khachin et al. |
| 7,553,321 B2 | 6/2009 | Litzenberg et al. |
| 7,582,101 B2 | 9/2009 | Jones et al. |
| 7,618,434 B2 | 11/2009 | Santra et al. |
| 7,640,952 B2 | 1/2010 | Khachin et al. |
| 7,691,122 B2 | 4/2010 | Dieck et al. |
| 7,727,242 B2 | 6/2010 | Sepetka et al. |
| 7,727,243 B2 | 6/2010 | Sepetka et al. |
| 7,749,243 B2 | 7/2010 | Phung et al. |
| 7,780,694 B2 | 8/2010 | Palmer et al. |
| 7,833,240 B2 | 11/2010 | Okushi et al. |
| 7,972,342 B2 | 7/2011 | Gandhi et al. |
| 7,976,560 B2 | 7/2011 | Denison et al. |
| 8,052,640 B2 | 11/2011 | Fiorella et al. |
| 8,062,307 B2 | 11/2011 | Sepetka et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,918 B2 | 1/2012 | Gandhi et al. |
| 8,100,935 B2 | 1/2012 | Rosenbluth et al. |
| 8,105,333 B2 | 1/2012 | Sepetka et al. |
| 8,197,493 B2 | 6/2012 | Ferrera et al. |
| 8,357,179 B2 | 1/2013 | Grandfield et al. |
| 8,425,549 B2 | 4/2013 | Lenker et al. |

(56) References Cited

U.S. PATENT DOCUMENTS

| | | |
|---|---|---|
| 8,589,230 B1 | 11/2013 | Bickerstaff |
| 8,603,014 B2 | 12/2013 | Alleman et al. |
| 8,679,142 B2 | 3/2014 | Slee et al. |
| 8,837,800 B1 | 9/2014 | Bammer et al. |
| 8,940,003 B2 | 1/2015 | Slee et al. |
| 9,078,682 B2 | 7/2015 | Lenker et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0000797 A1 | 5/2001 | Mazzocchi |
| 2001/0003801 A1 | 6/2001 | Strecker |
| 2001/0004705 A1 | 6/2001 | Killion et al. |
| 2001/0010013 A1 | 7/2001 | Cox et al. |
| 2001/0031981 A1 | 10/2001 | Evans et al. |
| 2001/0034531 A1 | 10/2001 | Ho et al. |
| 2001/0041899 A1 | 11/2001 | Foster |
| 2001/0044633 A1 | 11/2001 | Klint |
| 2001/0044647 A1 | 11/2001 | Pinchuk et al. |
| 2001/0044649 A1 | 11/2001 | Vallana et al. |
| 2001/0047202 A1 | 11/2001 | Slaikeu et al. |
| 2001/0051823 A1 | 12/2001 | Khosravi et al. |
| 2001/0053929 A1 | 12/2001 | Vonesh et al. |
| 2002/0004536 A1 | 1/2002 | Keller |
| 2002/0004681 A1 | 1/2002 | Teoh et al. |
| 2002/0007210 A1 | 1/2002 | Chouinard et al. |
| 2002/0016584 A1 | 2/2002 | Wise et al. |
| 2002/0016624 A1 | 2/2002 | Patterson et al. |
| 2002/0032479 A1 | 3/2002 | Hankh et al. |
| 2002/0038142 A1 | 3/2002 | Khosravi et al. |
| 2002/0038146 A1 | 3/2002 | Harry |
| 2002/0052643 A1 | 5/2002 | Wholey et al. |
| 2002/0068968 A1 | 6/2002 | Hupp |
| 2002/0072790 A1 | 6/2002 | Mcguckin et al. |
| 2002/0087209 A1 | 7/2002 | Edwin et al. |
| 2002/0091355 A1 | 7/2002 | Hayden |
| 2002/0095141 A1 | 7/2002 | Belef et al. |
| 2002/0143387 A1 | 10/2002 | Soetikno et al. |
| 2002/0161377 A1 | 10/2002 | Rabkin |
| 2002/0169458 A1 | 11/2002 | Connors |
| 2002/0183831 A1 | 12/2002 | Rolando et al. |
| 2002/0193868 A1 | 12/2002 | Mitelberg et al. |
| 2002/0198588 A1 | 12/2002 | Armstrong et al. |
| 2003/0023230 A1 | 1/2003 | Lewis et al. |
| 2003/0023299 A1 | 1/2003 | Amplatz et al. |
| 2003/0032941 A1 | 2/2003 | Boyle et al. |
| 2003/0032977 A1 | 2/2003 | Brady |
| 2003/0040705 A1 | 2/2003 | Dorros et al. |
| 2003/0040771 A1 | 2/2003 | Hyodoh et al. |
| 2003/0040772 A1 | 2/2003 | Hyodoh et al. |
| 2003/0055440 A1 | 3/2003 | Jones et al. |
| 2003/0055451 A1 | 3/2003 | Jones et al. |
| 2003/0060782 A1 | 3/2003 | Bose et al. |
| 2003/0074056 A1 | 4/2003 | Killion et al. |
| 2003/0078605 A1 | 4/2003 | Bashiri et al. |
| 2003/0097114 A1 | 5/2003 | Ouriel et al. |
| 2003/0105484 A1 | 6/2003 | Boyle et al. |
| 2003/0125791 A1 | 7/2003 | Sequin et al. |
| 2003/0125798 A1 | 7/2003 | Martin |
| 2003/0130719 A1 | 7/2003 | Martin |
| 2003/0139796 A1 | 7/2003 | Sequin et al. |
| 2003/0139803 A1 | 7/2003 | Sequin et al. |
| 2003/0149475 A1 | 8/2003 | Hyodoh et al. |
| 2003/0153944 A1 | 8/2003 | Phung et al. |
| 2003/0176914 A1 | 9/2003 | Rabkin et al. |
| 2003/0199921 A1 | 10/2003 | Palmer et al. |
| 2003/0204202 A1 | 10/2003 | Palmer et al. |
| 2003/0212430 A1 | 11/2003 | Bose et al. |
| 2004/0002752 A1 | 1/2004 | Griffin et al. |
| 2004/0006306 A1 | 1/2004 | Evans et al. |
| 2004/0006381 A1 | 1/2004 | Sequin et al. |
| 2004/0010308 A1 | 1/2004 | Zafrir-Pachter et al. |
| 2004/0019322 A1 | 1/2004 | Hoffmann |
| 2004/0026942 A1 | 2/2004 | Kessler et al. |
| 2004/0030378 A1 | 2/2004 | Khosravi et al. |
| 2004/0034386 A1 | 2/2004 | Fulton et al. |
| 2004/0049258 A1 | 3/2004 | Khosravi et al. |
| 2004/0054367 A1 | 3/2004 | Jimenez et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0073300 A1 | 4/2004 | Chouinard et al. |
| 2004/0078050 A1 | 4/2004 | Monstadt et al. |
| 2004/0078071 A1 | 4/2004 | Escamilla et al. |
| 2004/0079429 A1 | 4/2004 | Miller et al. |
| 2004/0088002 A1 | 5/2004 | Boyle et al. |
| 2004/0093065 A1 | 5/2004 | Yachia et al. |
| 2004/0098025 A1 | 5/2004 | Sepetka et al. |
| 2004/0102838 A1 | 5/2004 | Killion et al. |
| 2004/0106979 A1 | 6/2004 | Goicoechea et al. |
| 2004/0111912 A1 | 6/2004 | Storrer |
| 2004/0117003 A1 | 6/2004 | Ouriel et al. |
| 2004/0147939 A1 | 7/2004 | Rabkin et al. |
| 2004/0153117 A1 | 8/2004 | Clubb et al. |
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193246 A1 | 9/2004 | Ferrera |
| 2004/0199201 A1 | 10/2004 | Kellett et al. |
| 2004/0215312 A1 | 10/2004 | Andreas |
| 2004/0215319 A1 | 10/2004 | Berra et al. |
| 2004/0219439 A1 | 11/2004 | Asano et al. |
| 2004/0254628 A1 | 12/2004 | Nazzaro et al. |
| 2004/0260385 A1 | 12/2004 | Jones et al. |
| 2005/0015136 A1 | 1/2005 | Ikeuchi et al. |
| 2005/0021125 A1 | 1/2005 | Stack et al. |
| 2005/0033334 A1 | 2/2005 | Santra et al. |
| 2005/0033348 A1 | 2/2005 | Sepetka et al. |
| 2005/0033349 A1 | 2/2005 | Jones et al. |
| 2005/0033409 A1 | 2/2005 | Burke et al. |
| 2005/0038447 A1 | 2/2005 | Huffmaster |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0055047 A1 | 3/2005 | Greenhalgh |
| 2005/0060017 A1 | 3/2005 | Fischell et al. |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0090888 A1 | 4/2005 | Hines et al. |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman et al. |
| 2005/0125023 A1 | 6/2005 | Bates et al. |
| 2005/0126979 A1 | 6/2005 | Lowe et al. |
| 2005/0131515 A1 | 6/2005 | Cully et al. |
| 2005/0131516 A1 | 6/2005 | Greenhalgh |
| 2005/0159774 A1 | 7/2005 | Belef |
| 2005/0165441 A1 | 7/2005 | Mcguckin et al. |
| 2005/0177220 A1 | 8/2005 | Iaizzo et al. |
| 2005/0187612 A1 | 8/2005 | Edwin |
| 2005/0192661 A1 | 9/2005 | Griffen et al. |
| 2005/0209673 A1 | 9/2005 | Shaked |

(56) References Cited

U.S. PATENT DOCUMENTS

| | | |
|---|---|---|
| 2005/0209675 A1 | 9/2005 | Ton et al. |
| 2005/0209678 A1 | 9/2005 | Henkes et al. |
| 2005/0216050 A1 | 9/2005 | Sepetka et al. |
| 2005/0222583 A1 | 10/2005 | Cano et al. |
| 2005/0222607 A1 | 10/2005 | Palmer et al. |
| 2005/0222676 A1 | 10/2005 | Shanley et al. |
| 2005/0267570 A1 | 12/2005 | Shadduck |
| 2005/0277978 A1 | 12/2005 | Greenhalgh |
| 2006/0020321 A1 | 1/2006 | Parker |
| 2006/0025845 A1 | 2/2006 | Escamilla et al. |
| 2006/0025850 A1 | 2/2006 | Feller et al. |
| 2006/0030865 A1 | 2/2006 | Balg |
| 2006/0036281 A1 | 2/2006 | Patterson et al. |
| 2006/0052797 A1 | 3/2006 | Kanamaru |
| 2006/0052816 A1 | 3/2006 | Bates et al. |
| 2006/0058833 A1 | 3/2006 | Vancamp et al. |
| 2006/0058836 A1 | 3/2006 | Bose et al. |
| 2006/0058838 A1 | 3/2006 | Bose et al. |
| 2006/0074180 A1 | 4/2006 | Lipinski |
| 2006/0085065 A1 | 4/2006 | Krause et al. |
| 2006/0089703 A1 | 4/2006 | Escamilla et al. |
| 2006/0100663 A1 | 5/2006 | Palmer et al. |
| 2006/0106421 A1 | 5/2006 | Teoh |
| 2006/0106448 A1 | 5/2006 | Shaked |
| 2006/0122643 A1 | 6/2006 | Wasicek |
| 2006/0122685 A1 | 6/2006 | Bonsignore et al. |
| 2006/0135947 A1 | 6/2006 | Soltesz et al. |
| 2006/0142841 A1 | 6/2006 | Khosravi et al. |
| 2006/0142849 A1 | 6/2006 | Killion et al. |
| 2006/0161243 A1 | 7/2006 | Feamot et al. |
| 2006/0195118 A1 | 8/2006 | Richardson |
| 2006/0195172 A1 | 8/2006 | Luo et al. |
| 2006/0200048 A1 | 9/2006 | Furst et al. |
| 2006/0200221 A1 | 9/2006 | Malewicz |
| 2006/0224179 A1 | 10/2006 | Kucharczyk et al. |
| 2006/0224180 A1 | 10/2006 | Anderson et al. |
| 2006/0229645 A1 | 10/2006 | Bonnette et al. |
| 2006/0259119 A1 | 11/2006 | Rucker |
| 2006/0265054 A1 | 11/2006 | Greenhalgh et al. |
| 2006/0271090 A1 | 11/2006 | Shaked et al. |
| 2006/0276883 A1 | 12/2006 | Greenberg et al. |
| 2006/0287701 A1 | 12/2006 | Pal |
| 2006/0287704 A1 | 12/2006 | Hartley et al. |
| 2007/0005105 A1* | 1/2007 | Kusleika .......... A61F 2/013 606/200 |
| 2007/0032852 A1 | 2/2007 | Machek et al. |
| 2007/0043424 A1 | 2/2007 | Pryor |
| 2007/0043425 A1 | 2/2007 | Hartley et al. |
| 2007/0055299 A1 | 3/2007 | Ishimaru et al. |
| 2007/0055358 A1 | 3/2007 | Krolik et al. |
| 2007/0055360 A1 | 3/2007 | Hanson et al. |
| 2007/0055365 A1 | 3/2007 | Greenberg et al. |
| 2007/0067011 A1 | 3/2007 | Krolik et al. |
| 2007/0073376 A1 | 3/2007 | Krolik et al. |
| 2007/0088387 A1 | 4/2007 | Eskridge et al. |
| 2007/0100425 A1 | 5/2007 | Sequin et al. |
| 2007/0118205 A1 | 5/2007 | Davidson et al. |
| 2007/0123972 A1 | 5/2007 | Greenberg et al. |
| 2007/0135826 A1 | 6/2007 | Zaver et al. |
| 2007/0135888 A1 | 6/2007 | Khosravi et al. |
| 2007/0141036 A1 | 6/2007 | Gorrochategui et al. |
| 2007/0142896 A1 | 6/2007 | Anderson et al. |
| 2007/0156170 A1 | 7/2007 | Hancock et al. |
| 2007/0156228 A1 | 7/2007 | Majercak et al. |
| 2007/0162109 A1 | 7/2007 | Davila et al. |
| 2007/0179513 A1 | 8/2007 | Deutsch |
| 2007/0185501 A1 | 8/2007 | Martin et al. |
| 2007/0191866 A1 | 8/2007 | Palmer et al. |
| 2007/0191884 A1 | 8/2007 | Eskridge et al. |
| 2007/0191924 A1 | 8/2007 | Rudakov |
| 2007/0198028 A1 | 8/2007 | Miloslavski et al. |
| 2007/0198029 A1 | 8/2007 | Martin et al. |
| 2007/0198030 A1 | 8/2007 | Martin et al. |
| 2007/0198075 A1 | 8/2007 | Levy |
| 2007/0200014 A1 | 8/2007 | Nobili |
| 2007/0203452 A1 | 8/2007 | Mehta |
| 2007/0203559 A1 | 8/2007 | Freudenthal et al. |
| 2007/0208367 A1 | 9/2007 | Fiorella et al. |
| 2007/0208371 A1 | 9/2007 | French et al. |
| 2007/0219621 A1 | 9/2007 | Hartley et al. |
| 2007/0225749 A1 | 9/2007 | Martin et al. |
| 2007/0225794 A1 | 9/2007 | Thramann et al. |
| 2007/0225795 A1 | 9/2007 | Granada et al. |
| 2007/0233236 A1 | 10/2007 | Pryor |
| 2007/0250040 A1 | 10/2007 | Provost et al. |
| 2007/0266542 A1 | 11/2007 | Melsheimer |
| 2007/0270932 A1 | 11/2007 | Headley et al. |
| 2007/0288037 A1 | 12/2007 | Cheng et al. |
| 2007/0288038 A1 | 12/2007 | Bimbo |
| 2007/0288054 A1 | 12/2007 | Tanaka et al. |
| 2007/0288080 A1 | 12/2007 | Maccollum et al. |
| 2007/0288083 A1 | 12/2007 | Hines |
| 2007/0293846 A1 | 12/2007 | Von et al. |
| 2007/0299503 A1 | 12/2007 | Berra et al. |
| 2008/0001333 A1 | 1/2008 | Kleine et al. |
| 2008/0015558 A1 | 1/2008 | Harlan |
| 2008/0015682 A1 | 1/2008 | Majercak et al. |
| 2008/0033528 A1 | 2/2008 | Satasiya et al. |
| 2008/0039926 A1 | 2/2008 | Majercak et al. |
| 2008/0039930 A1 | 2/2008 | Jones et al. |
| 2008/0045995 A1 | 2/2008 | Guterman et al. |
| 2008/0046064 A1 | 2/2008 | Sequin et al. |
| 2008/0046072 A1 | 2/2008 | Laborde et al. |
| 2008/0051803 A1 | 2/2008 | Monjtadt et al. |
| 2008/0058724 A1 | 3/2008 | Wallace |
| 2008/0071178 A1 | 3/2008 | Greenland et al. |
| 2008/0077175 A1 | 3/2008 | Palmer |
| 2008/0082107 A1 | 4/2008 | Miller et al. |
| 2008/0082159 A1 | 4/2008 | Tseng et al. |
| 2008/0086196 A1 | 4/2008 | Truckai et al. |
| 2008/0097495 A1 | 4/2008 | Feller et al. |
| 2008/0103477 A1 | 5/2008 | Jones |
| 2008/0103585 A1 | 5/2008 | Monstadt et al. |
| 2008/0109063 A1 | 5/2008 | Hancock et al. |
| 2008/0109067 A1 | 5/2008 | Caro et al. |
| 2008/0114439 A1 | 5/2008 | Ramaiah et al. |
| 2008/0114445 A1 | 5/2008 | Melsheimer et al. |
| 2008/0119888 A1 | 5/2008 | Huffmaster |
| 2008/0125855 A1 | 5/2008 | Henkes et al. |
| 2008/0140107 A1 | 6/2008 | Bei et al. |
| 2008/0140181 A1 | 6/2008 | Reynolds et al. |
| 2008/0147100 A1 | 6/2008 | Wallace |
| 2008/0161903 A1 | 7/2008 | Sequin et al. |
| 2008/0161936 A1 | 7/2008 | Feller et al. |
| 2008/0167708 A1 | 7/2008 | Molland et al. |
| 2008/0183185 A1 | 7/2008 | Miller et al. |
| 2008/0183198 A1 | 7/2008 | Sepetka et al. |
| 2008/0188865 A1 | 8/2008 | Miller et al. |
| 2008/0195140 A1 | 8/2008 | Myla et al. |
| 2008/0200946 A1 | 8/2008 | Braun et al. |
| 2008/0208319 A1 | 8/2008 | Rabkin et al. |
| 2008/0221554 A1 | 9/2008 | Oconnor et al. |
| 2008/0221600 A1 | 9/2008 | Dieck et al. |
| 2008/0221664 A1 | 9/2008 | Bales et al. |
| 2008/0221671 A1 | 9/2008 | Chouinard et al. |
| 2008/0228216 A1 | 9/2008 | Strauss et al. |
| 2008/0234795 A1 | 9/2008 | Snow et al. |
| 2008/0243229 A1 | 10/2008 | Wallace et al. |
| 2008/0243232 A1 | 10/2008 | Hegg et al. |
| 2008/0247943 A1 | 10/2008 | Lanza et al. |
| 2008/0249598 A1 | 10/2008 | Sherry |
| 2008/0255678 A1 | 10/2008 | Cully et al. |
| 2008/0262506 A1 | 10/2008 | Griffin et al. |
| 2008/0262528 A1 | 10/2008 | Martin |
| 2008/0262532 A1 | 10/2008 | Martin |
| 2008/0262592 A1 | 10/2008 | Jordan et al. |
| 2008/0269774 A1 | 10/2008 | Garcia et al. |
| 2008/0269868 A1 | 10/2008 | Bei et al. |
| 2008/0275497 A1 | 11/2008 | Palmer et al. |
| 2008/0275498 A1 | 11/2008 | Palmer et al. |
| 2008/0275536 A1 | 11/2008 | Zarins et al. |
| 2008/0281302 A1 | 11/2008 | Murphy et al. |
| 2008/0281350 A1 | 11/2008 | Sepetka et al. |
| 2008/0281393 A1 | 11/2008 | Armstrong et al. |

(56) References Cited

U.S. PATENT DOCUMENTS

| | | |
|---|---|---|
| 2008/0281397 A1 | 11/2008 | Killion et al. |
| 2008/0281403 A1 | 11/2008 | Kavteladze |
| 2008/0306503 A1 | 12/2008 | Que et al. |
| 2008/0306504 A1 | 12/2008 | Win et al. |
| 2008/0312732 A1 | 12/2008 | Hartley et al. |
| 2008/0319525 A1 | 12/2008 | Tieu et al. |
| 2008/0319533 A1 | 12/2008 | Lehe |
| 2009/0018633 A1 | 1/2009 | Lindquist et al. |
| 2009/0018634 A1 | 1/2009 | State |
| 2009/0018640 A1 | 1/2009 | State |
| 2009/0024157 A1 | 1/2009 | Anukhin |
| 2009/0025820 A1 | 1/2009 | Adams |
| 2009/0030502 A1 | 1/2009 | Sun et al. |
| 2009/0036964 A1 | 2/2009 | Heringes et al. |
| 2009/0036968 A1 | 2/2009 | Hepworth et al. |
| 2009/0036977 A1 | 2/2009 | Rassat et al. |
| 2009/0062726 A1 | 3/2009 | Ford et al. |
| 2009/0062773 A1 | 3/2009 | Cornish et al. |
| 2009/0062834 A1 | 3/2009 | Moftakhar et al. |
| 2009/0068097 A1 | 3/2009 | Sevrain |
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0125053 A1 | 5/2009 | Ferrera et al. |
| 2009/0163851 A1 | 6/2009 | Holloway et al. |
| 2009/0192455 A1 | 7/2009 | Ferrera et al. |
| 2009/0275974 A1 | 11/2009 | Marchand et al. |
| 2009/0292297 A1 | 11/2009 | Ferrere |
| 2009/0299393 A1 | 12/2009 | Martin et al. |
| 2010/0022951 A1 | 1/2010 | Ferrera et al. |
| 2010/0100106 A1 | 4/2010 | Ferrera |
| 2010/0114017 A1 | 5/2010 | Lenker et al. |
| 2010/0114135 A1 | 5/2010 | Wilson et al. |
| 2010/0137892 A1 | 6/2010 | Dreher et al. |
| 2010/0152766 A1 | 6/2010 | Dieck et al. |
| 2010/0174309 A1 | 7/2010 | Fulkerson et al. |
| 2010/0217187 A1 | 8/2010 | Ferrera et al. |
| 2010/0256600 A1 | 10/2010 | Ferrera |
| 2010/0268265 A1* | 10/2010 | Krolik ............... A61B 17/221 606/200 |
| 2010/0299911 A1 | 12/2010 | Gianotti et al. |
| 2010/0318097 A1 | 12/2010 | Cragg et al. |
| 2011/0009875 A1 | 1/2011 | Grandfield et al. |
| 2011/0009941 A1 | 1/2011 | Sanders et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0035648 A1 | 2/2012 | Wilson et al. |
| 2012/0041160 A1 | 2/2012 | Benham et al. |
| 2012/0041164 A1 | 2/2012 | Kolb et al. |
| 2012/0041411 A1 | 2/2012 | Horton et al. |
| 2012/0041449 A1 | 2/2012 | Eckhouse et al. |
| 2012/0041459 A1 | 2/2012 | Fiorella et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065600 A1 | 3/2012 | Ashmead et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0078285 A1 | 3/2012 | Griffin |
| 2012/0083868 A1 | 4/2012 | Shrivastava et al. |
| 2012/0089216 A1 | 4/2012 | Rapaport et al. |
| 2012/0116443 A1 | 5/2012 | Ferrera et al. |
| 2013/0030461 A1 | 1/2013 | Marks et al. |
| 2013/0281788 A1 | 10/2013 | Garrison |
| 2014/0276074 A1 | 9/2014 | Warner |
| 2014/0343595 A1 | 11/2014 | Monstadt et al. |
| 2014/0343596 A1 | 11/2014 | Slee et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| DE | 2804058 A1 | 8/1978 |
| DE | 2821048 B1 | 11/1979 |
| DE | 84354895 U1 | 8/1986 |
| DE | 19703482 A1 | 8/1998 |
| DE | 10010640 A1 | 9/2001 |
| EP | 0321912 B1 | 2/1995 |
| EP | 0804904 A1 | 11/1997 |
| EP | 0820729 A1 | 1/1998 |
| EP | 0826341 A1 | 3/1998 |
| EP | 1000590 A1 | 5/2000 |
| EP | 1005837 A2 | 6/2000 |
| EP | 1009295 A1 | 6/2000 |
| EP | 1009296 A1 | 6/2000 |
| EP | 1201260 A1 | 5/2002 |
| EP | 1225844 A2 | 7/2002 |
| EP | 126663 9 A2 | 12/2002 |
| EP | 1266640 A2 | 12/2002 |
| EP | 1323385 A2 | 7/2003 |
| EP | 1329196 A1 | 7/2003 |
| EP | 1351626 A2 | 10/2003 |
| EP | 1366720 A1 | 12/2003 |
| EP | 1400219 A1 | 3/2004 |
| EP | 1437097 A1 | 7/2004 |
| EP | 2257248 B1 | 10/2011 |
| EP | 2301450 B1 | 11/2011 |
| EP | 2417919 A2 | 2/2012 |
| EP | 2319575 B1 | 11/2013 |

(56) References Cited

FOREIGN PATENT DOCUMENTS

| | | |
|---|---|---|
| FR | 2343488 A1 | 10/1977 |
| GB | 2020557 A | 11/1979 |
| JP | 2975584 B2 | 11/1999 |
| JP | 2001178830 A | 7/2001 |
| JP | 2003033359 A | 2/2003 |
| JP | 2006075233 A | 3/2006 |
| JP | 2007185363 A | 7/2007 |
| JP | 2014004219 A | 1/2014 |
| JP | 2018118132 A | 8/2018 |
| KR | 20180102877 A | 9/2018 |
| WO | WO 9403127 A1 | 2/1994 |
| WO | WO 9617634 A2 | 6/1996 |
| WO | WO 9628116 A1 | 9/1996 |
| WO | WO 9704711 A1 | 2/1997 |
| WO | WO 9825656 A3 | 10/1998 |
| WO | WO 9855173 A1 | 12/1998 |
| WO | WO 9855175 A1 | 12/1998 |
| WO | WO 9916382 A2 | 4/1999 |
| WO | WO 9923976 A1 | 5/1999 |
| WO | WO 9925252 A1 | 5/1999 |
| WO | WO 9929264 A1 | 6/1999 |
| WO | WO 9944542 A2 | 9/1999 |
| WO | WO 9948429 A1 | 9/1999 |
| WO | WO 9948440 A1 | 9/1999 |
| WO | WO 0012166 A1 | 3/2000 |
| WO | WO 0032265 A1 | 6/2000 |
| WO | WO 0053120 A1 | 9/2000 |
| WO | WO 0059405 A1 | 10/2000 |
| WO | WO 0108743 A1 | 2/2001 |
| WO | WO 0132099 A2 | 5/2001 |
| WO | WO 0136034 A2 | 5/2001 |
| WO | WO 0145569 A1 | 6/2001 |
| WO | WO 0172240 A1 | 10/2001 |
| WO | WO 0193780 A2 | 12/2001 |
| WO | WO 2004008991 A1 | 1/2004 |
| WO | WO 2004049982 A2 | 6/2004 |
| WO | WO 2004093696 A1 | 11/2004 |
| WO | WO 2005058196 A2 | 6/2005 |
| WO | WO 2007089897 A2 | 8/2007 |
| WO | WO 2007121005 A1 | 10/2007 |
| WO | WO 2008063156 A2 | 5/2008 |
| WO | WO 2008117256 A2 | 10/2008 |
| WO | WO 2008117257 A2 | 10/2008 |
| WO | WO 2008124728 A1 | 10/2008 |
| WO | WO 2009067629 A2 | 5/2009 |
| WO | WO 2009086154 A2 | 7/2009 |
| WO | WO 2009105710 A1 | 8/2009 |
| WO | WO 2009114046 A2 | 9/2009 |
| WO | WO 2009124288 A1 | 10/2009 |
| WO | WO 2009126747 A1 | 10/2009 |
| WO | WO 2010010545 A1 | 1/2010 |
| WO | WO 2010023671 A2 | 3/2010 |
| WO | WO 2010046897 A1 | 4/2010 |
| WO | WO 2010049121 A2 | 5/2010 |
| WO | WO 2010062363 A1 | 6/2010 |
| WO | WO 2010102307 A1 | 9/2010 |
| WO | WO 2010115642 A1 | 10/2010 |
| WO | WO 2010121037 A1 | 10/2010 |
| WO | WO 2010121049 A1 | 10/2010 |
| WO | WO 2011054531 A2 | 5/2011 |
| WO | WO 2011095352 A1 | 8/2011 |
| WO | WO 2011133486 A1 | 10/2011 |
| WO | WO 2011135556 A1 | 11/2011 |
| WO | WO 2011144336 A1 | 11/2011 |
| WO | WO 2011147567 A1 | 12/2011 |
| WO | WO 2012009675 A2 | 1/2012 |
| WO | WO 2012025245 A1 | 3/2012 |
| WO | WO 2012025247 A1 | 3/2012 |
| WO | WO 2015141317 A1 | 9/2015 |
| WO | WO 2017192999 A1 | 11/2017 |
| WO | WO 2018019829 A1 | 2/2018 |
| WO | WO 2018033401 A1 | 2/2018 |
| WO | WO 2018046408 A2 | 3/2018 |
| WO | WO 2018137029 A1 | 8/2018 |
| WO | WO 2018137030 A1 | 8/2018 |
| WO | WO 2018145212 A1 | 8/2018 |
| WO | WO 2018156813 A1 | 8/2018 |
| WO | WO 2018172891 A1 | 9/2018 |
| WO | WO 2018187776 A1 | 10/2018 |

OTHER PUBLICATIONS

Abstracts from the 2009 International Stroke Conference, Stroke, 2009; 40, pp. e247-e248, originally published online Feb. 16, 2009.
Castano, C, "Use of the new Solitaire (TM) AB Device for Mechanical Thrombectomy when Merci Clot Retrieval Has Failed to Remove the Clot: A Case Report," Interventional Neuroradiology, Jul. 2009 1592) pp. 209-214.
David M. Pelz, et al., Advances in Interventional Neuroradiology 2007; American Heart Association Journal, Nov. 2007 edition.
Doerfler, A. et al., "A Novel Flexible, Retrievable Endovascular Stent System for Small-Vessel Anatomy: Preliminary In Vivo Data," Am. J. Neuroradiol. vol. 26, pp. 862-868 (Apr. 2005).
E.I. Levy et al., Self-Expanding Stents for Recanalization of Acute Cerebrovascular Occulsions; AJNR May 28, 2007.
Eric Sauvegeau, MD et al. Middle Cerebral Artery Stenting for Acute Ischemic Stroke After Unsuccessful Merci Retrieval; Special Technical Report; Neurosurgery 60:701-706, 2007.
Ev3 Solitaire AB Instructions for Use (IFU) dated Dec. 2007. The first commercial sale of the products numbered SAB-4-15 and SAB 4 20, referenced in the ev3 Solitaure AB IFU dated Dec. 2007, occurred on Jan. 4, 2008.
Ev3 Solitaure Brochure R2 dated Jan. 12, 2009.
Henkes, H. et al., "A Microcatheter-Delivered Highly-Flexible and Fully-Retrievable Stent, Specifically Designed for Intracranial Use," Interventional Neuroradiology, vol. 9, pp. 391-393 (Dec. 2003).
Henkes, H. et al. "Endovascular acute ischemic stroke treatment using the self-expanding and fully retrievable Solitaire stent," poster exhibition displayed on one or both of Feb. 18 and 19, 2009, at the International Stroke Conference, San Diego, California.
Imai, K, "Clot removal Therapy by Aspiration and Extraction for Acute Embolic Carotid Occlusion," American Journal of Neuroradiology, Aug. 2006, vol. 27, pp. 1521-1527.
J Gralla et al, "Mechanical Thrombectomy for Acute Ischemic Stroke," Stroke 37:3019-20124, Dec. 2006.
J Gralla, et al, "A Dedicated Animal Model for Mechanical Thrombectomy in Acute Stroke," ANJR 27:1357-61, Jun.-Jul. 2006.
Kathy Robertson, Stroke device startup lands National Science Foundation grant, Sacramento Business Journal, Oct. 23, 2009, Sacramento, California.
Liebig, T. et al., "A novel self-expanding fully retrievable intracranial stent (SOLO): experience in nine procedures of stent-assisted aneurysm coil occlusion," Neuroradiology vol. 48, pp. 471-478 (Jul. 2006).
Liebig, T. et al, "Multimodal endovascular treatment of ischemic stroke by mechanical thrombectomy; a two center / two years experience" Z Vajda, et al (p. 6).
Michael E. Kelly, MD, et al., Recanalization of an Acute Cerebral Artery Occlusion Using a Self-Expanding, Reconstrainable, Intracranial Microstent as a Temporary Endovascular Bypass; AHA Journal, Jun. 2008 edition.
Micro Therapeutics, Inc., DBA EV3 Neurovascular, Inc., Fully deployable. Completely retrievable, Solitaire AB, Neurovascular Remodeling Device. Mar. 2008.
Micro Therapeutics, Inc., DBA EV3 Neurovascular, Inc., Solitaire FR Revascularization Device, Instructions for Use, Rev. Mar. 2009.
Nesbit, G, "New and Future Endovascular Treatment Strategies for Acute ischemic Stroke," Journal of Vascula4r and Interventional Radiology, Jan. 2004 15(1)pp S103-S110.
Philippa C. Lavallee, et al., Stent-Assisted Endovascular Thrombolysis Versus Intravenous Thrombolysis in Internal Carotid Artery Dissection with Tandem Internal Carotid and Middle Cerebral Artery Occlusion, AHA 2007.
Sauvegeau, et al Middle Cerebral Artery Stenting for Acute ischemic Stroke After Unsuccessful merci Retrieval; Special Technical Report; Neurosurgery 60:701-706, 2007.

(56) References Cited

OTHER PUBLICATIONS

Schumacher, H, "Endovascular mechanical Thrombectomy of an Occluded Superior Division Branch of the left MCA for Acute Cardioembolic Stroke," Cardiovascular and Interventional Radiology, Jun. 2003 26(3) pp. 305-308.
T.W. Duerig, D.E. Tolomeo, M. Wholey, An Overview of Superelastic Stent Design. Min. Invas Ther & Allied Technol 2000: 9(3/4) 235-246.
V Marder et al, "Analysis of Thrombi Retrieved from Cerebral Arteries of Patients With Acute Ischemic Stroke" Stroke 37:2086-2093, Aug. 2006.
Wakhloo, et al., "Retrievable Closed Cell Intracranial Stent for Foreign Body and Clot Removal," Neurosurgery, May 2008.
Wildberger, J, "Percutaneous Venous Thrombectomy Using the Arrow-Tretorola Percutaneous Thrombolytic Device (PTD) with Temporary Caval Filtration; In Vitro Investigations." Cardiovascular and Interventioanl Radiology, Mar. 2005 26920 pp. 221-227
Yavuz, K. et al., "Immediate and midterm follow-up results of using an electrodetachable, fully retrievable SOLO stent system in the endovascular coil occlusion of wide-necked cerebral aneurysms," J. Neurosurg, vol. 107, pp. 49-55 (Jul. 2007).

\* cited by examiner

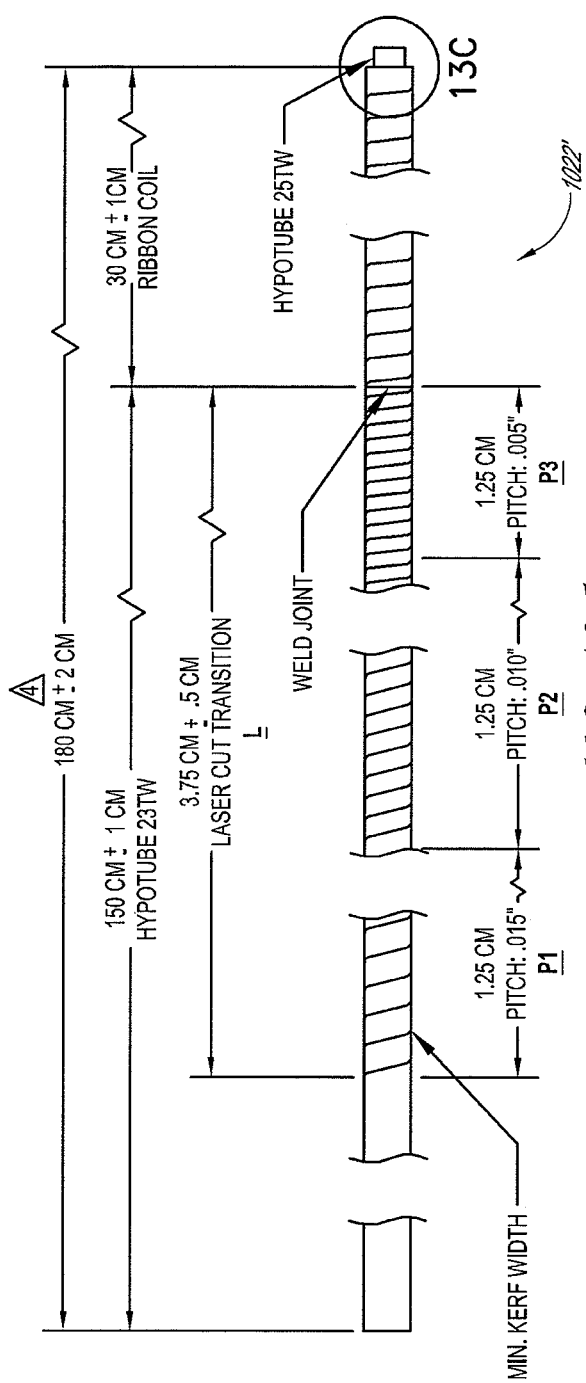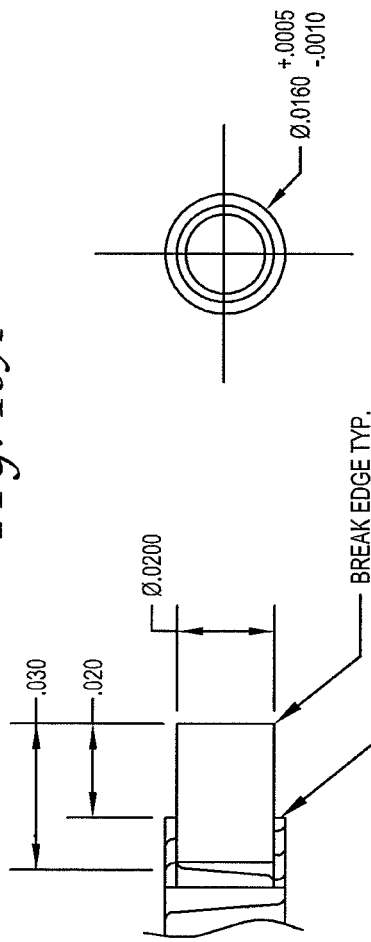
FIG. 13A
FIG. 13B
FIG. 13C
FIG. 13D

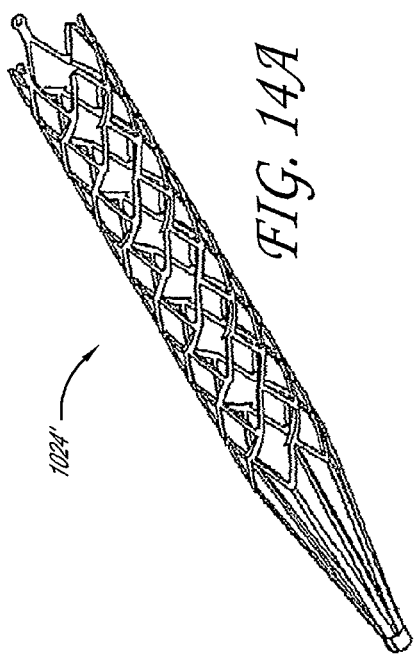
FIG. 14A
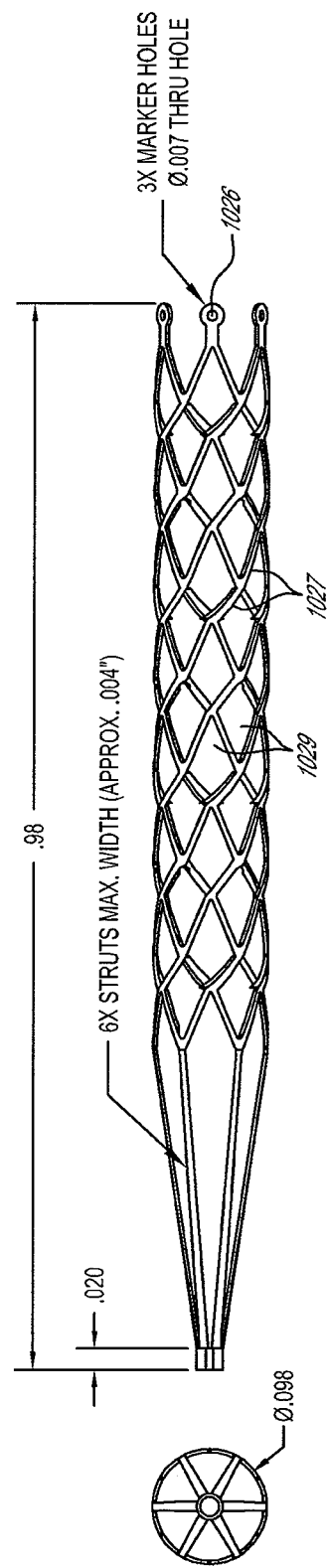
FIG. 14B
FIG. 14C

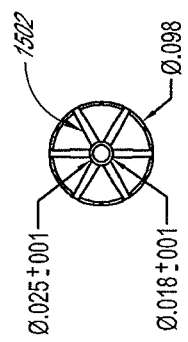
FIG. 15D
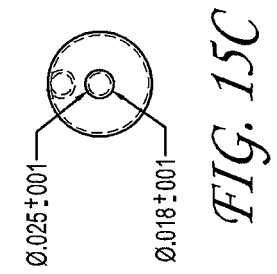
FIG. 15C
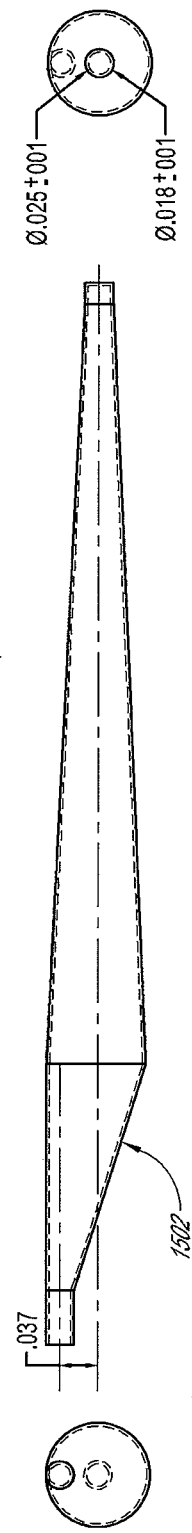
FIG. 15A
FIG. 15B

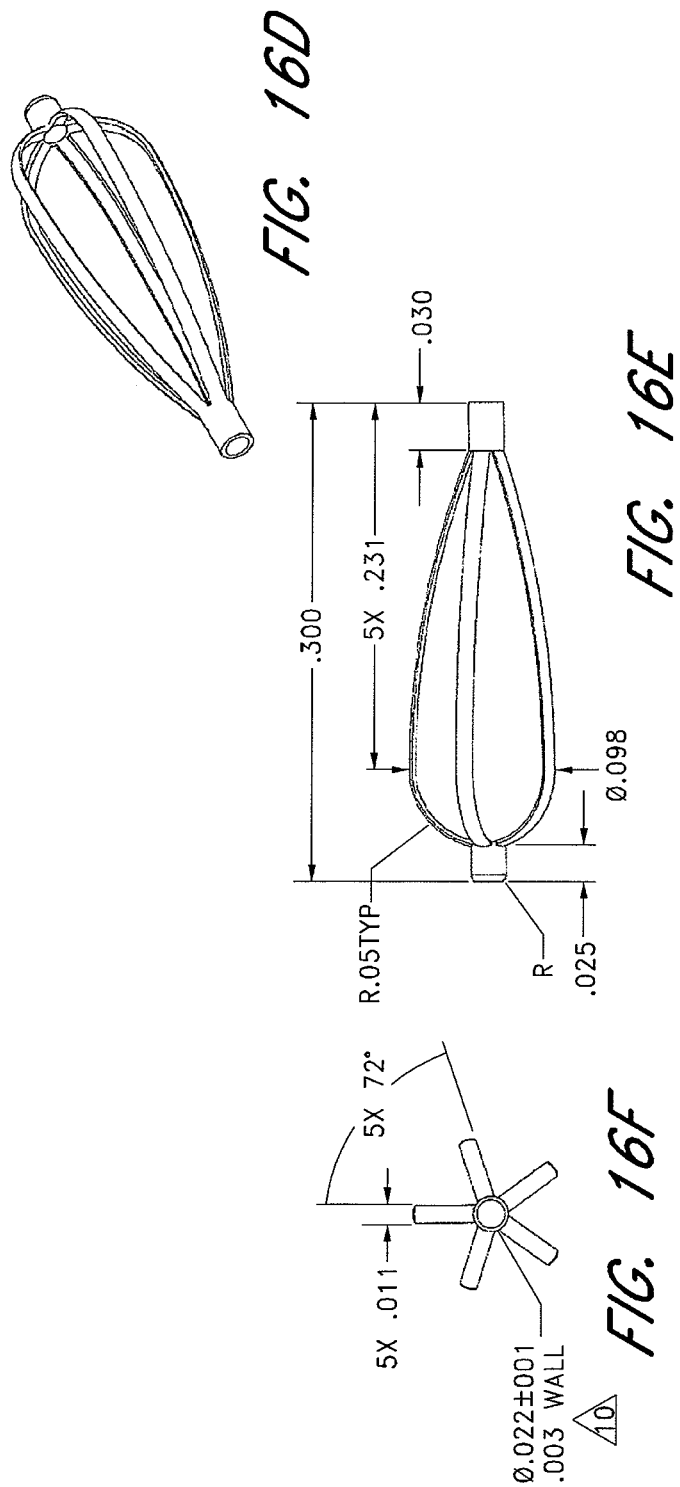

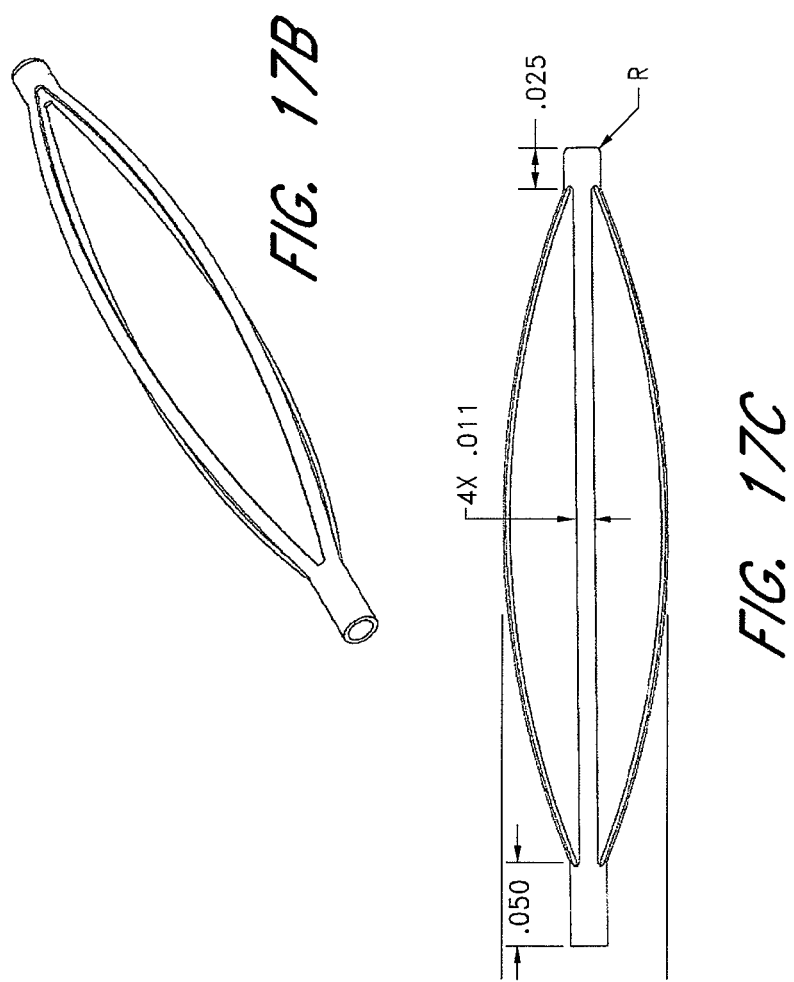

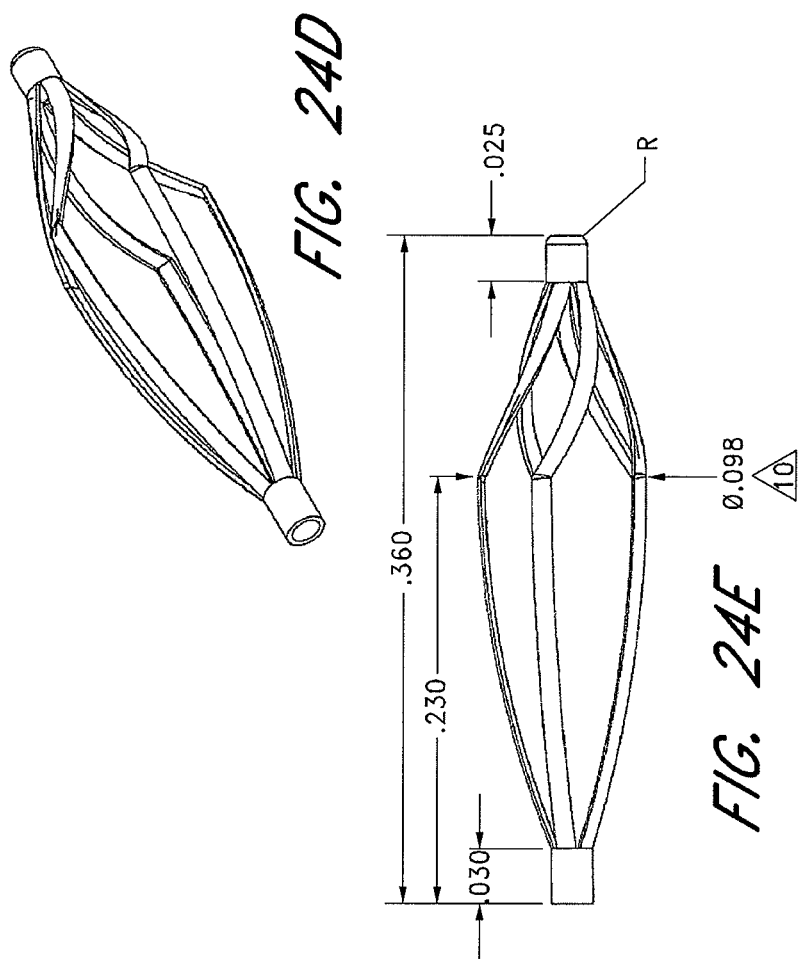
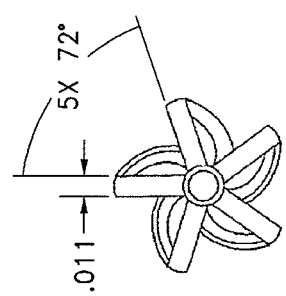
FIG. 24D
FIG. 24E
FIG. 24F

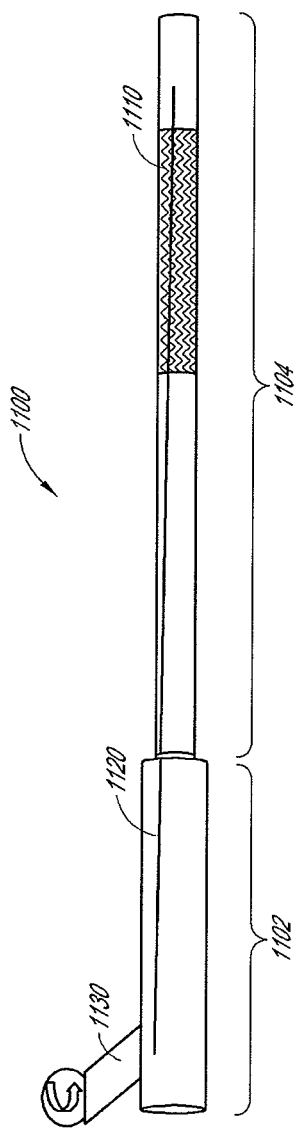
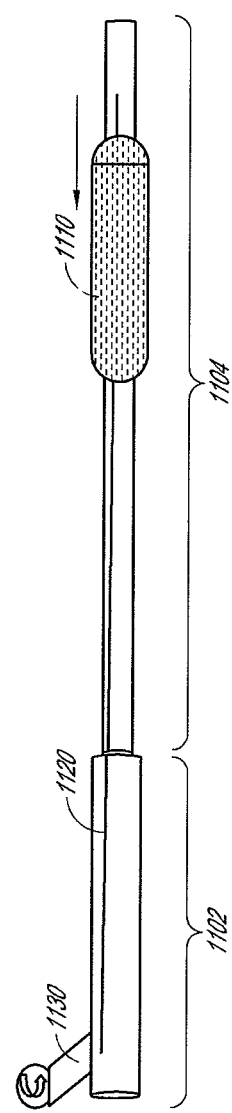
FIG. 25A
FIG. 25B

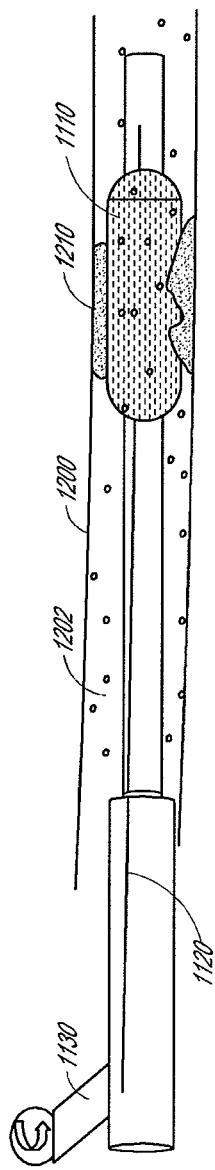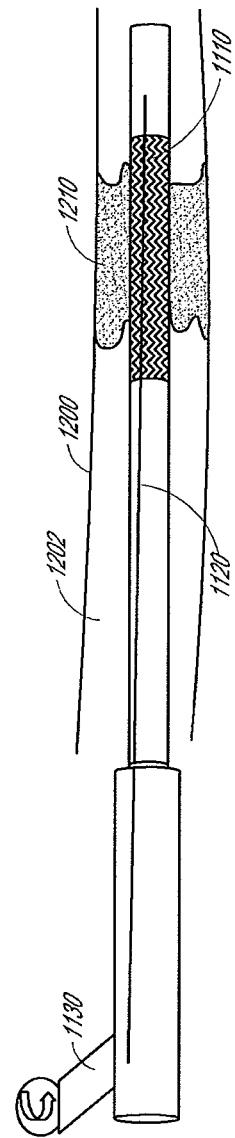
FIG. 26A
FIG. 26B

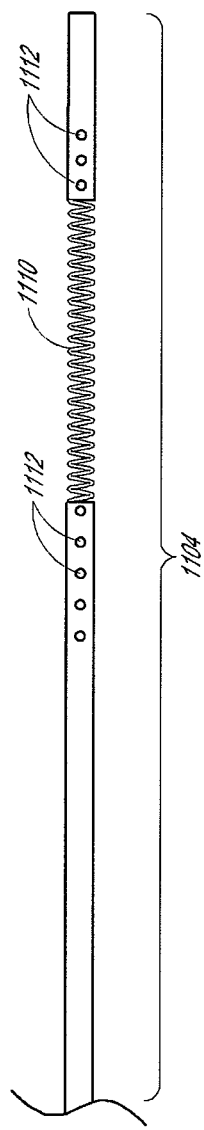
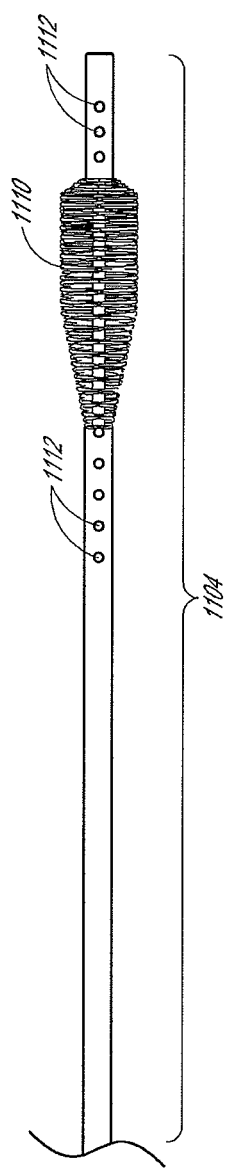
FIG. 29A
FIG. 29B

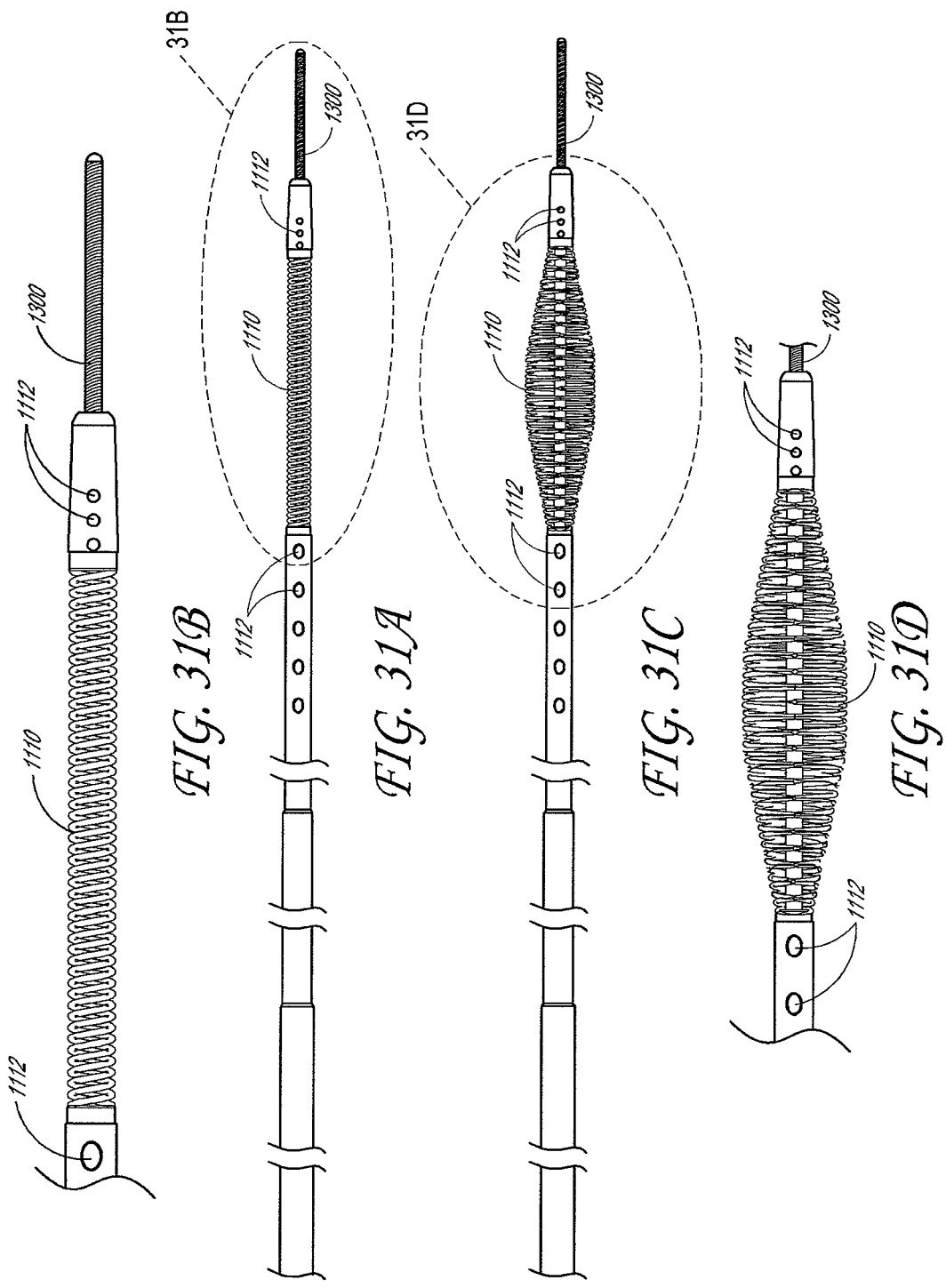

RESTORING BLOOD FLOW AND CLOT REMOVAL DURING ACUTE ISCHEMIC STROKE

RELATED APPLICATIONS

This application is a continuation of U.S. application Ser. No. 14/611,564, which is a continuation of U.S. application Ser. No. 13/341,186, filed Dec. 30, 2011, and issued as U.S. Pat. No. 8,945,172, which is a continuation of U.S. application Ser. No. 12/475,389, filed May 29, 2009, and issued as U.S. Pat. No. 8,088,140, which claims priority to U.S. Provisional Application No. 61/057,613, filed May 30, 2008, and U.S. Provisional Application No. 61/166,725, filed Apr. 4, 2009, and which is a continuation-in-part of each of U.S. application Ser. No. 12/182,370, filed Jul. 30, 2008, and issued as U.S. Pat. No. 9,220,522; U.S. application Ser. No. 12/123,390, filed May 19, 2008, and issued as U.S. Pat. No. 9,198,687; and U.S. application Ser. No. 12/422,105, filed on Apr. 10, 2009, and issued as U.S. Pat. No. 8,545,514; the contents of each of which are incorporated by reference herein in their entirety. U.S. application Ser. No. 13/341,186 is also a continuation-in-part of U.S. application Ser. No. 12/123,390, filed May 19, 2008, which claims priority to U.S. Provisional Application No. 60/980,736, filed Oct. 17, 2007; U.S. Provisional Application No. 60/987,384, filed Nov. 12, 2007; U.S. Provisional Application No. 60/989,422, filed Nov. 20, 2007; U.S. Provisional Application No. 61/015,154, filed Dec. 19, 2007; U.S. Provisional Application No. 61/019,506, filed Jan. 7, 2008; and U.S. Provisional Application No. 61/044,392, filed Apr. 11, 2008, each of which are incorporated by reference herein in their entirety.

BACKGROUND

The present disclosure relates to stroke treatment systems. Particularly, the present disclosure relates to improved devices for restoring blood flow and embolus removal during acute ischemic stroke.

SUMMARY

According to embodiments, a process for restoring blood flow and embolus removal during acute ischemic stroke, comprises, in combination: accessing an artery having embolic/occlusion issues with a reperfusion/clot removal device, reperfusing the subject vessel with the reperfusion/clot removal device, by engaging the subject embolus, removing the subject embolus from the vessel, and withdrawing the reperfusion/clot removal device and attached embolus.

Briefly stated, improved processes and devices restore blood flow to permit autolysis of clots, or enable capture of emboli in their entirety without fragmenting while arterial access is maintained, preserving the integrity of patients' vasculature.

Disclosed is a process for restoring blood flow and embolus removal during acute ischemic stroke, comprising in combination: accessing an artery with a catheter system; locating an embolic/occluded zone within a target vessel or branch; contacting the subject embolus/clot with a reperfusion/clot removal device; reperfusing the target vessel or branch by engaging the subject embolus/clot and through autolysis; and removing the subject embolus/clot by withdrawing the reperfusion/clot removal device without fragmenting the same. The contacting step may further comprise deploying the reperfusion/clot removal device whereby a first end of the device operatively abuts the subject embolus/clot. The reperfusing step may further comprise at least one of revascularizing and recanalizing the embolic/occluded zone by manipulating the device and establishing a flow path or microcatheter access. The removing step may further comprise recapturing the device or moving an entrapped/embolized embolus/clot down the intracranial tree to a more stable location.

Also disclosed is a product by the above disclosed process.

A product for the above disclosed process may include at least one device selected from the group of everted, stent-like members, basket-like clot removal devices having everted distal tips, and hybrid devices of the first two-types. The product may further comprise nitinol or at least one of open and closed cells. The product may have variable cell size at different parts of said device. The fibrous nature of clots/emboli and cell structure may facilitate clot attachment to the device.

Also disclosed is an extraction device comprising, in combination: a microcatheter and a capturing device configured to be selectively disposed within a lumen of the microcatheter, wherein the capturing device includes an opening configured to accept passage of a clot to within the capturing device and a distal end configured to contain the clot within the capturing device. The opening may include a mouth disposed on a middle section of the capturing device, an open-cell structure of a mesh netting that contributes to the structure of the capturing device, or an everted section on a proximal end of the capturing device.

DRAWINGS

The above-mentioned features and objects of the present disclosure will become more apparent with reference to the following description taken in conjunction with the accompanying drawings wherein like reference numerals denote like elements and in which.

Figure 9:
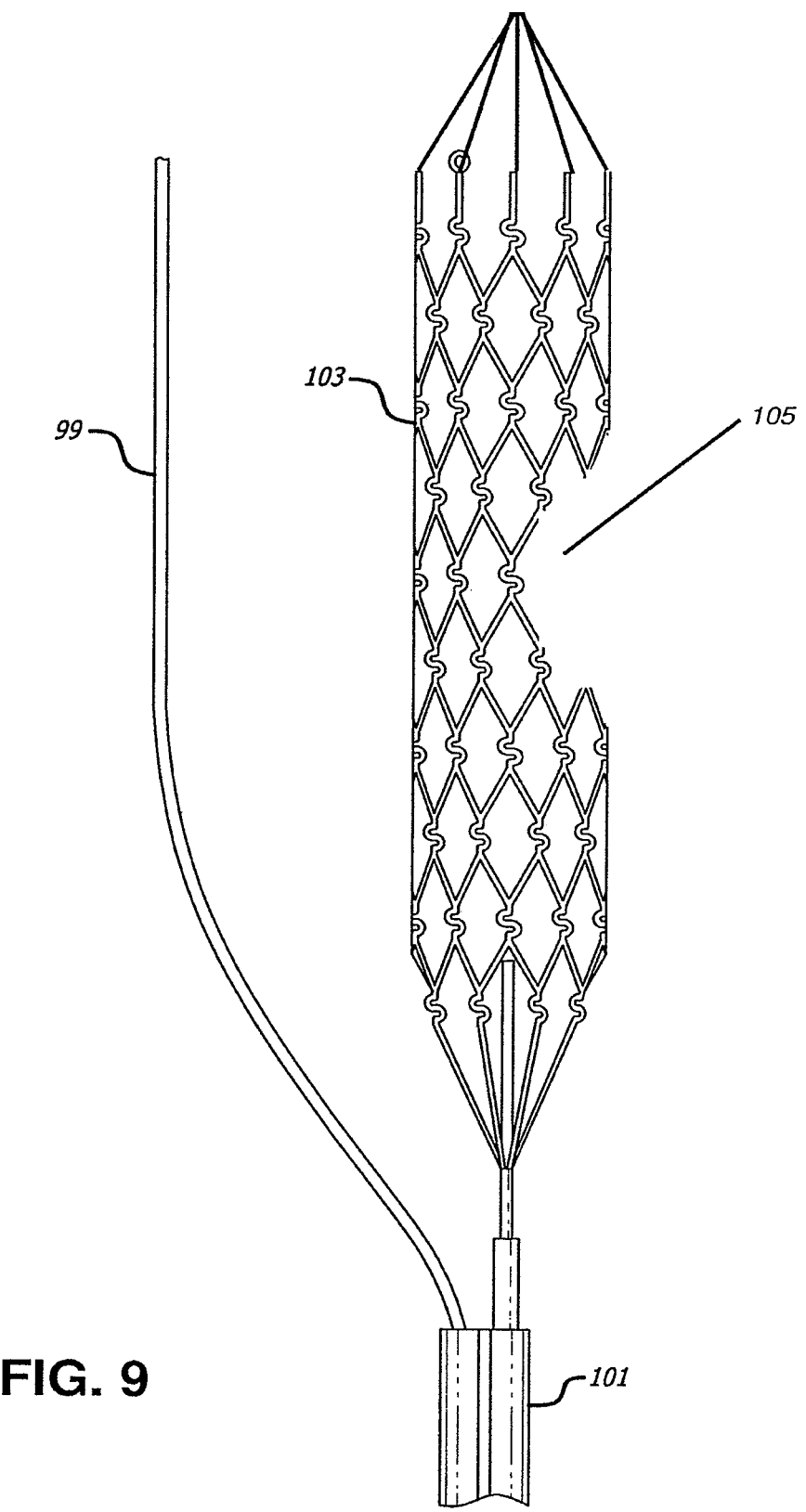
Figure 10:
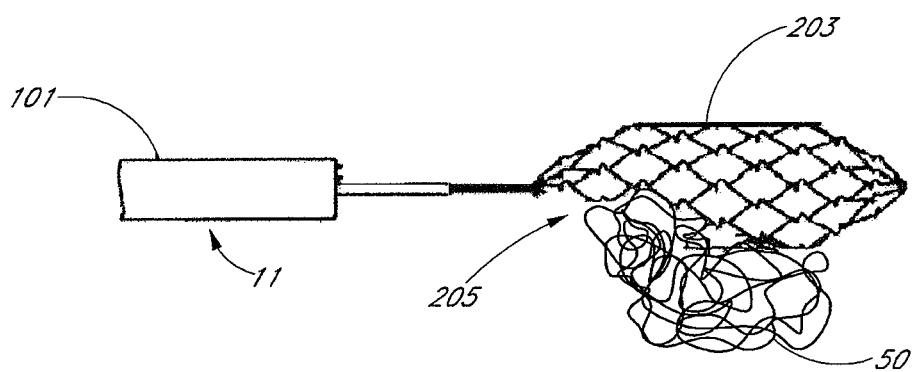
Figure 11:
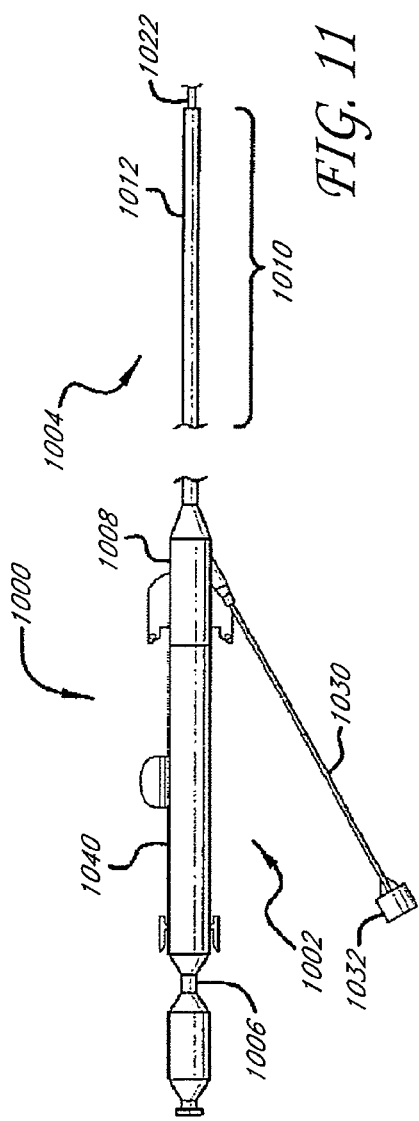
Figure 12:
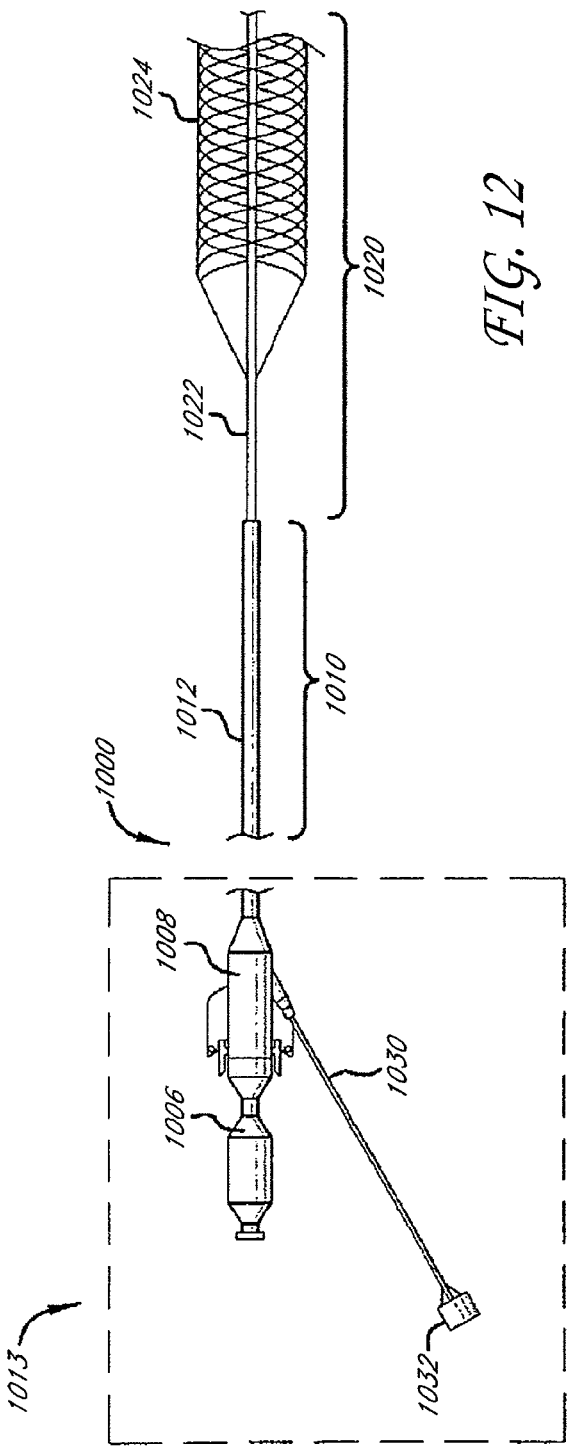
Figure 12A:
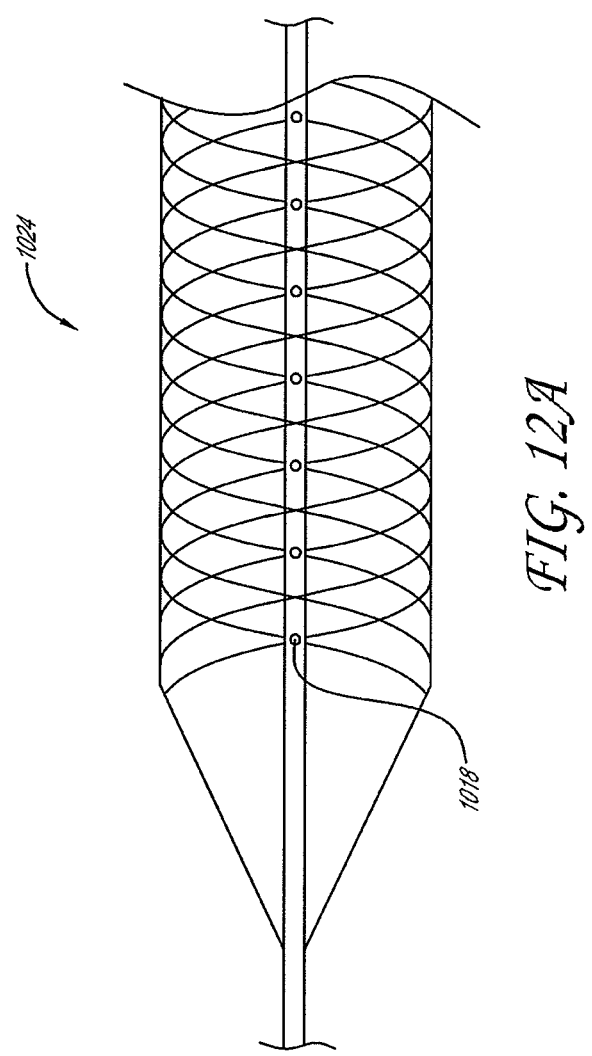
Figure 16A:
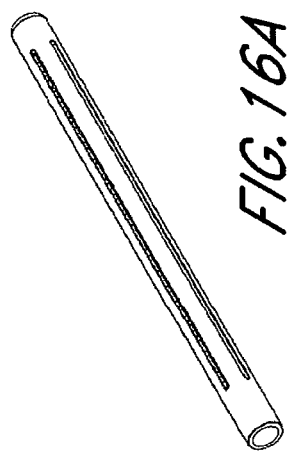
Figure 16B:
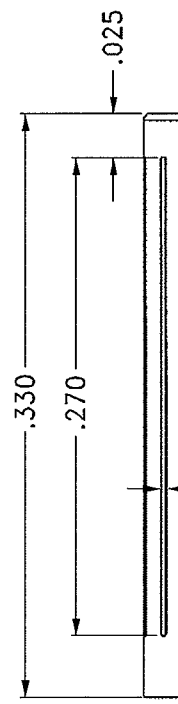
Figure 16C:
Figure 17A:
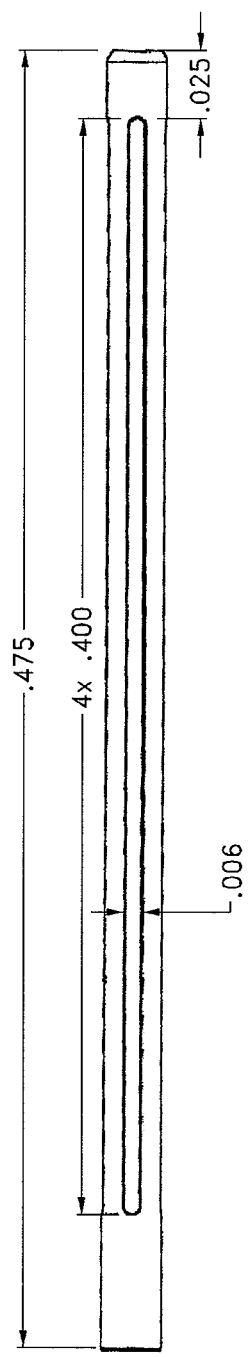
Figure 18A:
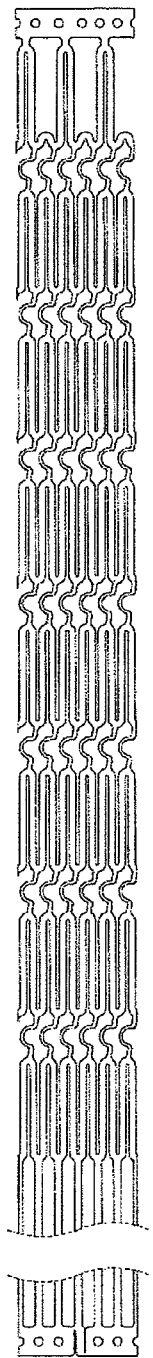
Figure 18B:
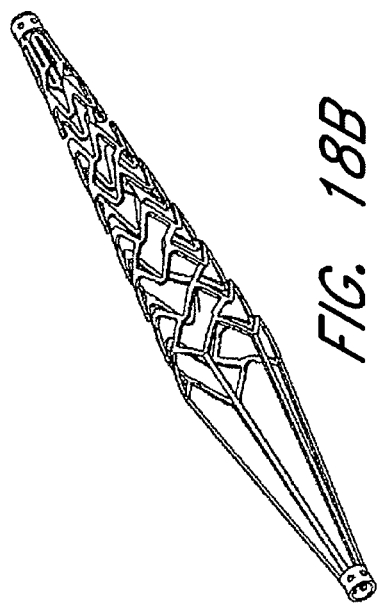
Figure 18C:
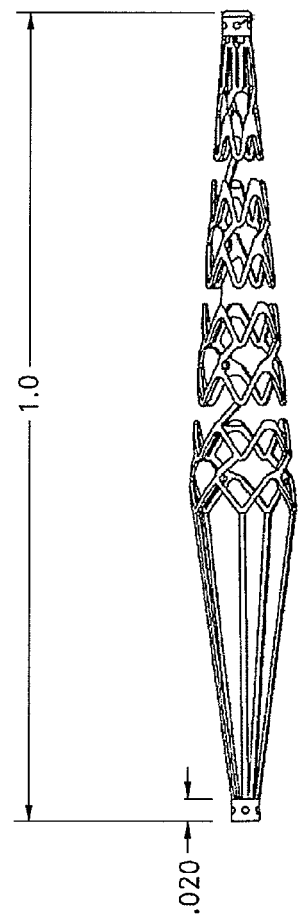
Figure 18D:
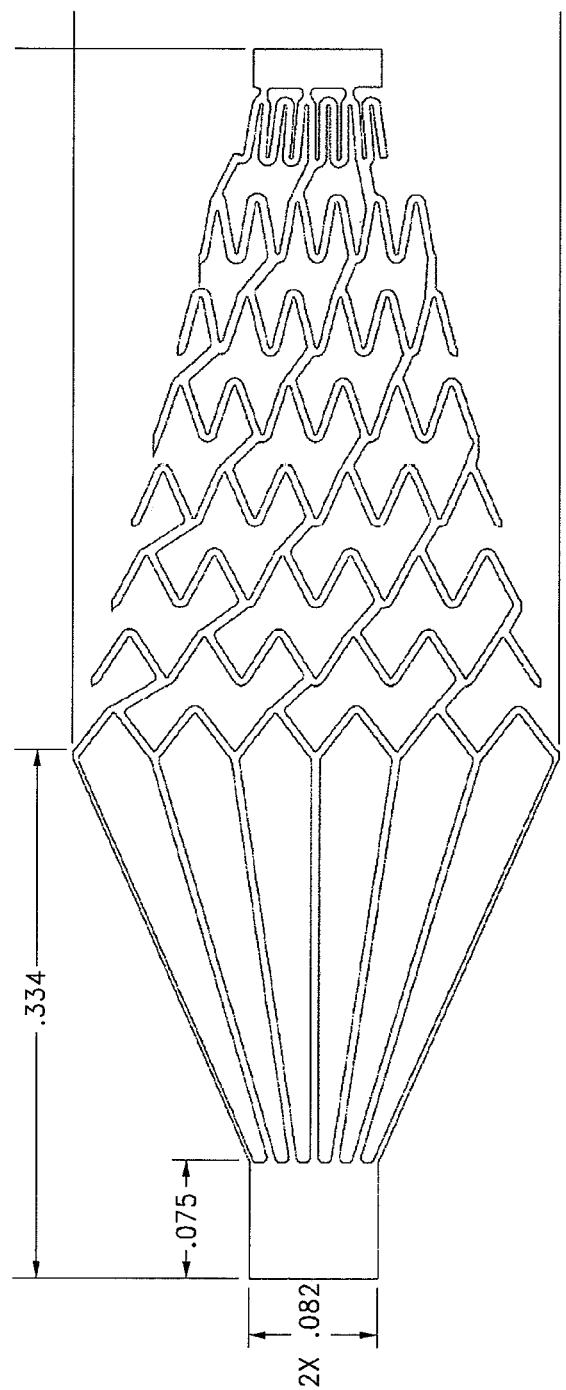
Figure 19A:
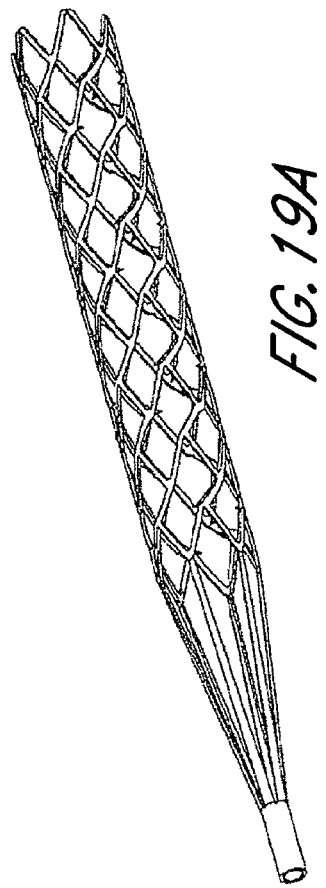
Figure 19B:
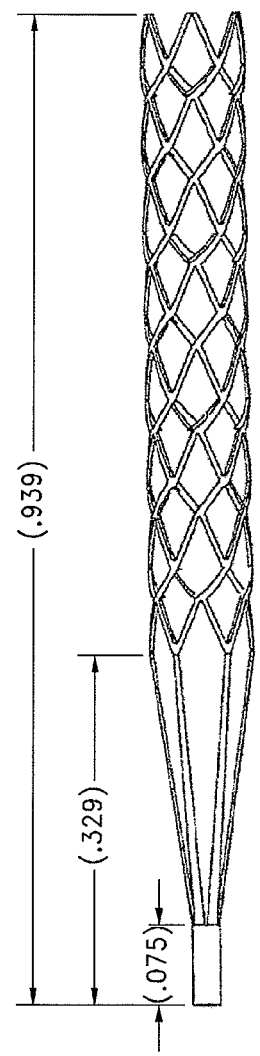
Figure 19C:
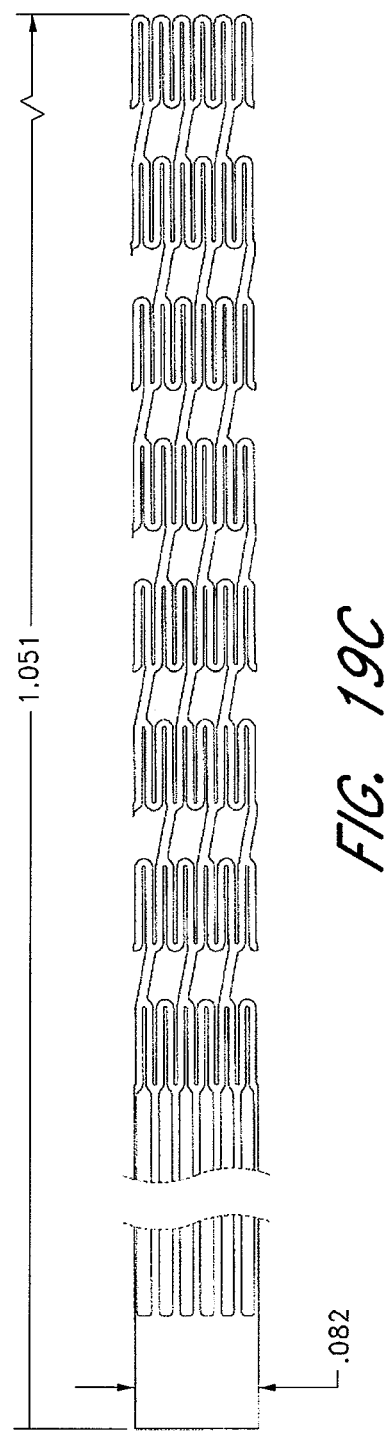
Figure 19D:
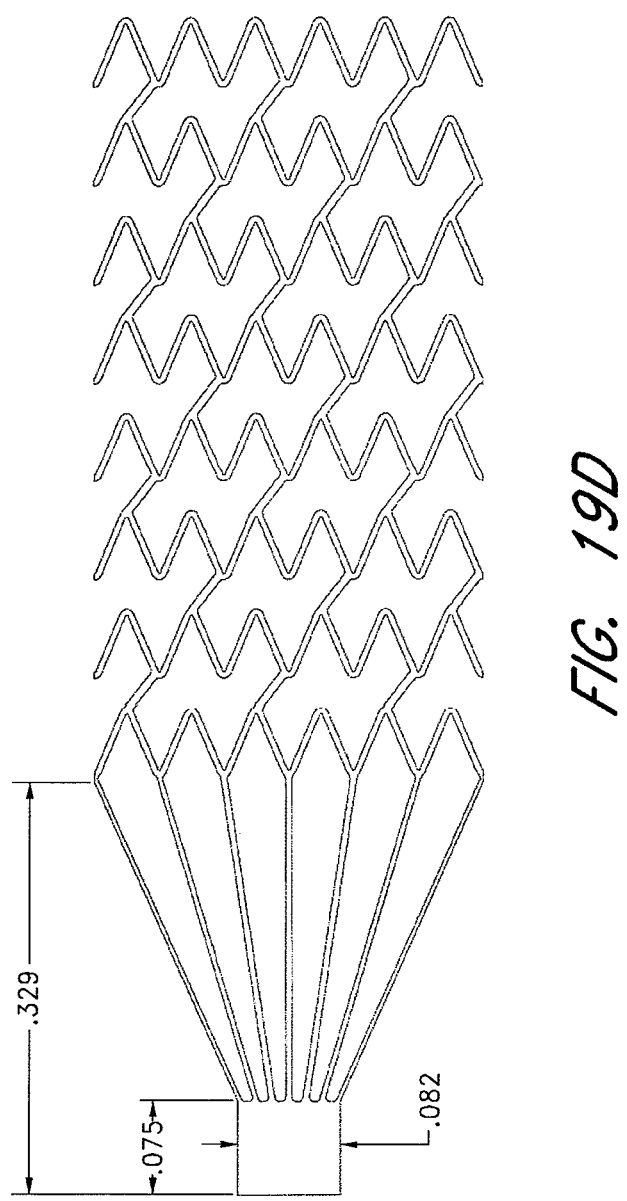
Figure 20A:
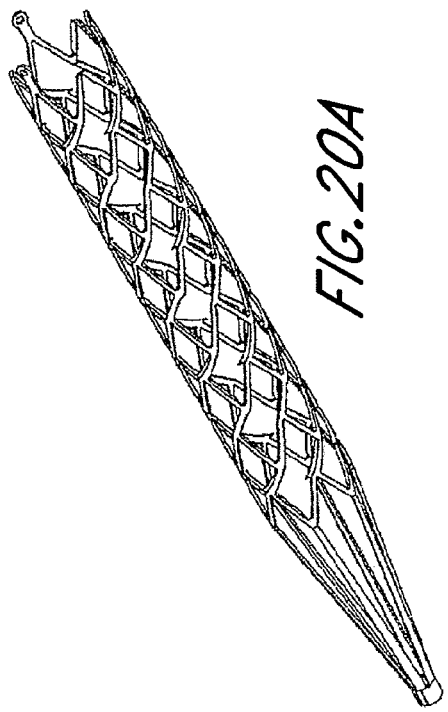
Figure 20B:
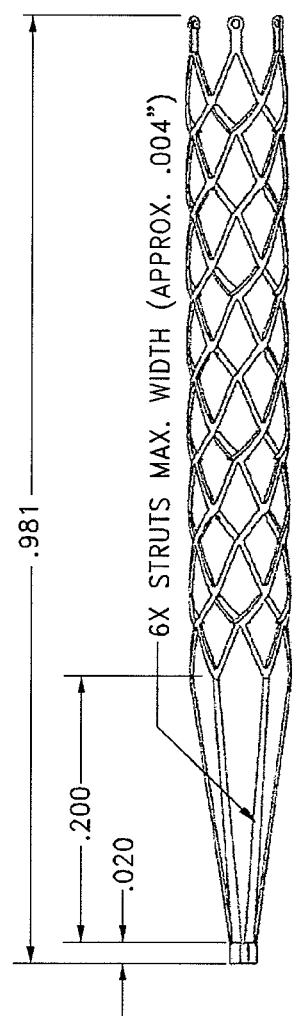
Figure 20C:
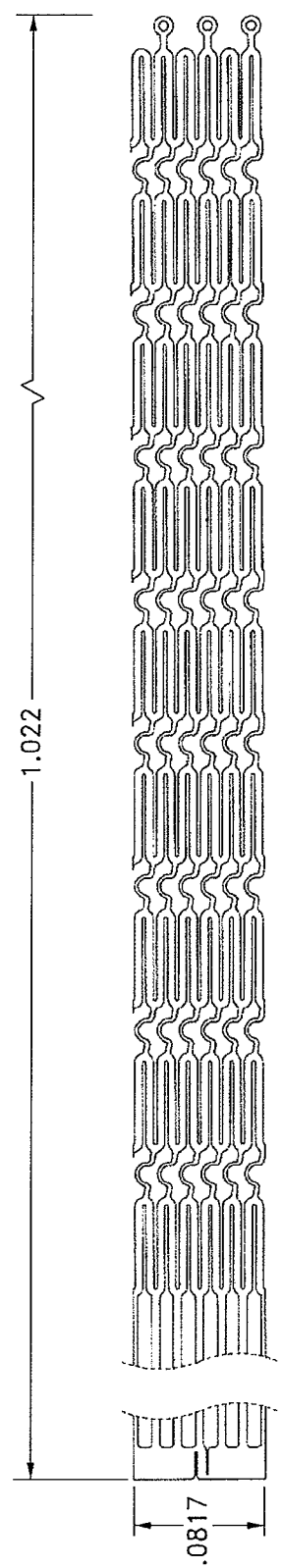
Figure 21A:
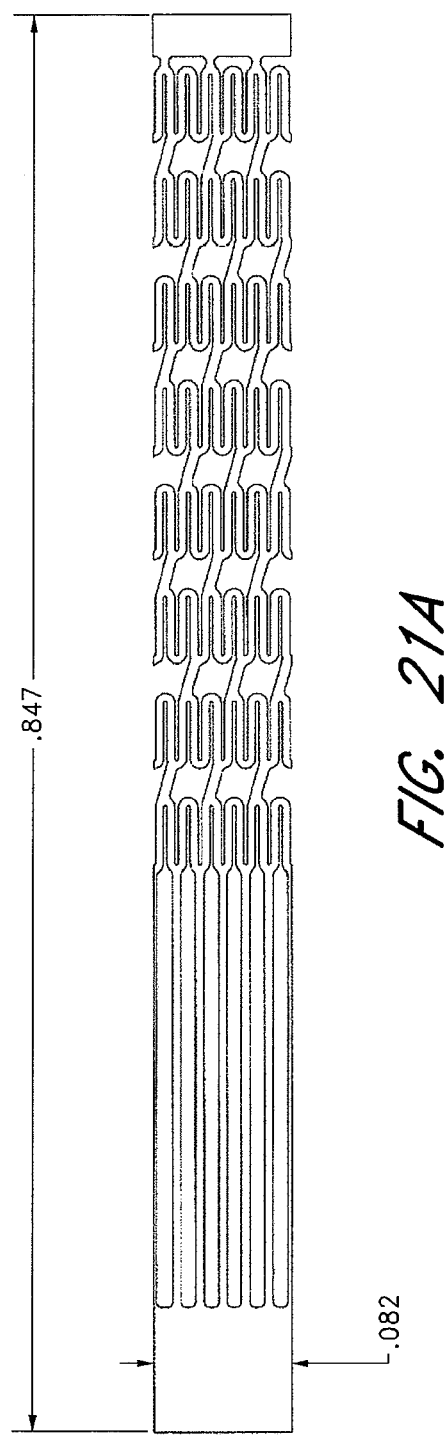
Figure 21B:
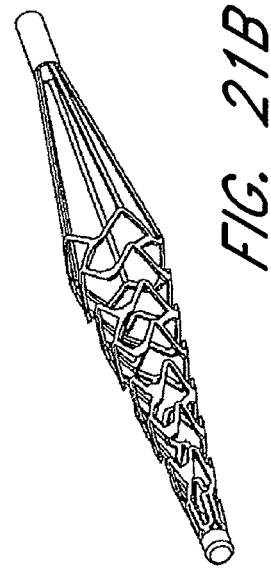
Figure 21C:
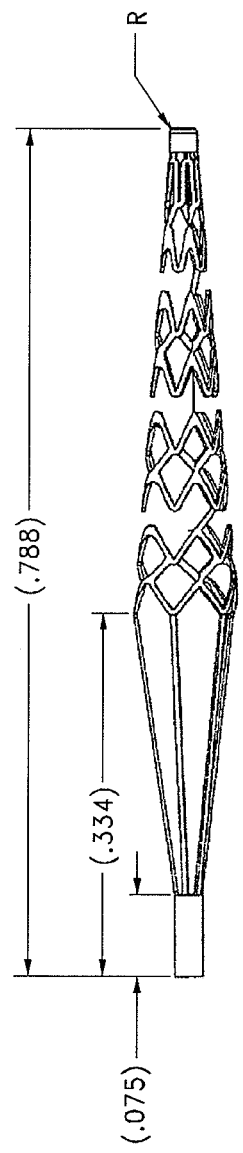
Figure 22:
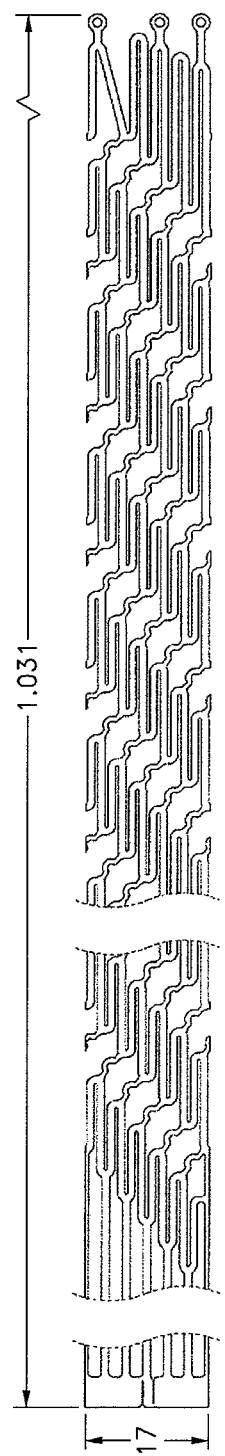
Figure 23:
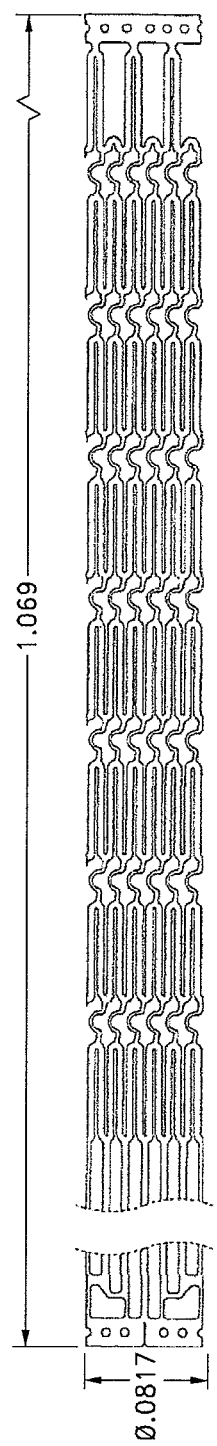
Figure 24A:
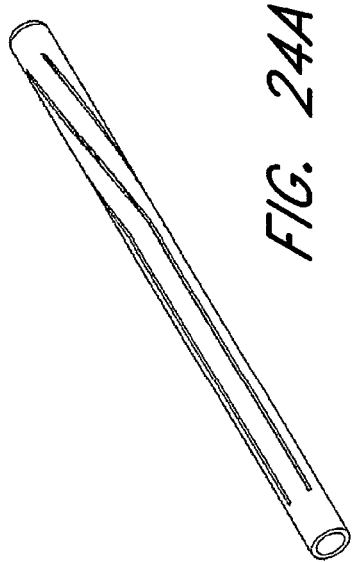
Figure 24B:
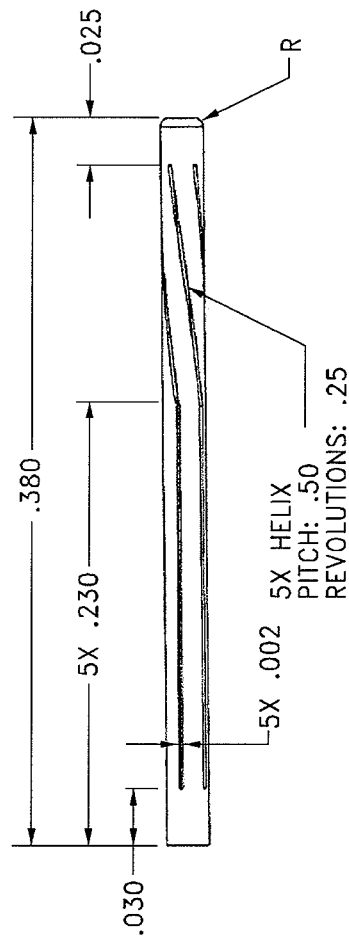
Figure 24C:
Figure 27A:
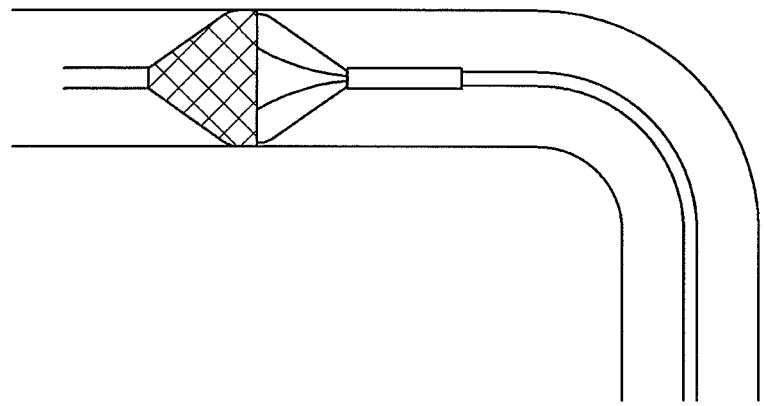
Figure 27B:
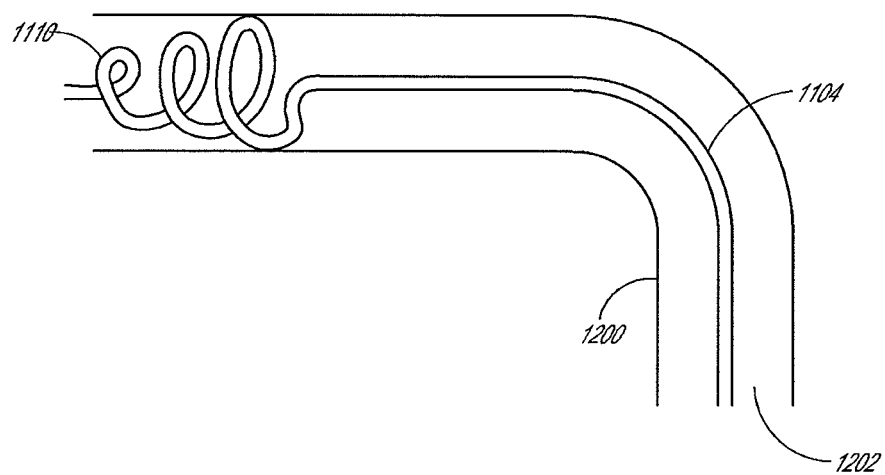
Figure 28A:
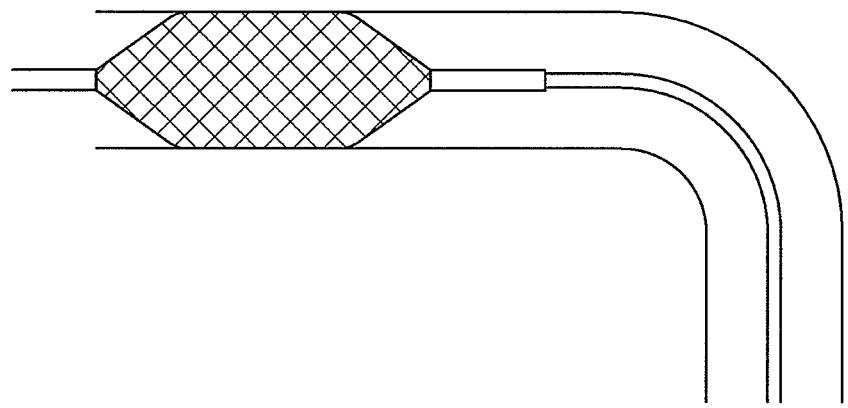
Figure 28B:
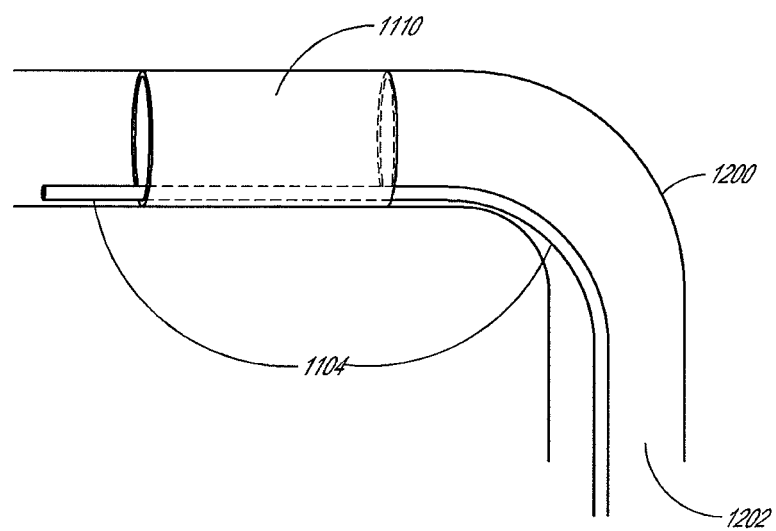
Figure 30B:
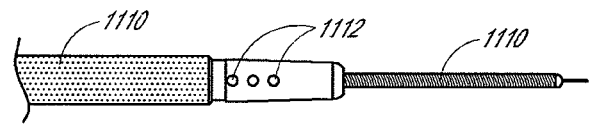
Figure 30A:
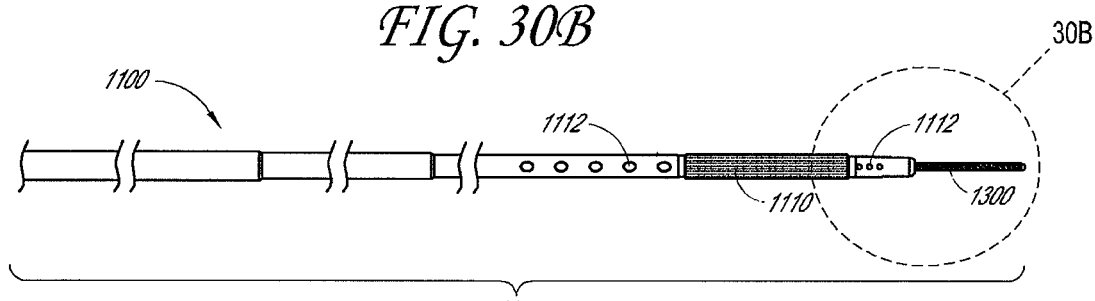
Figure 30D:
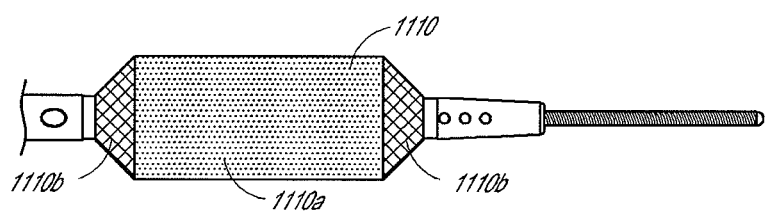
Figure 30C:
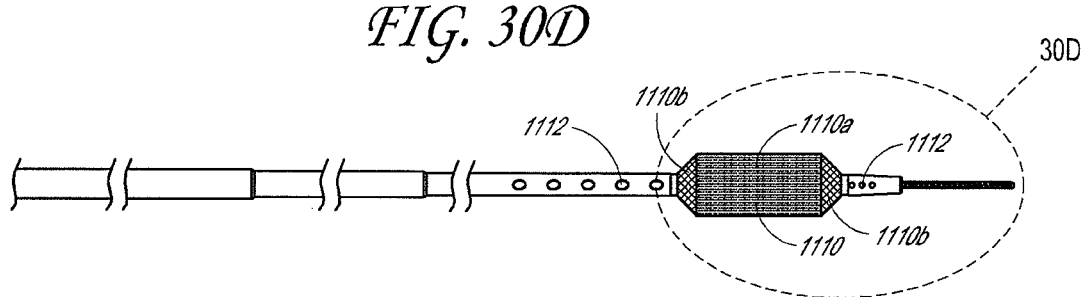
Figure 30E:
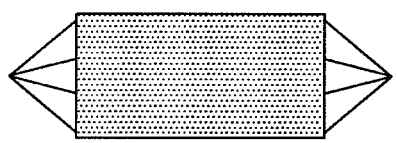
Figure 37A:
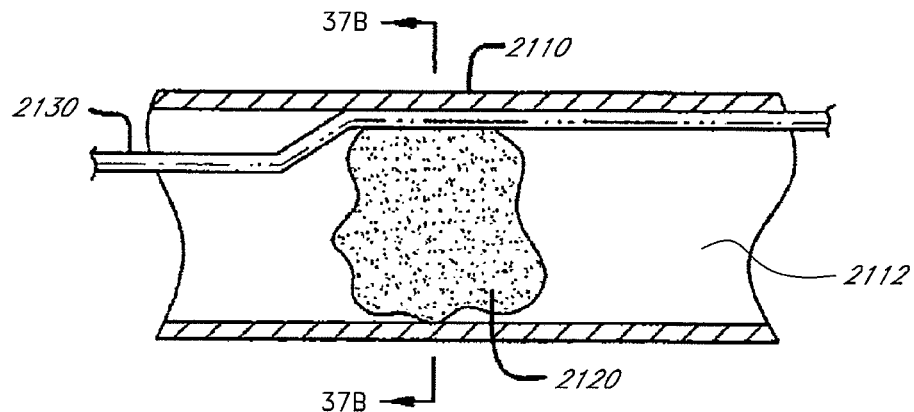
Figure 37B:
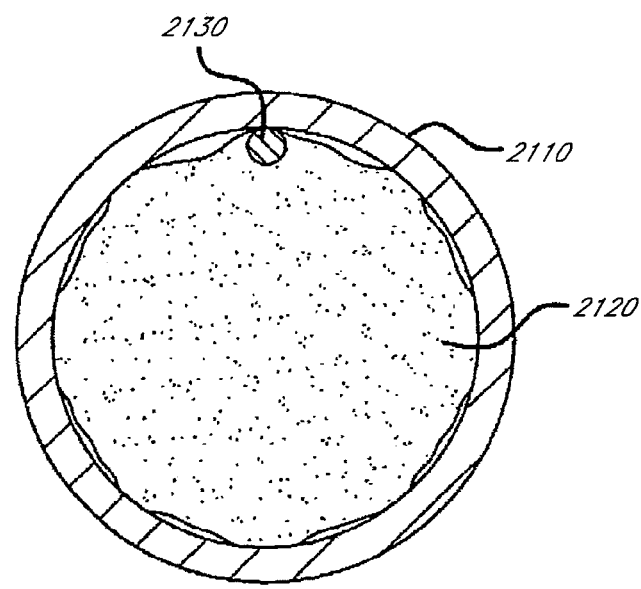
Figure 38:
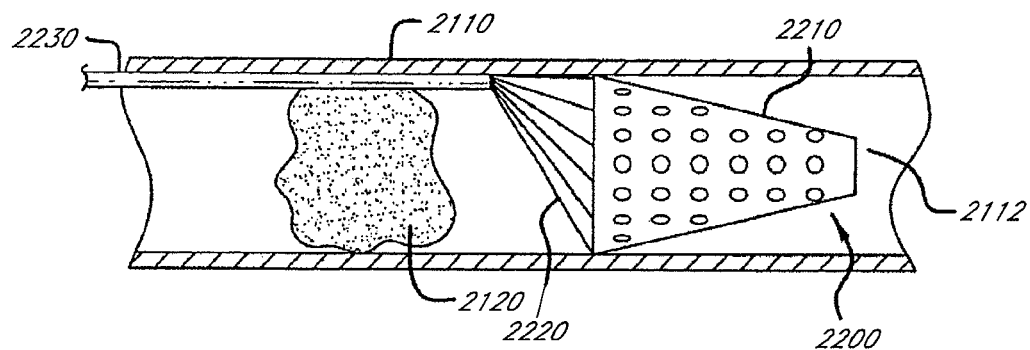
Figure 39:
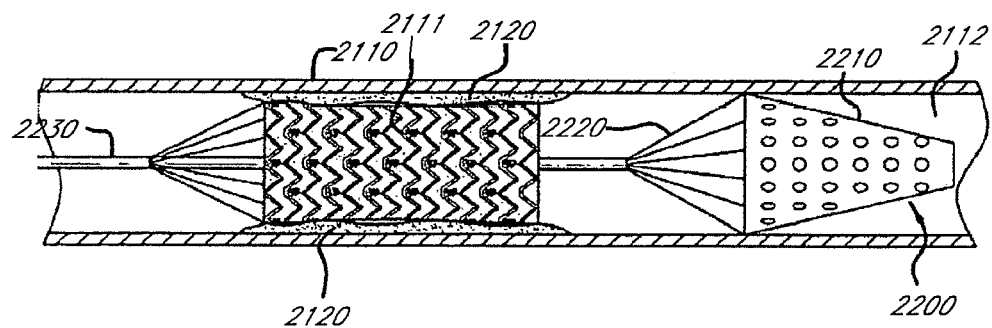
Figure 40:
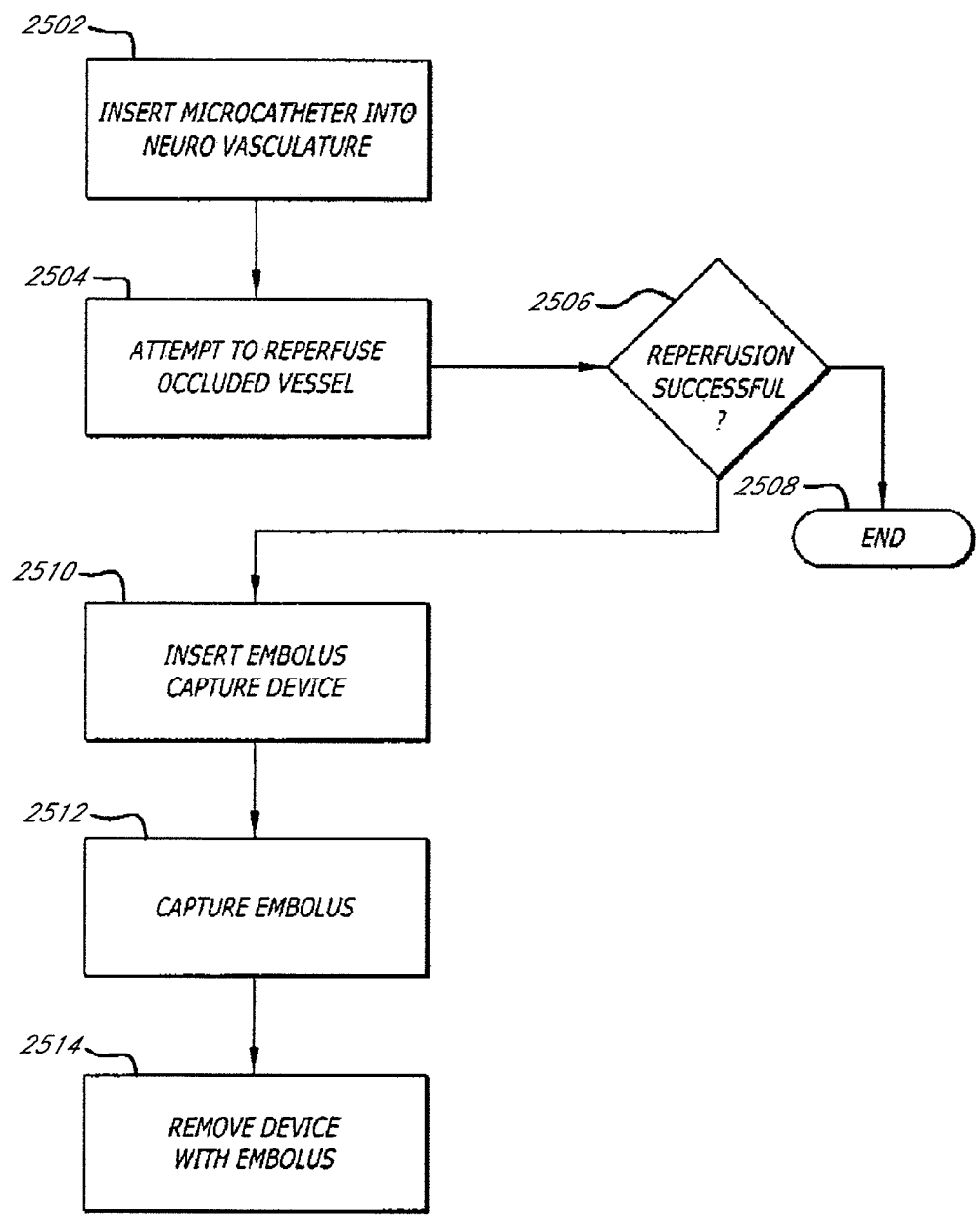
Figure 41:
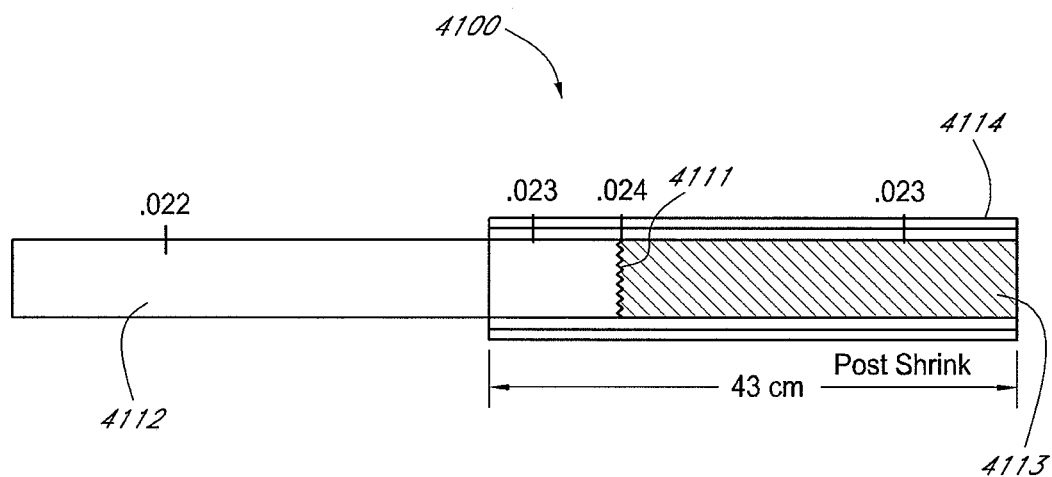
Figure 42:
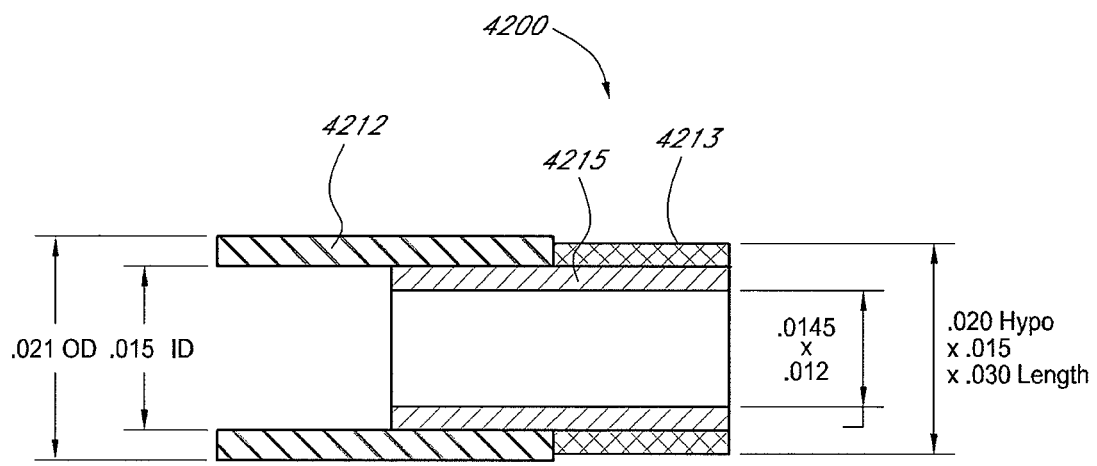
Figure 43A:
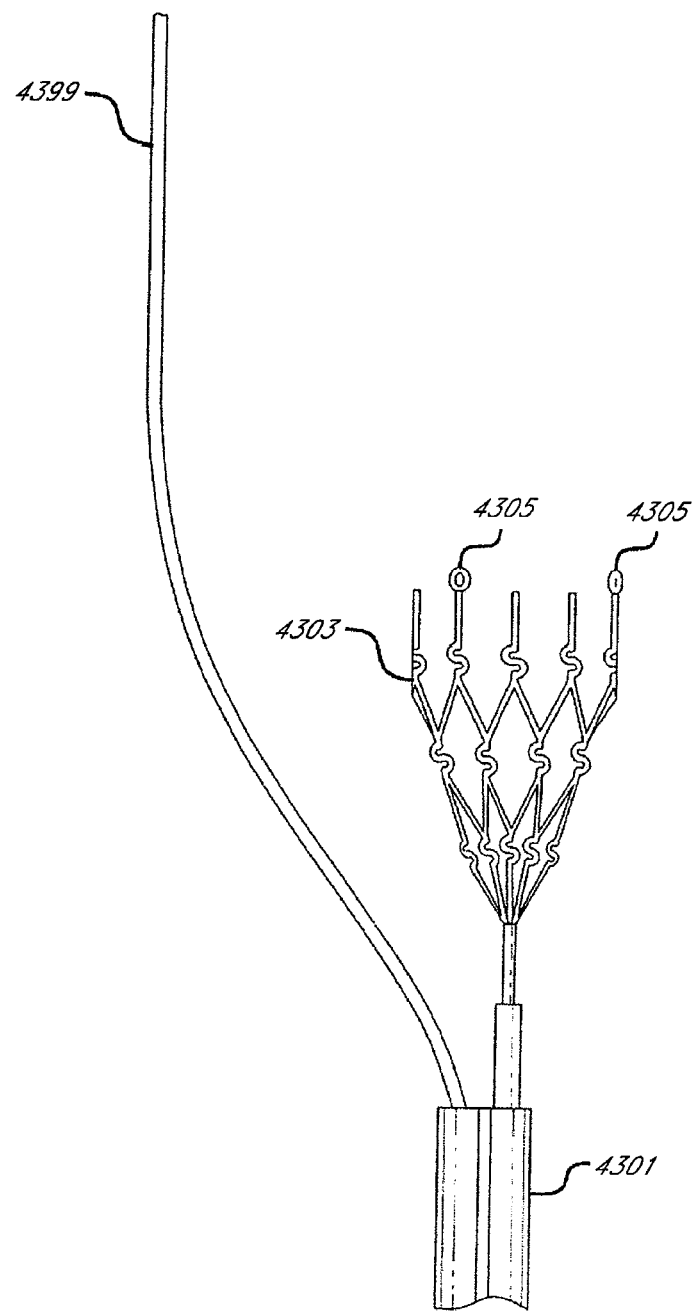
Figure 43B:
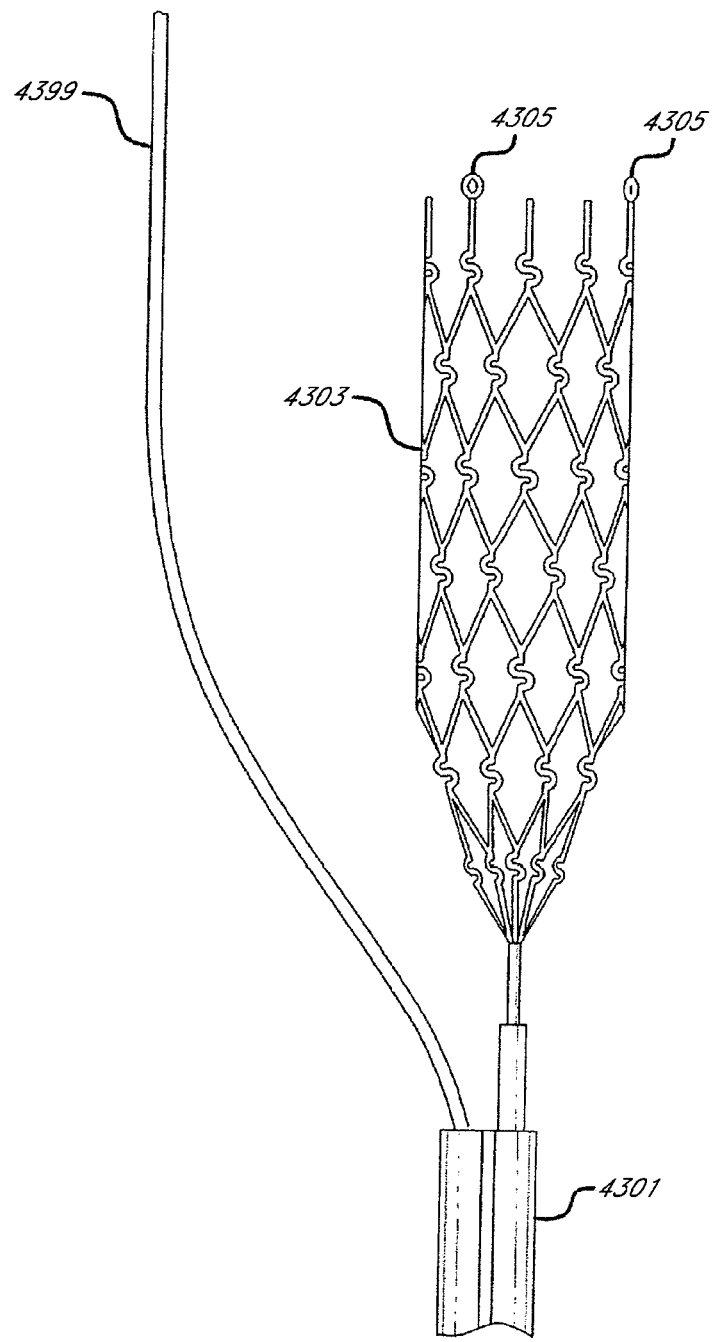
Figure 43C:
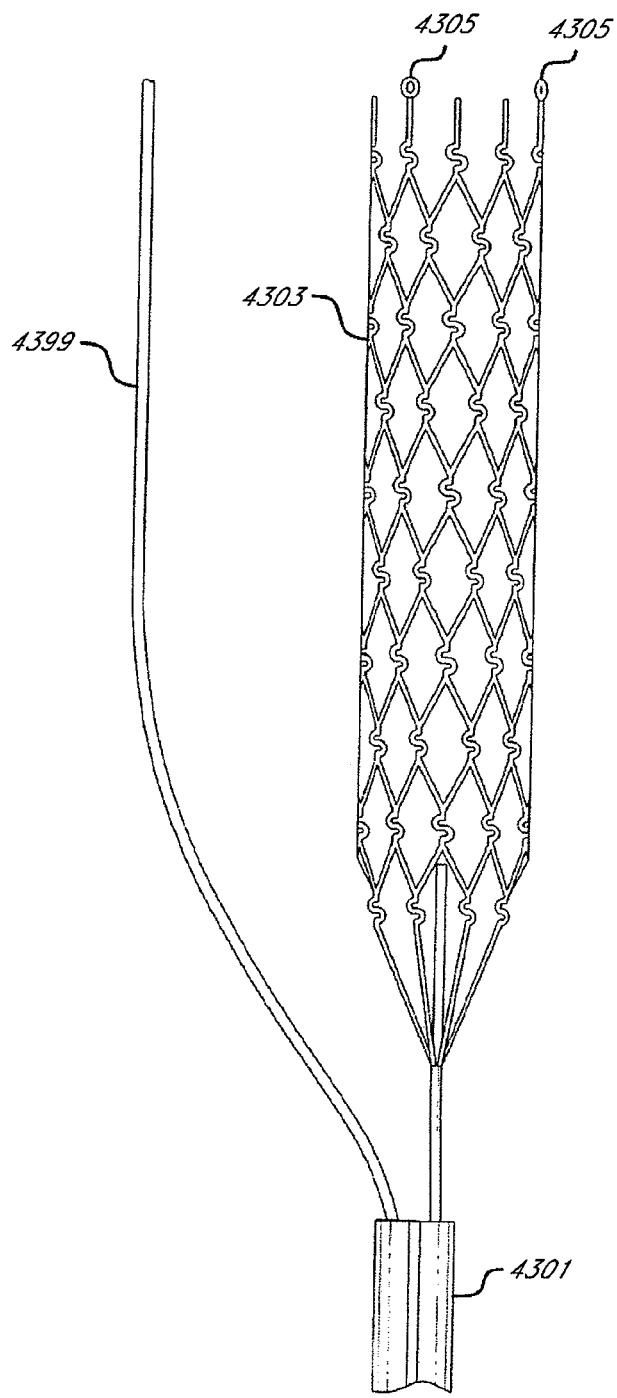

FIG. 9 likewise schematically depicts an exemplary iteration of a device according to the present disclosure in a third position;

FIG. 10 illustrates an embodiment of a device according to the present disclosure;

FIG. 11 is a perspective view of an embodiment of an acute stroke recanalization system according to embodiments of the present disclosure in a first configuration;

FIG. 12 is a perspective view of an embodiment of an acute stroke recanalization system according to embodiments of the present disclosure tailored for use with the neurovasculature in a second configuration, further illustrating modular aspects of the system as used with tethered or reconstrainable self-expanding neurological medical devices;

FIG. 12A illustrates a detailed view of the inner catheter of FIG. 12;

FIGS. 13A-13D illustrate an embodiment of an inner catheter of the acute stroke recanalization system of FIGS. 11 and 12;

FIGS. 14A-14C illustrate a perspective view, a side view, and a front view, respectively, of an embodiment of a self-expanding revascularization device;

FIGS. 15A-15D illustrate an embodiment of a revascularization device configured for eccentric coupling to a pusher;

FIGS. 16A-16F, 17A-17C, 18A-18D, 19A-19D, 20A-20C, 21A-21C, 22, 23, and 24A-24F illustrate various embodiments of revascularization devices;

FIGS. 25A and 25B are perspective views of an embodiment of a rapid reperfusion device of the present disclosure;

FIGS. 26A and 26B are perspective views of an embodiment of a method for use of a rapid reperfusion device of the present disclosure;

FIG. 27A is a side view of an embodiment of a rapid reperfusion device comprising an infusable microwire with an integrated filter;

FIG. 27B is a side view of an embodiment of a rapid reperfusion device comprising an infusable coil;

FIG. 28A is a side view of an embodiment of a rapid reperfusion device comprising an infusable temporary stent;

FIG. 28B is a side view of an embodiment of a rapid reperfusion device comprising an inflatable balloon;

FIGS. 29A and 29B are perspective views of an embodiment of a rapid perfusion device wherein the active segment comprises a radially expandable wire;

FIGS. 30A-30D are perspective views of an embodiment of a rapid perfusion device wherein the active segment comprises a covered or uncovered mesh connected to the microcatheter via tethers;

FIG. 30E is a side view of an embodiment of an active segment comprising an open braid or covered braid configured to be connected to the microcatheter via tethers or an open braid on both the proximal and distal ends;

FIGS. 31A-31D are perspective views of an embodiment of a rapid perfusion device wherein the active segment comprises a radially expanding wire mesh;

FIGS. 32-36 illustrate embodiments of a delivery system and exemplary iteration of a temporary tethered stent mechanism;

FIG. 37A shows a side view schematic of a microcatheter with wire passing an embolus;

FIG. 37B shows a cross-sectional schematic of an embodiment of a microcatheter wire passing by an embolus at a point of least resistance;

FIG. 38 is a side view of an embodiment of a device for capturing emboli according to the present disclosure comprising a basket for capturing the embolus;

FIG. 39 is a side view of an embodiment of a device for capturing emboli according to the present disclosure used as a safety device in a reperfusion operation;

FIG. 40 is a flow diagram of an embodiment of a method wherein an embolus is removed from a patient after a reperfusion operation is unsuccessful;

FIGS. 41 and 42 illustrate embodiments of delivery device assemblies;

FIG. 43A shows a schematic of an exemplary iteration of a device according to the present disclosure in a first position;

FIG. 43B shows a schematic of an exemplary iteration of a device according to the present disclosure in a second position;

FIG. 43C likewise schematically depicts an exemplary iteration of a device according to the present disclosure in a third position; and FIGS. 44-54 illustrate embodiments of a balloon catheter and delivery system.

DETAILED DESCRIPTION

The present inventors have discovered that many of the positives of stenting can be combined with healed revascularization/reperfusion using devices effective to impact and remove embolus. This trend now applies in the brain, and promises dramatic improvements in therapies and treatments.

The pathological course of a blood vessel that is blocked is a gradual progression from reversible ischemia to irreversible infarction (cell death). A stroke is often referred to as a "brain attack" and occurs when a blood vessel in the brain becomes blocked or ruptures. An ischemic stroke occurs when a blood vessel in the brain becomes blocked. Ischemic strokes comprise about 78% of all strokes. A hemorrhagic stroke, which account for the remaining 22% of strokes, occurs when a blood vessel in the brain ruptures. Stroke is the third leading cause of death in the United States, behind heart disease and cancer and is the leading cause of severe, long-term disability. Each year roughly 700,000 Americans experience a new or recurrent stroke. Stroke is the number one cause of inpatient Medicare reimbursement for long-term adult care. Total stroke costs now exceed $45 billion per year in US healthcare dollars.

Viable tissue that surrounds a central core of infarction has consistently been demonstrated in animal models to be salvageable if blood flow can be restored within a time window of several hours. Data from human studies with surrogate measurements of cell viability tended to support this hypothesis. Thus, current treatment strategy for ischemic stroke is based on an urgent restoration of blood flow to the ischemic tissue within the tolerance time window to prevent the permanent loss of brain cells, leading to improved outcome for the patient.

Currently there are only two FDA-approved treatment options for an acute ischemic stroke. One option is an FDA-approved intravenous (IV) delivery of Tissue Plasminogen Activator (t-PA) (Activase), which is a thrombolytic agent. The agent is designed to dissolve the blood clot that is blocking blood flow to the brain. IV t-PA is currently limited in use since it must be used within a 3 hour window from the onset of the stroke and it appears to carry an increased risk of bleeding. The second option is a thromboembolectomy device. In August of 2004, Concentric Medical received FDA approval for its MERCI™ clot removal device. Concentric achieved an approximately 50% success rate in removing clot in its trial. The Merci device is designed to capture an embolus or clot and remove it from the blocked vessel thereby restoring blood flow. The Merci device design is a cork-screwed guidewire. This device is only able to capture and remove matter that is firm or held together by itself. In most cases Merci is used in combination with drug therapy to restore blood flow. A typical procedure using Merci will take 2-3 hours to restore blood flow if at all and may take multiple passes through the vessel to either capture, macerate or open the vessel. In some cases, the Merci device may capture an embolus but then lose grasp of it and deposit it incidentally in another area of the neuro-vasculature creating a new stroke in a new territory. In some cases complications such as vessel dissection, perforation and hemorrhage arise as a result of manipulation in the vessel.

According to the instant disclosure, if autolysis is not occurring then capture of the embolus/blood clot in its entirety without fragmenting the embolus and removal of the embolus/blood clot from the body without creating a new stroke in a new territory is performed.

According to the instant disclosure, the system will allow maintained arterial access to the treatment site and provide greater support to the arterial tree by being either over-the-wire (OTW) or rapid exchange (RX). This feature will enable the embolus/blood clot to be securely captured and removed by providing support within the vessel. The OTW or RX support provided will prevent the proximal vessel from buckling or kinking during tensioning upon embolus removal. Buckling or kinking of the vessel causes the proximal vessel orifice to ovalize, thereby stripping the embolus from the capture device.

In sum, the present inventors have discovered that emboli can be removed while reperfusion is taking place using a variety of devices in the neural space.

Using everted basket-like members and everted stent-like members, emboli can be removed without compromising access, as they become enmeshed with the devices and can be removed without vessel damage.

Those skilled in the art readily understand how the procedure disclosed herein applies to other neuro-vessels. Expressly incorporated by reference, as if fully set forth herein are co-pending and prior pending U.S. application Ser. Nos. 12/123,390, filed May 19, 2008; 60/980,736, filed Oct. 17, 2007; 60/987,384, filed Nov. 12, 2007; 60/989,422, filed Nov. 20, 2007; 61/015,154, filed Dec. 19, 2007; and 61/044,392, filed Apr. 11, 2008; each of which is assigned to MindFrame, Inc.; and U.S. Pat. Nos. 6,306,141; 6,485,500; 5,792,157; 5,972,019; 7,309,351; 7,201,770; 7,179,273; 7,175,607; 7,172,575; 7,160,317; 7,147,655; and 7,004,954.

It shall be understood that the present disclosure may be applied to any object within a blood vessel, including, inter alia, an embolus, a thrombus, a blood clot, a calcified legion, or any other obstruction within a vessel. Reference to any one of these is not limiting in that the device and method may be applied to any of these objects, as well as others.

Figure 1:
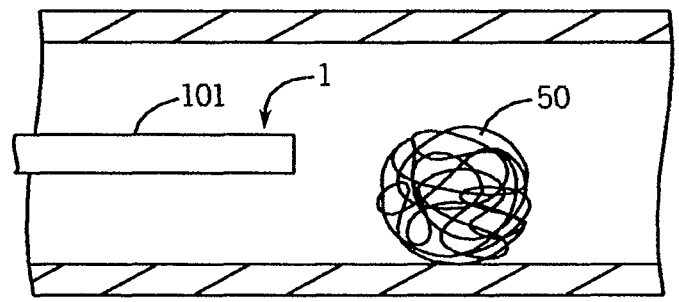
FIG. 1 shows a schematic of an exemplary iteration of a device according to the present disclosure in a position near an embolus.

Referring now to FIGS. 1-6, there is shown a progression of steps whereby an occluded vessel, for example at the MCA/ACA bifurcation, is accessed with a microcatheter 101. According to embodiments, a clot 50 is accessed by a microcatheter 101, as shown in FIG. 1.

Figure 2:
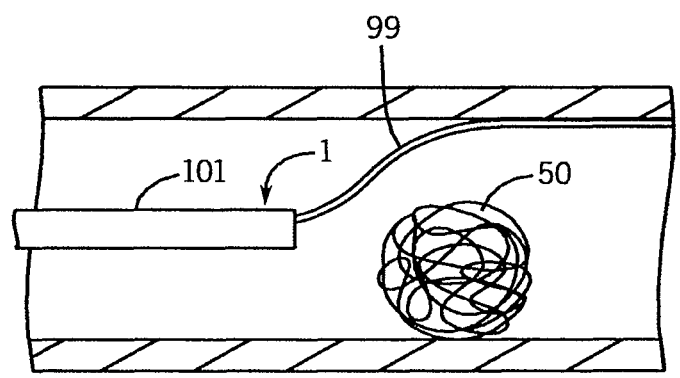
FIG. 2 shows a schematic of an exemplary iteration of a device according to the present disclosure in a position near an embolus with a guidewire deployed.

According to embodiments, a guidewire 99 is deployed from microcatheter 101. The guidewire may be deployed so as to cross the clot 50, as shown in FIG. 2. Where clot 50 may occupy a substantial portion of the vessel, the guidewire 99 may pass around or through the clot 50.

Figure 3:
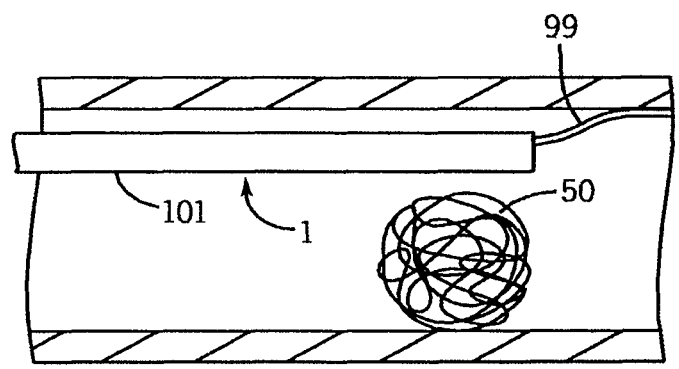
FIG. 3 shows a schematic of an exemplary iteration of a device according to the present disclosure in a position bridging an embolus.

According to embodiments, microcatheter 101 is deployed to cross at least a portion of a clot 50. Microcatheter 101 may be guided by guidewire 99, as shown in FIG. 3, or may cross at least a portion of clot 50 without the aid of guidewire 99.

Figure 4:
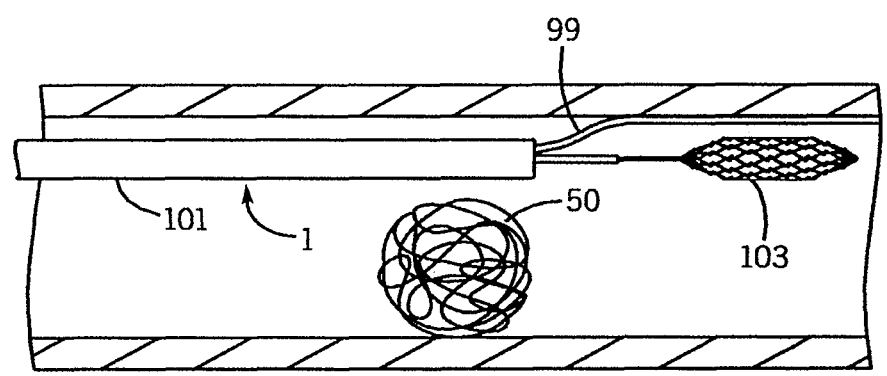
FIG. 4 shows a schematic of an exemplary iteration of a device according to the present disclosure with a capturing device being deployed.

According to embodiments, a capturing device 103 is deployed from a lumen of a microcatheter 101. First, a portion of capturing device 103 may be deployed as microcatheter 101 is retracted, as shown in FIG. 4. As the capturing device 103 is deployed, reperfusion of the vessel in the vicinity of the clot 50 may be restored at least somewhat.

Figure 5:
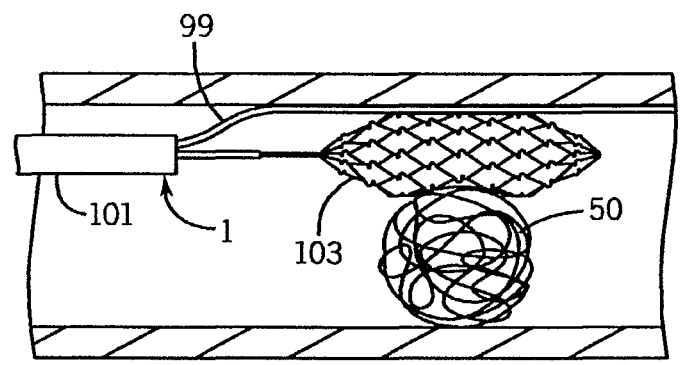
FIG. 5 shows a schematic of an exemplary iteration of a device according to the present disclosure with a capturing device bridging an embolus.

According to embodiments, as a capturing device 103 is deployed from a microcatheter 101, the capturing device 103 may expand against a clot 50, as shown in FIG. 5. The amount of expansion may depend on the amount of capturing device 103 that is deployed from the microcatheter 101. Expansion may also hold the clot 50 against a wall of the vessel, such that it is not displaced while the procedure is being performed. Capturing device 103 may be manipulated and oriented to align such that acceptance of the clot 50 within capturing device 103 is facilitated.

Figure 6:
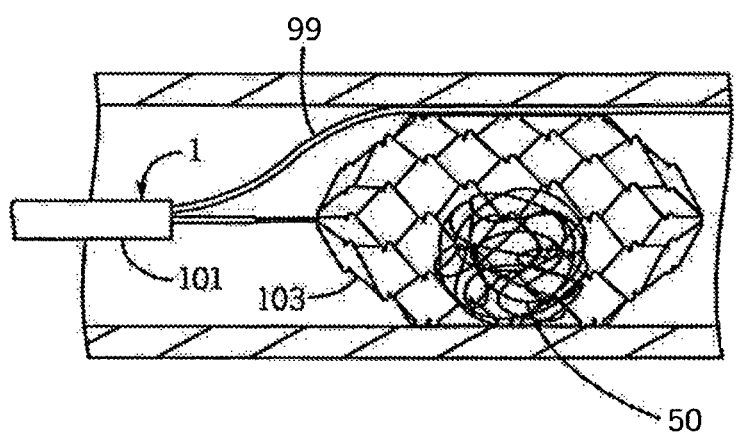
FIG. 6 shows a schematic of an exemplary iteration of a device according to the present disclosure with an embolus within a capturing device.

According to embodiments, the expansion of a capturing device 103 causes a clot 50 to be within the boundaries of the capturing device 103, as shown in FIG. 6. The clot 50 may enter the capturing device 103 through a mouth 105, through the natural open-cell structure of a mesh netting that contributes to the structure of capturing device 103, or through an everted section on either one of the proximal end or the distal end of the capturing device 103.

According to embodiments, at least the capturing device 103 is retracted to remove a clot 50 captured within the capturing device 103 from the vessel. For example, the clot 50 may be slowly pulled back until it can be drawn into the carotid siphon, then removed into the cavernous carotid, then the common carotid, and eventually removed from the body. Capturing device 103 may be manipulated to maintain the clot 50 within the capturing device 103. For example, capturing device 103 may be rotated, retracted, or constrained such that clot 50 does not exit from capturing device 103, such as through a mouth 105 or other openings of capturing device 103 until desired.

According to embodiments, an extraction device 1 is disclosed, comprising a microcatheter 101 and a capturing device 103, which may be disposed within a lumen of the microcatheter 101. Capturing device 103 may include at least one device selected from the group of everted, stent-like members, basket-like clot removal devices having everted distal tips, and hybrid devices of the first two types.

Figure 7:
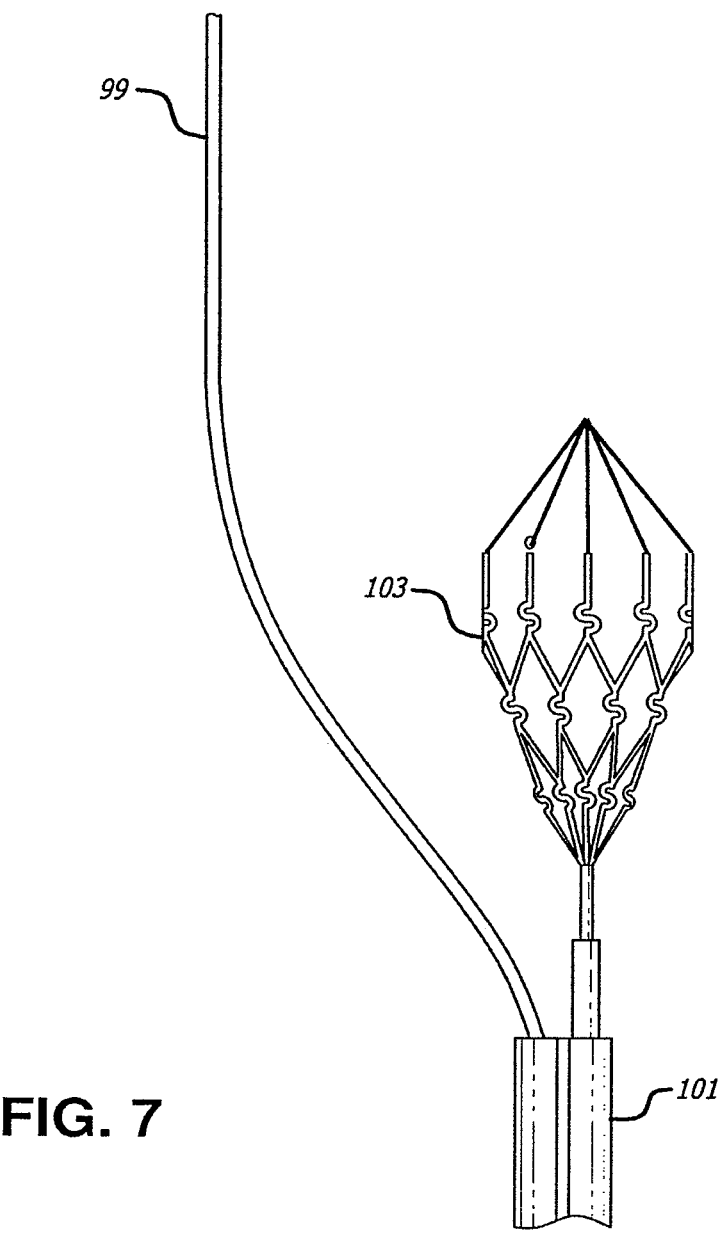
FIG. 7 shows a schematic of an exemplary iteration of a device according to the present disclosure in a first position.
Figure 8:
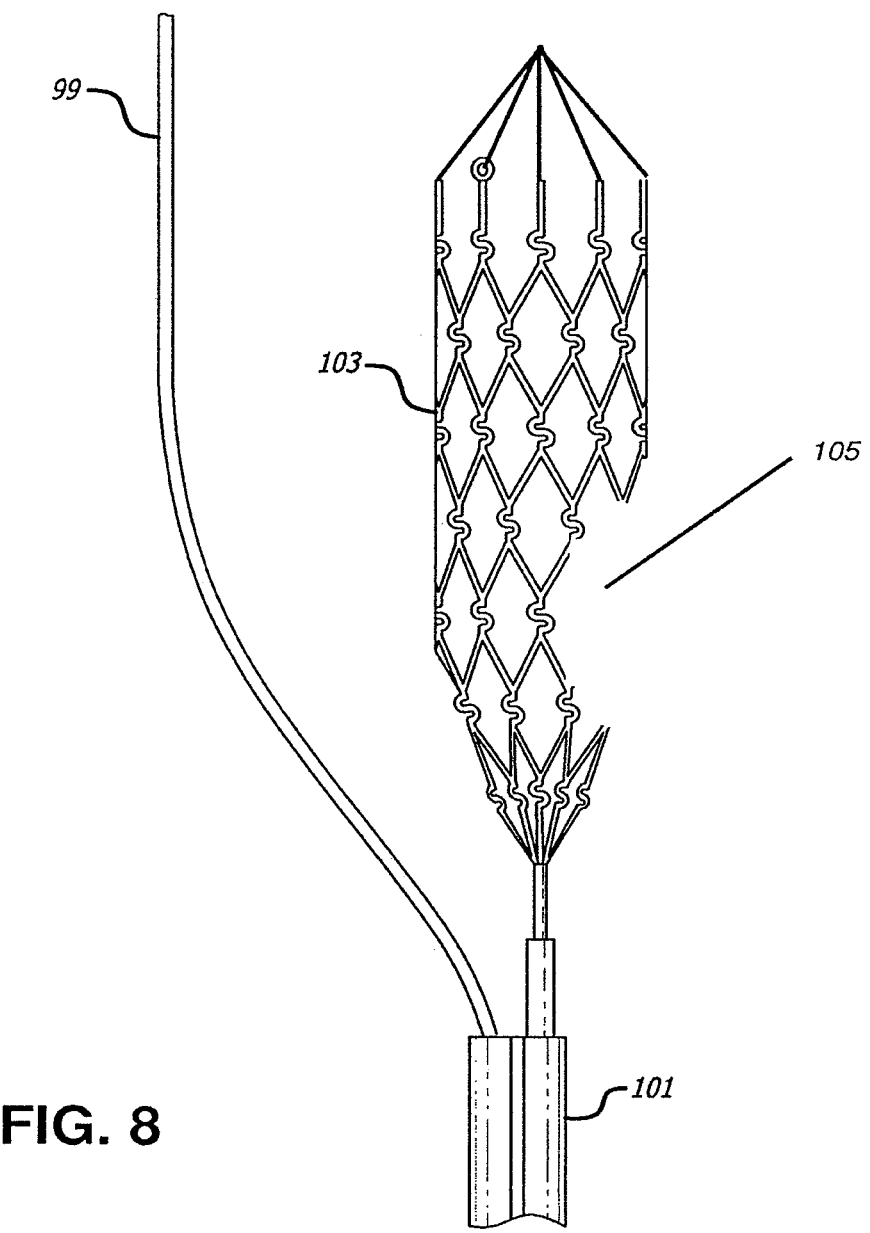
FIG. 8 shows a schematic of an exemplary iteration of a device according to the present disclosure in a second position.

Referring to FIGS. 7-8, according to embodiments of the present disclosure, guidewire 99 accesses and crosses a target lesion, providing a pathway for microcatheter 101. Capturing device 103 is shown in a state of transition from a first (collapsed) position to a second (expanded) position emerging from a lumen of microcatheter 101. According to embodiments, guidewire 99 may be at least partially disposed within a lumen of microcatheter 101. According to embodiments of the present disclosure, capturing device 103 may include radiographic marking elements for visualization during placement.

Referring also to FIG. 9, according to embodiments of the present disclosure, capturing device 103 is shown in a fully expanded position, whereby it functions consistently and safely such that arterial support is maintained in virtue of guidewire 99 keeping the arterial tree from mechanical stress, while embolus removal, clot capture and other procedures are done. Thus, reperfusion is established and therapy administered without risks to patients present with other devices. According to embodiments, capturing device 103 is self-expandable, such that it may expand substantially radially when removed from within the catheter. According to embodiments, additional therapies may be provided while capturing device 103 is fully expanded, for example, through another lumen of microcatheter 101.

According to embodiments, capturing device 103 may include a portion to allow passage of a clot 50 from the exterior of the capturing device 103 to the interior of the capturing device 103. A clot 50 may be accepted into capturing device 103 by a mouth 105, the natural open-cell structure of a regularly woven mesh capturing device 103, or an everted section on either one of the proximal end or the distal end of the capturing device 103. A portion to accept a clot 50 may be disposed at a distal or proximal end the capturing device 103 or along the length of capturing device 103.

According to embodiments, capturing device 103 may include a distal portion that is resistant to the passage of a clot 50 from the interior of the capturing device 103 to the exterior of the capturing device 103. A closed distal end may prohibit the escape of a clot 50 out of the distal end while the capturing device 103 is retracted. For example, as shown in FIGS. 7-9, the distal end of the capturing device 103 may be closed, such that the open-cell structure at the distal end is more confined than the open-cell structure at the middle section of capturing device 103, mouth 105, or other section to accept a clot 50. Other geometries and structures are contemplated, including nets, filters, and membranes. According to embodiments, the distal end of capturing device 103 facilitates perfusion of the vessel.

As excerpted from U.S. Provisional No. 61/057,613, which is incorporated herein by reference, FIG. 10 illustrates an embolus 50 caught on an external distal tip of an embodiment of an extraction device 11 comprising a microcatheter 101 and a reperfusion/clot removal device 203. The reperfusion/clot removal device 203 has an open "mouth" 205. The mouth 205 spans from a proximal tip of the reperfusion/clot removal device 203 to approximately a mid-section of the reperfusion/clot removal device 203. The clot, or embolus, 50 appears to be partially caught in the mouth 205 of the reperfusion/clot removal device 203 but partially on the external surface of the distal basket region of the reperfusion/clot removal device 203. In some embodiments, the clot 50 decreases in size (e.g., a diameter and/or length of the clot 50) from use of the reperfusion/clot removal device. In one embodiment, the size of the clot, or embolus, 50 is decreased from 4-5 mm in diameter and 15 mm in length to 4 mm in diameter and 10 mm in length.

In one embodiment, an occluded artery, for example, at the MCA/ACA bifurcation is accessed with a microcatheter, then a clot is accessed using the subject reperfusion/clot removal device, allowing for reperfusion by the reperfusion/clot removal device.

In one embodiment, the reperfusion/clot removal device engages the clot by impacting the same. The nature of the open-cell structure of the device grabs the clot, which is then slowly pulled back until it can be drawn into the carotid siphon and then removed into the cavernous carotid, then the common carotid and eventually removed from the body.

EXAMPLE 1

Clotting Characteristics of Swine Blood for Testing Purposes

A study was performed to evaluate swine blood for clotting characteristics under certain handling conditions. The materials used in the test included: (1) 1 liter of pig blood (no anti-coagulant), (2) Pyrex® glassware, (3) Clorox® bleach, (4) syringes, and (5) saline consisting of a multi-purpose no rub isotonic solution, (In accordance with one embodiment, the testing procedure was performed as follows: (1) pour pig blood into glassware, (2) allow pig blood to sit for 90 minutes, (3) wash the pig blood with saline, (4) allow to sit for 60 minutes, (5) remove "white" clot with cutting tools, (6) wash thoroughly with saline, and (7) measure clot dimensions. The dimensions of the clot removed from the pig blood had a length of 50 mm and a diameter ranging from 7 to 10 mm. Other disclosure can be found in U.S. Provisional No. 61/057,613, which is expressly incorporated herein by reference.

According to embodiments, a kit of parts is disclosed, comprising an extraction device 1, as described herein, and directions for use. According to embodiments, the kit of parts and/or its components may be included as part of a surgical tray.

As excerpted from U.S. Provisional No. 60/980,736, filed Oct. 17, 2007 and from U.S. application Ser. No. 12/123,390, filed May 19, 2008, which are incorporated herein by reference, FIGS. 11, 12, 12A, 13A-13D, 14A-14C, 15A-15D, 16A-16F, 17A-17C, 18A-18D, 19A-19D, 20A-20C, 21A-21C, 22, 23, and 24A-24F illustrate embodiments of revascularization devices.

According to embodiments, by leveraging a conventional self-expanding revascularization device delivery platform, a poly-modic system can be iterated which impacts, addresses and/or crosses an embolus, radially filters, and either removes the offending embolus or is optionally emplaced to address the same. A paucity of extant systems effective for such combination therapies is noted among the art.

Using endovascular techniques self-expandable tethered or reconstrainable self-expanding neurological medical devices offer instant revascularization/recanalization of MCAs and related vessels, without any of the traditional concerns associated with stenting, according to embodiments.

The catheter-based revascularization system disclosed herein allows for natural lysis, revascularization of the challenged vessels, and importantly radially filters any particulates generated, to obviate the need to be concerned with distal migration of the same, unlike prior systems or applications which include largely "off-label" usages of devices approved only for aneurysms in the brain.

The present disclosure relates to revascularization devices (e.g., reperfusion devices) used to treat, among other things, ischemic stroke. Naturally, therefore, the revascularization devices of the present disclosure are designed to be used in neuro-type applications, wherein the specifications of the present catheters and revascularization devices may be deployed in the blood vessels of the cerebral vascular system. Similarly contemplated for the revascularization systems and catheters of the present disclosure is deployment in other parts of the body wherein the specifications of the present disclosure may be used in other vessels of the body in a non-invasive manner.

According to embodiments, disclosed herein is a catheter-based revascularization system. The revascularization devices of the present disclosure are for revascularization of blood vessels. When the catheter-based revascularization system of the present disclosure is deployed into a blood vessel having an embolus, the revascularization device is expanded thereby opening the vessel so that the vessel can resume proper blood flow.

According to the instant teachings, deployment of the system of the present disclosure, establishes immediate 50% of the diameter of the lumen patency of the vessel being addressed. Among the prior art, no system having adequately small profile with flexibility to promote improved access for in-site treatment is known which may be used as a temporary (not implanted) solution. Those skilled in the art readily understand that detachment methods comprising mechanical, electrical, hydraulic, chemical, or thermal, and others are within the scope of the instant teachings.

Moreover, as the embolus dissolves, either via blood flow or by infusing lytic agents than the guidewire lumen, the deployed revascularization device radially filters larger embolus particles from traveling downstream, thereby reducing the chances of further complications. Once the blood vessel is revascularized, the revascularization device is modified to be in a removable state together with filtered detritus, and the catheter-revascularization system is removed from the blood vessels of the patient.

Likewise, in the event that no resolution of the embolus is noted in the instant revascularization system the inventors contemplate detachment and employment as a stent of the cage-like membrane. Angiographic recanalization has been associated with improvement in clinical outcome in the setting of acute stroke resulting from acute intracranial thrombotic occlusion. Anatomic limitations (tortuous anatomy, length of the occlusion, or location of occlusion) or supply limitations are among the reasons precluding use of prior art systems until the advent of the instant teachings.

Stenting has been used successfully to restore flow after abrupt reocclusion occurring after recanalization with other modalities in previous cases. Stenting has also been reported in cases in which other modalities have failed to recanalize vessels. Even if an underlying stenosis is rarely the cause of stroke, stenting may play a role by morselizing the embolic clot or trapping it against the arterial wall. In several embodiments, an acute stroke revascularization process comprises providing a reconstrainable self-expanding microstent system, deploying a self-expanding microstent within a neurological vessel; achieving at least one of revascularization and recanalization of a subject vessel; and removing the self-expanding microstent. In some embodiments, at least one supplemental therapy is also provided, and comprises one or more of the following: pharmacological thrombolytic agents, intraarterial thrombolytics, and mechanical manipulation.

The use of intracranial stents as a method for arterial recanalization during cerebral ischemia caused by focal occlusion of an intracranial vessel has been demonstrated to have benefits in some cases. Despite the use of available pharmacological and mechanical therapies, angiographic recanalization of occluded vessels has not been adequately achieved before stent placement, in most cases.

When SAH and intracranial hematoma occurred in patients in whom balloon-mounted stents were used, they most likely resulted from distal wire perforation. The distal wire purchase needed to navigate a coronary stent into the intracranial circulation may explain the occurrence of these adverse events. Alternatively, multiple manipulations of the Merci® brand of retriever device or expansion of balloon-mounted stents may have induced microdissections in the vessel. Stents designed for intracranial navigation have better navigability and pliability. The Wingspan® brand of stent (Boston Scientific) was designed to have more radial force than the Neuroform® brand of stent and may further improve this technique. However, the act clearly needs to advance further in this area.

IA therapy for stroke has evolved during the past decade. Approval of the Merci® brand of retriever device represents a significant step toward achieving better outcomes in acute stroke for patients not suitable for IV t-PA. However, recanalization is not always achieved using this device. Therefore, additional treatment options are required, as offered for consideration herein.

Spontaneous dissection of the internal carotid artery (ICA) is one of the main causes of ischemic stroke in young and middle-aged patients, representing 10% to 25% of such cases. Because infarct due to dissection is mainly thromboembolic, anticoagulation has been recommended to prevent new stroke in patients with acute dissection, provided they have no contraindications. In the acute phase, intravenous recombinant tissue-type plasminogen activator (IV rtPA) given within 3 hours after onset of stroke due to dissection is reportedly safe and effective. However, this often needs supplemental therapy to be effective.

Endovascular treatment with stent deployment for ICA dissection with high-grade stenosis or occlusion may be most appropriate when anticoagulation fails to prevent a new ischemic event. In such cases, the MCA may be patent. However, to compare outcomes of patients with acute stroke consecutive to MCA occlusion due to ICA dissection treated either by stent-assisted endovascular thrombolysis/thrombectomy or by IV rtPA thrombolysis. Stent assisted endovascular thrombolysis/thrombectomy compared favorably with IV rtPA thrombolysis, underscoring the need for the instant device.

The main limitation of this procedure is the immediate need for an experienced endovascular therapist. The number of cases of MCA occlusion due to carotid artery dissection was quite small and represented <10% of patients admitted for carotid dissection. However, despite these promising preliminary results, potential drawbacks related to the procedure must be considered. Acute complications such as transient ischemic attack, ischemic stroke, femoral or carotid dissection, and death have been reported. Other potential hazards of endovascular treatment of carotid dissection could have been observed. On balance, the risk-benefit favors solutions like those disclosed herein.

Most patients with acute cerebrovascular syndrome with MCA occlusion consecutive to ICA dissection have poor outcomes when treated with conventional IV rtPA thrombolysis, whereas most patients treated with stent-assisted endovascular thrombolysis/thrombectomy show dramatic improvements. Further large randomized studies are required to confirm these data, which trends likewise are technical bases for the instant systems.

According to embodiments and as illustrated in FIG. 11, catheter-based revascularization system 1000 provides a platform for lysing emboli in occluded blood vessels. Accordingly, catheter-based revascularization system 1000 generally comprises control end 1002 and deployment end 1004. According to embodiments, control end 1002 is a portion of the device that allows a user, such as a surgeon, to control deployment of the device through the blood vessels of a patient. Included as part of control end 1002 is delivery handle 1006 and winged apparatus 1008, in some embodiments. Those skilled in the art readily understand module 1013 (see FIG. 12) is detachable.

According to some examples of the instant system during shipping of catheter-revascularization system 1000, shipping lock (not shown) is installed between delivery handle 1006 and winged apparatus 1008 to prevent deployment and premature extension of revascularization device 1024 (see FIG. 12) while not in use. Furthermore, by preventing delivery handle 1006 from being advanced towards winged apparatus 1008, coatings applied to revascularization device 1024 are stored in a configuration whereby they will not rub off or be otherwise damaged while catheter-based revascularization system 1000 is not in use.

According to embodiments, agent delivery device 1030 provides a conduit in fluid communication with the lumen of the catheter-based revascularization system 1000 enabling users of the system to deliver agents through catheter-revascularization system 1000 directly to the location of the embolus. The instant revascularization system delivery device may be made from materials known to artisans, including stainless steel hypotube, stainless steel coil, polymer jackets, and/or radiopaque jackets. In one embodiment, the revascularization systems comprise a plurality of apertures 1018 allowing infusable lytic agents to exit radially and distally into at least a subject embolus when transmitted through agent delivery device which is in fluid communication therewith. The revascularization systems according to several embodiments herein can comprise radiopacity for imaging purposes.

Accordingly, luer connector 1032 or a functional equivalent provides sterile access to the lumen of catheter-based revascularization system 1000 to effect delivery of a chosen agent. Artisans will understand that revascularization devices disclosed herein include embodiments made essentially of nitinol or spring tempered stainless steel. Revascularization devices likewise may be coated or covered with therapeutic substances in pharmacologically effective amounts or lubricious materials. According to embodiments, coatings include nimodipine, vasodialators, sirolamus, and paclitaxel. Additionally, at least heparin and other coating materials of pharmaceutical nature may be used.

Deployment end 1004 of catheter-based revascularization system 1000 comprises proximal segment 1010 and distal segment 1020. Proximal segment 1010, according to embodiments, houses distal segment 1020 and comprises outer catheter 1012 that is of a suitable length and diameter for deployment into the blood vessel of the neck, head, and cerebral vasculature. For example in some embodiments, proximal segment 1010 is from at least about 100 cm to approximately 115 cm long with an outer diameter of at least about 2.5 French to about 4 French.

Referring also to FIG. 12, distal segment 1020 comprises inner catheter 1022 and revascularization device 1024 (as shown here in one embodiment having uniform cells, variable cells likewise being within other embodiments), which is connected to inner catheter 1022. Inner catheter 1022, according to embodiments, is made from stainless steel coil, stainless steel wire, or ribbon or laser cut hypotube and is of a suitable length and diameter to move through outer catheter 1012 during deployment. For example, inner catheter 1022 extends from outer catheter 1012 38 cm, thereby giving it a total length of between at least about 143 and 175 cm (or between about 143 and 150 cm). The diameter of inner catheter 1022 according to the exemplary embodiment is 2.7 French, with an inner diameter of at least about 0.012 to 0.029 inches (or at least about 0.012 to 0.021 inches). The inner diameter of inner catheter 1022 may be any suitable diameter provided inner catheter 1022 maintains the strength and flexibility to both deploy and retract revascularization device 1024. In one embodiment, an inner catheter 1022' comprises a variable-pitch hypotube, as shown in FIGS. 13A-13D. In some embodiments, the hypotube has an outer diameter of 0.02", 0.022", or 0.016" and an inner diameter of 0.017" or 0.008". In some embodiments, the hypotube comprises a 25TW hypotube or a 31TW hypotube. In one embodiment, the inner catheter 1022' comprises a laser-cut, variable-pitch hypotube. Region L comprises a laser cut transition region of the variable-pitch hypotube. Regions P1, P2 and P3 comprise three regions of the variable-pitch hypotube having variable pitch. In one embodiment, the pitch decreases from region P1 to region P2 and from region P2 to region P3.

Referring to FIGS. 11 and 12, revascularization device 1024 is a self-expanding, reconstrictable retractable device tethered to inner catheter 1022. Revascularization device 1024 may be made from nitinol, spring tempered stainless steel, or equivalents as known and understood by artisans, according to embodiments. Revascularization device 1024, according to embodiments and depending on the particular problem being addressed, may be from at least about 3.5 mm to about 50 mm in its expanded state. In an expanded state, revascularization device 1024 is designed to expand in diameter to the luminal wall of blood vessel where it is deployed.

As known to artisans, revascularization device 1024 may be coated or covered with substances imparting lubricous characteristics or therapeutic substances, as desired. Naturally, the expandable mesh design of revascularization device 1024 must be a pattern whereby when revascularization device 1024 is retracted, it is able to fully retract into inner catheter 1022. The nature of the cell type likewise changes with respect to the embodiment used, and is often determined based upon nature of the clot.

In one embodiment, a revascularization device 1024' comprises a plurality of struts 1027 and a plurality of open cells 1029, as shown in FIGS. 14A-14C. In accordance with some embodiments, recapturability, flexibility and tracking are enabled by the struts of the revascularization device 1024', which permit flexion and extension to navigate through curved vessels. With reference to FIG. 4B, one or more markers can be pressed into pre-laser cut apertures 1026 designed to matingly embrace the same.

Catheter-revascularization system 1000 is deployed through a patient's blood vessels. Once the user of catheter-revascularization system 1000 determines that the embolus to be addressed is crossed, as known and understood well by artisans, revascularization device 1024 is deployed by first positioning outer catheter 1012 in a location immediately distal to the embolus.

Then, to revascularize/reperfuse the occluded blood vessel, distal catheter 1020 is deployed in a location whereby revascularization device 1024 expands at the location of the embolus, as illustrated by FIG. 12. The embolus is thereby compressed against the luminal wall of the blood vessel and blood flow is restored. Modular detachable segment 1013 is known also, and may be swapped out, as needed, if an Rx system is used.

As discussed above and claimed below, creating a channel for flow ideally includes making a vessel at least about halfway-patent, or 50% of diameter of a vessel being open. According to other embodiments, the channel created may be a cerebral equivalent of thrombolysis in myocardial infarction TIMI 1, TIMI 2, or TIMI 3.

Restoration of blood flow may act as a natural lytic agent and many emboli may begin to dissolve. Revascularization device 1024 is designed, according to embodiments, to radially filter larger pieces of the dissolving embolus and prevent them from traveling distal to the device and potentially causing occlusion in another location. Because the revascularization device provides continuous radial pressure at the location of the obstruction, as the embolus dissolves, the blood flow continues to increase.

After the embolus is lysed, revascularization device 1024 is sheathed into outer catheter 1012 and removed from the body. According to embodiments, larger pieces of the thrombus may be retracted with revascularization device 1024 after being captured in the radial filtering process. According to embodiments, revascularization device 1024 may be detachable whereby the revascularization device 1024 may detach from catheter-based revascularization system 1000 if it is determined that revascularization device 1024 should remain in the patient. As discussed above and illustrated in FIGS. 11 and 12, according to embodiments, catheter-based revascularization system 1000 reconstrainable attachment or attachment by tether may be optionally detachable. Revascularization device detachment methods comprise mechanical, electrical hydraulic, chemical, thermal, and those other uses known to artisans.

FIGS. 15A-15D illustrate an embodiment of a revascularization device 1500 configured for eccentric coupling to a pusher. The revascularization device 1500 can be tethered to a pusher (e.g., wire or tube) by a plurality of tether lines 1502 (also shown, for example, in FIGS. 12 and 12A). In some embodiments, the revascularization device 1500 is eccentrically coupled to the pusher (e.g., tethered off-center). In various embodiments, the revascularization device comprises an open proximal end and/or an open distal end and a generally cylindrical body (see, for example, FIGS. 12 and 12A and 14A-14C). FIGS. 16A-16F, 17A-17C, 18A-18D, 19A-19D, 20A-20C, 21A-21C, 22, 23, and 24A-24F illustrate various embodiments of revascularization devices. Other disclosure can be found in U.S. Provisional No. 60/980,736 and in U.S. application Ser. No. 12/123,390, which are expressly incorporated herein by reference.

As excerpted from U.S. Provisional No. 60/987,384, filed Nov. 12, 2007 and from U.S. application Ser. No. 12/123,390, filed May 19, 2008, which are incorporated herein by reference, FIGS. 25A, 25B, 26A, 26B, 27A, 27B, 28A, 28B, 29A, 29B, 30A-30E and 31A-31D illustrate various embodiments of rapid reperfusion devices. In one embodiment, a microcatheter having an active segment reperfuses occluded blood vessels above the junction of the subclavian artery and common carotid artery. The microcatheter is used to penetrate emboli. Once an embolus is penetrated, the active segment of the microcatheter is activated, causing it to expand radially and thereby open a channel for restored blood flow in the embolus. The blood's natural lytic action further degrades the embolus in some cases. Therapeutic agents may be administered through the microcatheter to aid in the reperfusion process. Active and passive perfusion are thus both enabled. In one embodiment, a device is disclosed comprising a distal segment having attached thereto a radially expandable active segment, a proximal segment comprising an active segment activator for radially expanding or retracting the active segment, an activation member connecting the active segment activator to the active segment. The distal segment is of a suitable diameter for use above the juncture of the subclavian artery and common carotid artery.

In one embodiment, a method is disclosed comprising providing a microcatheter having at least a distal segment, proximal segment, and active segment for use above the subclavian artery and common carotid artery, wherein the active segment is radially expandable.

In one embodiment, a catheter system for use above the juncture of the subclavian artery and common carotid artery is provided, although other uses are equally appropriate as determined by qualified medical personnel and may be introduced via a guidewire. The device operates as a standard microcatheter during introduction into a patient. The distal segment, which is remotely deployable, has attached to it an active segment that expands radially to reperfuse emboli. After reperfusion, the active segment is returned to its configuration prior to expansion and the entire microcatheter system is removed.

According to embodiments and as illustrated by an exemplary embodiment in FIG. 25A, there is shown microcatheter 1100. Microcatheter 1100 comprises proximal segment 1102 and distal segment 1104. Proximal segment 1102 remains outside of the patient and is used to insert and retract microcatheter 1100, as well as deploy active segment 1110 of distal segment 1104 during operation.

According to embodiments, catheter length and diameter are suitable for inserting into a human patient and capable of reaching a target embolus in the region above the subclavian and common carotid arteries. For example, according to embodiments, microcatheter 1100 is about 150 cm long; proximal segment 1102 is about 115 cm with an outer diameter of about 4 French and distal segment 1104 is about 35 cm with an outer diameter of about 2.7 French. In one embodiment, the microcatheter 1100 is 135 cm long, proximal segment 1102 is 90 cm long, and distal segment 1104 is 45 cm long. In one embodiment, the microcatheter 1100 has an inner diameter of 0.012". According to embodiments, a gradual decrease or stepwise in the outer diameter dimension as a function of the distal distance from proximal segment 1102, according to embodiments. For example, proximal segment 1102 is 4 French at the most proximal end and distal segment 1104 is 2.7 French at the most distal end. Disposed between is a segment having one or more intermediate outer diameters between 4 French and 2.7 French, such as 3.4 French and 3.0 French. The inner diameter of microcatheter 1100 is 0.012 to 0.021 inches, according to embodiments, which allows microcatheter to be inserted along a preinserted guidewire or used to infuse therapeutic agents. According to embodiments, the performance of microcatheter is comparable to standard microcatheters and is designed to track over a guidewire through the neurovasculature.

According to embodiments, microcatheter 1100 is designed to follow a path of least resistance through a thrombus. Guidewire inserted through a thrombus tends to follow the path of least resistance through the softest parts of each thrombus. When microcatheter 1100 is inserted, it likewise follows this path of least resistance. As blood flow is restored, the natural lytic action further helps to break up the thrombus.

According to embodiments, active segment 1110 comprises a radially expandable woven mesh or coil. The mesh may be made from materials well known and understood by artisans, including polymers, fluoropolymers, nitinol, stainless steel, vectran, or kevlar. Other biocompatible materials that may be woven or coiled are similarly contemplated. Active segment 1110 is, according to embodiments, 5 mm to 50 mm in length when expanded and is designed to substantially return to its preexpansion configuration for removal of microcatheter after reperfusion. In one embodiment, active segment 1110 is 15 mm long.

As indicated above, active segment 1110 comprises a mesh. The mesh comprises a plurality of individual units, having a uniform size or spacing geometry or a variable size or spacing geometry. According to embodiments where the size or spacing geometry is variable, smaller size or spacing geometry is used to provide a tight mesh for expanding a channel through the thrombus. Larger size or spacing geometry units allow from blood flow through active segment 1110. In one embodiment, active segment 1110 comprises a woven polymer mesh that is heparin coated. In one embodiment, active segment 1110 has a suitable porosity to permit blood flow when expanded. In one embodiment, releasing expansion of active segment 1110 will trap thrombus in the mesh.

According to embodiments, variable cell size or spacing geometry is accomplished with points where the braid crosses over fixed filaments (PICS). Thus, the cell size or spacing geometry varies by varying the density of the braid. Where high radial force is needed to open a channel in an embolus, for example, the filaments of the mesh are denser and therefore cross each other more often, yielding small cell size or spacing geometry that leads to the application of greater radial force when the mesh expands. Where perfusion is desired, the PICS are less dense and the resulting cell size or spacing geometry is increased. Additionally, drug delivery through microcatheter will be more effective in mesh configurations having a large size or spacing geometry.

Active segment 1110 may be coated or covered with substances, such as lubricious agents or pharmacologically active agents, according to embodiments. For example, active segment 1110 may be covered with heparin or other agents that are used in clot therapy, such as those that aid in dissolving clots or mitigating vasospasms.

According to similar embodiments, therapeutic agents are deployable through the lumen of microcatheter 1100, thereby allowing users of microcatheter 1100 to determine on a case-by-case basis whether to administer an agent. Accordingly, the braid/geometry of active segment 1110 is porous to allow the agent to pass from lumen of microcatheter 1100 into the blood vessel at the site of an embolus, for example.

Activation member 1120, according to embodiments, is a wire that connects proximal segment 1102 to distal segment 1104 and allows a user of microcatheter 1100 to deploy active segment 1110. Accordingly, activation member 1120 is made from stainless steel wire or braid, composites polymers and metal braids, ribbon or wire coils. According to embodiments, activation member 1120 comprises a hollow lumen that slidably moves over a guidewire to insert microcatheter 1100.

When active segment 1110 is expanded in a vessel, the radial expansion causes a channel to be formed in a thrombus for restored blood flow past the occlusion and thereby reperfuse the vessel. Activation of active segment 1110 is accomplished by mechanical methods, such as with activation member 1120 or by using liner of microcatheter 1110. Use of the liner is accomplished by leaving the liner unfused with active segment 1110.

For example, activation member 1120 fuses to the distalmost portion of activation segment 1110. According to embodiments, activation segment 1110 is heat set into a native confirmation in an expanded state. When activation member 1120 tensions active segment 1110, its confirmation changes from an expanded state into a deliverable state. Once delivered to the site of an embolus, activation member 1120 is adjusted to allow active segment 1110 to relax and thereby expand. According to similar embodiments, active segment 1110 is heat set into a native unexpanded confirmation. Activation member 1120 is used to tension active segment 1110 when delivered to the site of an embolus, thereby expanding it.

Other activation methods include electrical, chemical, and thermal activators, as is known and understood by artisans. Hydraulic activation may be accomplished with a balloon in the interior of the catheter that is filled with a fluid, thereby expanding the balloon, which expands active segment.

According to embodiments illustrated in FIG. 26A, microcatheter is inserted into a vessel having an occlusion.

As previously discussed, microcatheter is insertable along a guidewire through vessel lumen 1202, according to certain embodiments. Microcatheter 1100 penetrates embolus 1210 in vessel 1200. Active segment 1110 is positioned to coincide with the position of embolus 1210, according to techniques well known and understood by artisans. Thereafter, active segment 1110 is expanded, thereby opening a channel in thrombus 1210 and restoring blood flow, as illustrated in FIG. 26B.

Once activated, active segment 1110 allows blood to flow around microcatheter 1100 and active segment 1110 to create therapeutic benefits associated with reperfusion. For example and according to embodiments, the portions of distal segment 1104 immediately proximal and distal to active segment 1110 may have a diameter of 2.0 French to 3.0 French and have installed therein revascularization ports 1112, as shown in FIGS. 26A and 26B. Revascularization ports 1112 comprise openings in microcatheter 1100 that allow to blood flow through microcatheter 1100. Additionally, revascularization ports 1112 provide additional delivery points for therapeutic agents delivered through microcatheter 1100.

According to embodiments, a filter may be placed distal of active segment to prevent embolus pieces detached in the reperfusion process from escaping and causing distal occlusions. Accordingly, active segment is designed to capture pieces of embolus during the reperfusion processes. These pieces are captured within active segment 1110 when active segment 1110 is returned to its initial confirmation after expansion.

In some embodiments, active segment 1110 comprises an infusable microwire with an integrated filter as illustrated in FIG. 27A. In one embodiment, the infusable microwire has a diameter of 0.014". According to embodiments and as illustrated in FIG. 27B, active segment 1110 comprises an infusable coil. In one embodiment, the infusable coil has a diameter of 0.014". Accordingly, active segment 1110 comprises a large portion of distal segment 1104, wherein microcatheter 1100 itself coils when activated to create a channel through an embolus whereby blood flow is restored.

In some embodiments, the rapid reperfusion device comprises an infusable temporary stent as illustrated in FIG. 28A. According to embodiments illustrated by FIG. 28B, an infusable balloon is connected to microcatheter 1100 and comprises active segment 1110. Inflation of the infusable balloon opens a channel through the embolus and begins the lytic process.

FIGS. 29A-29D illustrate exemplary embodiments wherein active segment 1110 comprises different configurations designed to reperfuse an occluded blood vessel. According to embodiments illustrated in FIGS. 29A and 29B, active segment 1110 comprises an expandable coiled wire. The coiled wire may be made from stainless steel wire or braid, composite metal polymers, memory shape alloys such as nitinol, etc., wherein the coil is able to stably expand and return to its original state. As illustrated in FIG. 29A, the diameter of coil is substantially the same as that of microcatheter 1100 when in a nonexpanded state. However, when expanded (as illustrated in FIG. 29B) coil expands radially according to the reperfusion principles disclosed herein. According to embodiments, revascularization ports 1112 provide for increased blood flow through the lumen of microcatheter 1100. Activation of the coil may occur as previously disclosed, for example mechanically using activation member 1120, or by electrical or heat methods, as well known and understood by artisans.

FIGS. 30A-30D illustrate an embodiment of the present disclosure wherein active segment 1110 comprises a tethered mesh. According to this embodiment, active segment 1110 comprises mesh 1110A and tethers 1110B. Mesh is the same as previously described. According to embodiments, mesh comprises an open braid or a covered braid. The covering comprises, according to embodiments, a distal protection mechanism and may be a polymer, such as polyurethane, or other biocompatible cover materials such as ePTFE or related thin film. Tethers 1110B serve to provide structure for mesh 1110A, while providing large openings whereby blood may freely flow from the proximal to distal end of active segment 1110. Those skilled in the art will readily understand that materials for tethers and mesh may be the same, different, or interchangeable, as needed. FIG. 30E illustrates an embodiment of an active segment comprising an open braid or covered braid configured to be connected to the microcatheter via tethers or an open braid at both the proximal and distal end, thereby forming an open proximal end and an open distal end.

As shown in FIGS. 30A and 30B, microcatheter 1100 is inserted along guidewire 1300. In some embodiments, guidewire 1300 is compatible with 0.010" and 0.014". Active segment is initially in a non-expanded configuration. FIGS. 30C and 30D illustrate embodiments of active segment 1110 when extended. In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 CM.

According to embodiments illustrated in FIGS. 31A-31D, active segment 1110 comprises a wire mesh having variable spacing between the wires. FIGS. 31A and 31B illustrate active segment 1110 in a non-expanded configuration. FIGS. 31C and 31D illustrate active segment 1110 in an expanded position, as disclosed herein. In some embodiments, guidewire 1300 is compatible with 0.010" and 0.014". In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

As excerpted from U.S. Provisional Application Ser. No. 60/989,422, filed Nov. 20, 2007 and from U.S. application Ser. No. 12/123,390, filed May 19, 2008, which are incorporated herein by reference, FIGS. 32-36 illustrate embodiments of a temporary tethered stent mechanism and delivery system.

In some embodiments, the devices, methods and systems described herein facilitate and enable reconstruction of a vessel wall at the neck of an aneurysm.

According to embodiments, a tethered cage-like structure functions in conjunction with a coiling microcatheter system, among other things, by stabilizing vessel walls and providing tethered cage-like therapeutic support for treating aneurysms.

According to embodiments, methods and systems function with standard microcatheters to temporarily bridge aneurysmal necks.

According to embodiments, a cage-like structure is tethered to the end of a trackable delivery distal system. By bridging the neck of an aneurysm while permitting flow, coil embolization, for example, can be performed without risking vessel embolization. The tethered cage-like structure can then be proximally withdrawn.

According to embodiments illustrated in FIGS. 32-36, the system is optimized in a support role with other therapies.

Several methods of treating aneurysms have been attempted, with varying degrees of success. For example, open craniotomy is a procedure by which an aneurysm is located, and treated, extravascularly. This type of procedure has significant disadvantages. For example, the patient undergoing open craniotomy must undergo general anesthesia. Also, the patient undergoes a great deal of trauma in the area of the aneurysm by virtue of the fact that the surgeon must sever various tissues in order to reach the aneurysm. In treating cerebral aneurysms extravascularly, for instances, the surgeon must typically remove a portion of the patient's skull, and must also traumatize brain tissue in order to reach the aneurysm.

Other techniques used in treating aneurysms are performed endovascularly. Such techniques typically involve attempting to form a mass within the sac of the aneurysm. Typically, a microcatheter is used to access the aneurysm. The distal tip of the microcatheter is placed within the sac of the aneurysm, and the microcatheter is used to place embolic material into the sac of the aneurysm. The embolic material includes, for example, detachable coils or an embolic agent, such as a liquid polymer. The placement of these types of embolic materials suffer from disadvantages, most of which are associated with migration of the embolic material out of the aneurysm into the parent artery. This can cause permanent and irreversible occlusion of the parent artery.

For example, when detachable coils are used to occlude an aneurysm which does not have a well defined neck region, the detachable coils can migrate out of the sac of the aneurysm and into the parent artery. Further, it is, at times, difficult to gauge exactly how full the sac of the aneurysm is when detachable coils are being placed. Therefore, there is a risk of overfilling the aneurysm in which case the detachable coils also herniate or prolapse into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus the aneurysm can recanalize.

Embolic agent migration is also a problem. For instance, where a liquid polymer is placed into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Some such techniques, commonly referred to as flow arrest techniques, typically involve temporarily occluding the parent vessel proximal of the aneurysm, so that no blood flow occurs through the parent vessel, until a thrombotic mass has formed in the sac of the aneurysm which helps reduce the tendency of the embolic material to migrate out of the aneurysm sac. However, thrombotic mass can dissolve through normal lysis of blood. Also, in certain cases, it is highly undesirable to occlude the parent vessel even temporarily. Therefore, this technique is, at times, not available as a treatment option. In addition, even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

Cerebral aneurysms occur in approximately 2% of the population. Approximately 30,000 aneurysms are treated annually in the USA. Aneurysms grow from a weakness in a blood vessel. Origins of aneurysms are presently unknown but linked to hypertension and injury.

About 80% of aneurysms are less than 10 mm with the remainder growing to as large as 40 mm. Most large aneurysms have wide necks characterized with a neck greater than 4 mm or a dome to neck ratio less than 2:1.

In cases when aneurysms have a wide neck, either stent-assisted coiling in practice or balloon remodeling is performed to embolize the aneurysm. During stent-assisted coiling, a stent (for example, the Boston Scientific® brand of Neuroform™ system or the Johnson and Johnson Cordis® Enterprise™ brand of) structure is placed within the artery of the vessel with the aneurysm in an attempt to reconstruct the vessel wall at the neck of the aneurysm.

Patients are typically anti-coagulated and anti-aggregated with a combination of aspirin and Plavix® to mitigate the thrombo-embolic effects of a foreign body response. The patients will maintain the drug regimen long after the embolization procedure.

However, patients with sub-arachnoid hemorrhage (SAH) are not candidates for stents due the prophylactic drug regimen to mitigate the thrombo-embolic complications. A second approach is to perform balloon-remodeling. In this technique, a very soft, conformable balloon (the ev3 brand of Hyperform™ device) typically used for balloon-test-occlusion is placed in the artery at the neck to reconstruct the neck at the aneurysm origin. However, during this technique, flow arrest is performed while the balloon is inflated.

There is a risk of initiating an ischemic event during balloon remodeling and/or a thrombo-embolic event during flow arrest. This technique can be used during SAH because no additional prophylactic drug regimen is required. Once both these techniques are performed, coil embolization of the aneurysm can be performed. During the stenting procedure, the stent is permanently implanted. During balloon remodeling, the balloon is removed once embolization is completed.

A device that can reconstruct the vessel wall at the aneurysm neck origin has been created by tethering a cage-like structure to the distal end of a trackable delivery system. For example, the MindFrame® brand of cage-like structure tethered stent can be placed across the neck of aneurysm without prophylactically administered aspirin and Plavix® as well as not obstructing flow. The tethered stent allows perfusion through the body of the structure and provides support to the neck of the aneurysm allowing coil embolization procedure the tethered stent can be withdrawn proximally into the standard delivery microcatheter.

The device is delivered through standard microcatheters currently available to the interventionalist. An embolization microcatheter can either be placed into the aneurysm prior to placement of the tethered stent or after placement of the tethered stent. If the latter is preferred then the coil embolization microcatheter must be placed through the struts of the tethered stents to access the body of the aneurysm to commence coiling. Both techniques are performed during standard stenting procedures.

Figure 32:
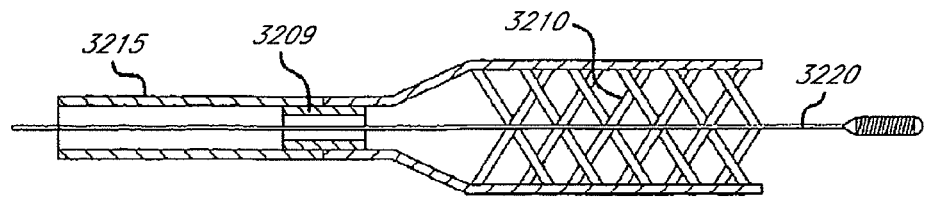

Referring to FIG. 32, delivery tube 3215 deploys tethered cage-like device/temporary stent 3210 prior to embolization, using a standard over-the-wire (OTW) system. The instant system is able to be deployed prior to embolization, used to reconstruct the arterial wall at the aneurysm neck, hold in place emboli material and then be able to be removed after embolization or the aneurysm sac is complete.

The system provides a method to assist in aneurysm embolization that does not restrict blood flow and can be used without placing patients on ASA/Plavix® during embolization. During balloon remodeling, flow arrest is performed. During stenting, patients need ASA/Plavix®.

According to the disclosure, a temporary tethered cage-like structure/tethered stent 3210 is non-detachable in some embodiments but attached either to a hypotube or guide wire 3220 allowing it to be navigated into tortuous vasculature in the brain. The device and system are deployed prior to embolization, as discussed above and claimed below. Device 3210 may be attached to guide-wire 3299 or tube 3215.

Figure 33:
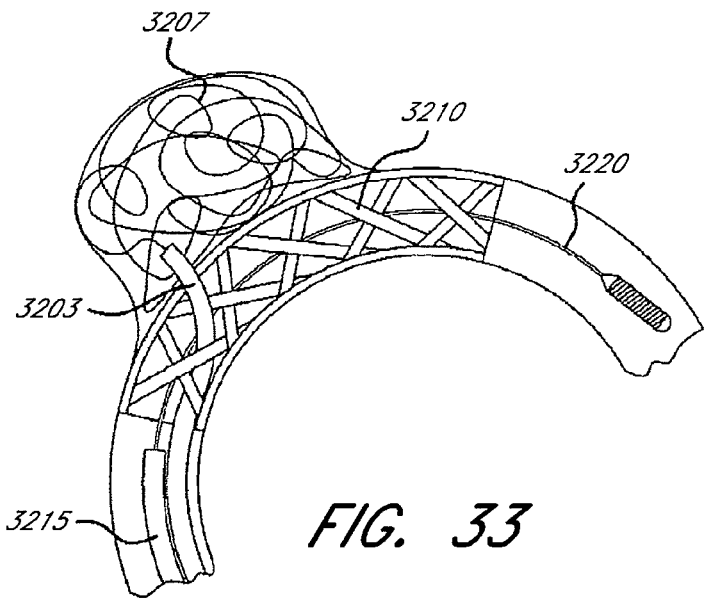
Figure 34:
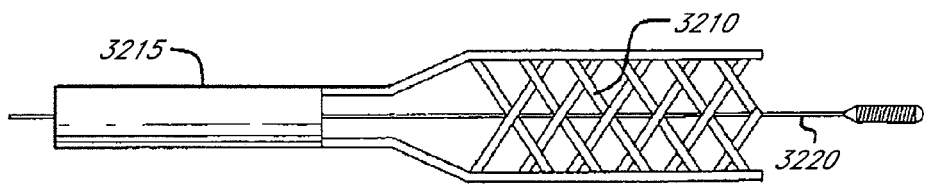
Figure 35:
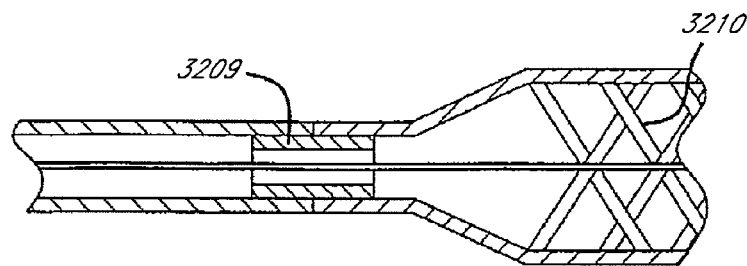

Referring also to FIG. 33 through FIG. 35, microcatheter/delivery tube 3215 emplaces cage-like temporary stent 3210 at aneurysm neck, while a coiling microcatheter 3203 accesses an aneurysm, and allows coil 3207 to be placed therein. Delivery tube 3215 and cage-like temporary stent 3210 are known in the art and may include Nitinol® or the like "super-elastic" materials.

FIG. 34 likewise provides further details of the instant system, with tethered cage-like structure/temporary stent 3210 being released from delivery tube 3215 using known OTW techniques.

Figure 36:
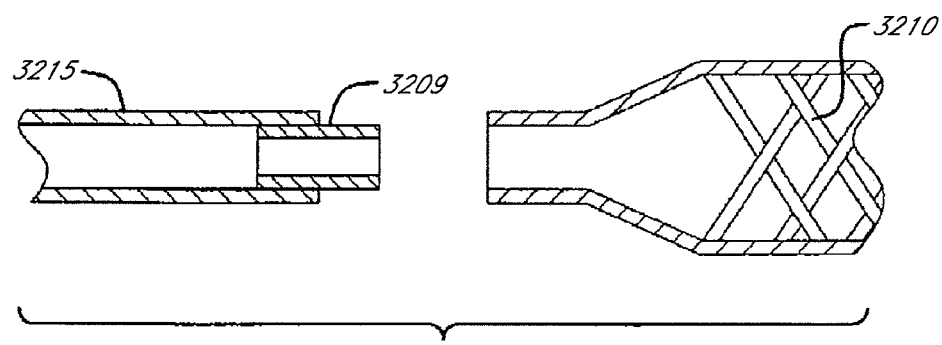

FIGS. 35 and 36 likewise show intermediate steps, whereby placement of the system allows an aneurysm to be isolated, at the neck, whereby coils 3207 may be used. According to embodiments illustrated by FIG. 36 if coil 3207 somehow gets caught in stent 3210, it may be impossible to remove the device without causing damage to or rupturing the vessels. Therefore, according to embodiments, stent 3210 may be detachable (e.g., via attachment mechanism 3209), enabling it to be left in the vessel in the event a complication where it cannot be safely removed.

The delivery tube 3215 is a variable stiffness tube that is able to track to and through the tortuous anatomy or the cerebral vasculature (i.e., internal carotid artery, MCA, ACA, vertebral and basilar).

The delivery tube 3215 can be one or two pieces but must have greater proximal pushability (stiffness) & greater distal flexibility (softness) to allow tracking to distal cerebral arteries.

The delivery tube 3215 should also have a lumen that enables tracking over a guide-wire. This feature provides a few benefits: ability to track and be delivered; ability to maintain access in the event different size devices need to be exchanged; and ability to provide support to arterial tree during device deployment and recovery. A flexible device may tend to herniate or prolapse into openings. The guide-wire provides a pathway (concentric) to the artery and supports the device preventing such technical complications.

The delivery tube 3215 can be mechanically attached to the tethered stent by soldering, welding or press fitting. Likewise, those skilled in the art readily understand their attachment mechanisms.

The cage-like structure/stent is made of Nitinol to allow it to be compressed and loaded into an introducer for packaging. Similarly memory-based materials likewise function, in accordance with the instant systems.

The introducer enables the device to be transferred into a microcatheter and deploy to a trusted location such as an aneurysm neck.

The cage-like structure/stent is attached to the delivery wire described previously.

By attaching it to a delivery wire, the cage-like structure/stent can be placed, retracted, repositioned and recaptured into a microcatheter.

This is an important feature. The device, being temporary, allows for the following: 1) perfusion of blood through artery during coiling; 2) perfusion from coiling herniation or prolapse; and 3) removal of the device, mitigating the use of Aspirin and Plavix.

A technical basis for the term "super-elastic" found in the class of nickel-titanium alloys known as "nitinol" alloys discovered by the United States Navy Ordinance Laboratory. These materials are discussed in length in U.S. Pat. No. 3,174,851 to Beuhler, et al; U.S. Pat. No. 3,351,463 to Rozner, et al; and U.S. Pat. No. 3,753,700 to Harrison, et al. Alloys known to be suitable are those containing at least 1.5% (wt) and up to about 85% (wt) or more, of one or more alloying members selected from the group consisting of vanadium, chromium, manganese, iron, and cobalt. By the term "stent" or "ribbon", we intend to include elongated shapes, the cross section of which are not square or round and may typically be rectangular, oval, or semi-oval. They should have an aspect ratio of 0.05 (thickness/width) or less, depending on application at issue. Other disclosure can be found in U.S. Provisional No. 60/989,422, which is expressly incorporated herein by reference.

As excerpted from U.S. Provisional Application Ser. No. 61/015,154, filed Dec. 19, 2007 and from U.S. Utility Application Ser. No. 12/182,370, filed on Jul. 30, 2008 and U.S. Utility Application Ser. No. 12/123,390, filed on May 19, 2008, which are incorporated herein by reference, FIGS. 37A, 37B, and 38-40 illustrate embodiments of a device and method for capturing emboli and FIGS. 41 and 42 illustrate delivery device assemblies.

In some embodiments, the devices, methods, and systems described herein facilitate and enable treatment of ischemic or hemorrhagic stroke. More specifically, a tethered basket-like system operates in conjunction with a microcatheter system, to provide arterial support and capture emboli.

In one embodiment, a device for the removal of emboli is disclosed comprising a mesh capturer having at least an undeployed state and a deployed state, the mesh capturer being inserted into the neurovasculature in an undeployed state and removed from the microvasculature in its deployed or retracted state. wherein the mesh capturer is deployed into its deployed state distal to an embolus and advanced proximally until the embolus is substantially contained within the mesh capturer; and wherein the basket is deployed above the subclavian artery and common carotid artery. In some embodiments, the device is inserted into the vasculature over a guidewire. In some embodiments, the device is inserted into the vasculature as a component of a rapid exchange system.

In one embodiment, a method for removing an embolus is disclosed comprising inserting a microcatheter and guidewire distal to an embolus; inserting a embolus capture device over the wire through the microcatheter distal to the embolus; deploying the embolus capture device; retracting the deployed embolus capture device until the embolus is substantially contained within the embolus capture device; and removing the embolus capture device.

The ideal stent for intracranial use would be flexible, precisely delivered, retrievable, able to be repositioned, atraumatic, available in various lengths and diameters, thin-walled and radiopaque. It should provide sufficient coverage to restrain coils, while having wide enough fenestrations to permit catheterisation with coil or other embolic agent delivery catheters. The currently available over-the-wire stents are not ideal. The balloon-expandable stents of sufficient length are too stiff to be reliably and safely deployed. While existing self-expanding stents offer some improvement in this respect there are still serious difficulties in deploying them in distal locations and the currently available or planned stents for intracranial use are not available in the small diameters necessary for distal intracranial use.

The stent is delivered through a micro-catheter, allowing standard microcatheter/wire techniques to reach locations inaccessible to over-the-wire stents. A particularly appealing characteristic is its ability to be retrieved and repositioned after complete delivery, if its position is felt to be suboptimal or if the stent proves not to be necessary. The stent conforms completely to the normal vessel geometry and is not prone to strut opening on convexities. It is compatible with all currently used embolic agents for aneurysm occlusion and is MR compatible.

Stents have been used widely in occlusive lesions in the peripheral, renal, and coronary arteries to treat stenosis of vessels narrowed by a variety of pathologic conditions. Initially used mainly in extracranial cerebral vessels for carotid artery stenosis or the treatment of pseudoaneurysms of the extracranial carotid artery, small stents are now increasingly used for intracranial vessel disease such as the treatment of wide-necked aneurysms not amenable to conventional endovascular techniques.

Major limitations of the currently available stents, usually cardiac stents, however, are their relative stiffness, rendering them not flexible enough to pass the C1/C2 vertebral artery or carotid siphon tortuosities.

The design constraints for the device used in this study were to develop an endovascular stent that is flexible enough to be delivered via a microcatheter and to be placed in small vessels but with sufficient radial forces to conform to the vessel wall when deployed.

According to embodiments of the system illustrated in FIGS. 37A, 37B, and 38-40, by leveraging a conventional self-expanding reperfusion device delivery platform, a polymodic system can be iterated which crosses an embolus, filters, and either removes the offending embolus or is optionally emplaced to address the same. A paucity of extant systems effective for such combination therapies is noted among the art.

According to embodiments of the system illustrated in FIGS. 37A, 37B and 38-40, the system allows for natural lysis, perfusion of the challenged vessels, and importantly filters any particulates generated, to obviate the need to be concerned with distal migration of the particulates generated. In some embodiments, the emboli removal devices are used to treat, among other things, ischemic stroke. Naturally, therefore, the emboli removal devices of the present disclosure are designed to be used in neuro-type applications, wherein the specifications of the present catheters and emboli removal devices may be deployed in the blood vessels of the cerebral vascular system. Similarly contemplated for the emboli removal systems and catheters of the present disclosure is deployment in other parts of the body wherein the specifications of the present disclosure may be used in other vessels of the body in a non-invasive manner.

According to embodiments illustrated in FIGS. 37A, 37B, and 38-40, disclosed herein are devices and methods of the removal of neurocranial emboli without causing distal complication arising from the passing of larger pieces of a recovered embolus distal to the location of the original embolus.

According to embodiments illustrated in FIGS. 37A, 37B, and 38-40, disclosed herein is a catheter-emboli removal system. The emboli removal devices of the present disclosure are for reperfusion of blood vessels. When the catheter-emboli removal system illustrated in FIGS. 37A, 37B, and 38-40 is deployed into a blood vessel having an embolus, the emboli removal device is expanded and moved proximally along the vessel so that the embolus is substantially contained with the mesh basket of the emboli removal device.

In one embodiment, deployment of the system illustrated in FIGS. 37A, 37B, and 38-40 establishes immediate 50% of the diameter of the lumen patency of the vessel being addressed by removing the embolus occluding the vessel. Among the prior art, no system having adequately small profile with flexibility to promote improved access for in-site treatment is known which may be used as a temporary (not implanted) solution and removed without substantial damage to the vasculature.

Additionally, in reperfusion applications the emboli removal device may be deployed as a safety device. As the embolus lyses, the deployed emboli removal device filters larger embolus particles from migrating distally, thereby reducing the chances of further complications. If reperfusion is unsuccessful, then the emboli removal device is retracted proximally, thereby substantially capturing the embolus. Then the entire device is removed together with the microcatheter.

According to embodiments and as illustrated in FIG. 37A, a cross sectional view of an artery 2110 having embolus 2120 in artery lumen 2112 is shown. Guidewire 2130 inserted through a thrombus tends to follow the path of least resistance through the softest parts of embolus 2120. When a microcatheter is inserted along guidewire 2130, it likewise follows this path of least resistance. Accordingly, when a stent or embolus capture device is inserted via guidewire 2130, it is deployed offset because guidewire 2130 is not centered in the vessel in many cases, as illustrated in FIG. 37B.

To address the problem of the guidewire offset, the inventors devised an embolus capture device 2200 that is adept at capturing embolus 2120 even when deployed in an offset way. As part of the embolus capture device 2200 design, pieces of embolus 2120 that break away from embolus 2120 are recaptured to prevent potential migration more distal in the vasculature which may potentially cause other emboli, too remote to safely address.

As illustrated in FIG. 38, blood vessel 2110 is shown having vessel lumen 2112 and embolus 2120. As illustrated, embolus capture device 2200 is deployed for capture of embolus 2120. As illustrated, embolus capture device 2200 is deployed along an offset guidewire. However, embolus capture device 2200 is designed for offset deployment to deploy such that it occupies about the center of vessel 2110, which ensure maximum efficiency in the capture of embolus 2120. It will be readily recognized that the devices of the present disclosure need not be deployed offset.

Embolus capture device 2200 comprises mesh basket 2210 and tethers 2220 which are deployed from microcatheter 2230. Mesh basket 2210 comprises a radially expandable woven mesh or coil basket open on the proximal end and closed at the distal end. The mesh may be made from materials well known and understood by artisans, including polymers, fluoropolymers, nitinol, stainless steel, vectran, or kevlar. Other biocompatible materials that may be woven or coiled are similarly contemplated. Mesh basket 2210 connects to microcatheter 2230 via tethers 2220 and is designed to be compatible such that it is removable in its deployed state without causing dissection or other damage to the vasculature.

Mesh basket 2210 comprises a plurality of individual units, having a uniform size or spacing geometry or a variable size or spacing geometry. According to embodiments where the size or spacing geometry is variable, smaller size or spacing geometry is used to provide a tight mesh for preventing the passage of small pieces of embolus 2120 that break away. In all cases, size or spacing geometry will not allow pieces of embolus 2120 that may cause potential complications. In some embodiments, the mesh basket 2210 comprises struts having increased thickness adjacent to the proximal end 2211 of the mesh basket 2210 to provide tensile strength for opening the mesh basket 2210, such as described in U.S. Provisional No. 61/015,154, which is incorporated by reference herein.

Tethers 2220 serve to provide structure for mesh basket 2110, while providing large openings whereby blood may freely flow from the proximal to distal end of embolus removal device 2200. According to embodiments, tethers 2220 are made from the same material as mesh basket 2210. Those skilled in the art will readily understand that materials for tethers and mesh may be the same, different, or interchangeable, as needed.

During deployment of embolus capture device 2200, mesh basket is stored in microcatheter 2230 in an undeployed state. In the undeployed state, microcatheter 2230 is advanced distal to embolus 2120 and mesh basket 2210 is deployed. According to embodiments, both mesh basket 2210 and tethers 2220 are deployed distal to embolus 2120 to prevent tethers 2220 from dislodging pieces of embolus 2120 prior to full expansion of mesh basket 2210, thereby preventing the pieces from advancing distal to the embolus 2120 before mesh basket 2210 is in place to filter them.

After deployment, according to embodiments, embolus removal system 2200 is retracted proximally until embolus is substantially contained within mesh basket 2210. Thereafter, mesh basket 2210 and microcatheter 2230 are removed from the vasculature of the patient. During removal of mesh basket 2210 and microcatheter 2230, embolus 2120 is trapped within mesh basket 2210 and withdrawn from vessel 2110. In some embodiments, a foreign body is the target of removal. The foreign body can comprise, for example, a microcoil, a medical device, a kidney stone, and/or a gallstone.

According to embodiments, microcatheter 2230 length and diameter are suitable for inserting into a human patient and capable of reaching a target embolus in the region above the subclavian and common carotid arteries. For example, according to embodiments, microcatheter 2230 is about 150 cm long; microcatheter has a proximal segment (at a control end of microcatheter 2230) that is about 115 cm long with an outer diameter of about 3.5 French and a distal segment (at a deployment end of microcatheter 2230) is about 35 cm with an outer diameter of about 2.7 French. The inventors contemplate, according to embodiments a gradual decrease or stepwise in the outer diameter dimension as a function of the distal distance from proximal segment, according to embodiments. For example, proximal segment is 3.5 French at the most proximal end and distal segment is 2.7 French at the most distal end. Disposed between is a segment having one or more intermediate outer diameters between 3.5

French and 2.7 French, such as 3.2 French and 3.0 French. The inner diameter of microcatheter 2230 is 0.012 to 0.029 inches, according to embodiments, which allows microcatheter to be inserted along a preinserted guidewire or used to infuse therapeutic agents. According to embodiments, the performance of microcatheter 2230 is comparable to standard microcatheters 2230 and is designed to track over a guidewire through the neurovasculature.

As illustrated by embodiments in FIG. 39, embolus capture device 2200 may be deployed concurrently with a reperfusion device 2211. As embolus 2120 is reperfused with reperfusion device 2211, embolus capture device 2200 provides a safety feature whereby pieces of embolus 2120 that break away are captured in mesh basket 2210 and removed with the reperfusion device generally. Additionally, as vessel 2110 reperfuses due to natural lytic action, mesh basket 2210 provides a minimum particle size permitted to pass distal to embolus capture device 2200. Consequently, embolus capture device 2200 prevents further complications distal to the original site of the occlusion by preventing larger embolus 2120 pieces or particles from passing deeper into the neurovasculature and occluding it in more distal locations.

Alternately and as illustrated according to embodiments in FIG. 40, embolus capture device 2200 is used after reperfusion is unsuccessfully attempted or not successful to the desired level. Accordingly, microcatheter 2230 is inserted into the neurovasculature in operation 2502 as well known and understood by artisans. Reperfusion is attempted, for example with the reperfusion device 2211 of FIG. 39 in operation 2504 of FIG. 40. In some embodiments, a catheter-revascularization system is deployed through a patient's blood vessels. Once the user of catheter-revascularization system determines that the embolus to be addressed is crossed, a revascularization device (e.g., reperfusion device 2211) is deployed by first positioning an outer catheter (e.g., microcatheter 2230) in a location immediately distal to the embolus. Then, to revascularize, or reperfuse, the occluded blood vessel, the reperfusion device is deployed in a location whereby the reperfusion device expands at the location of the embolus. The embolus is thereby compressed against the luminal wall of the blood vessel and blood flow is restored. After reperfusion is attempted, the success is determined in operation 2506. For example, a contrast dye is used to determine the level to which the occluded vessel is reperfused, as is well known to artisans.

If reperfusion is not successful to a desired degree, then embolus capture device 2200 is inserted through the microcatheter 2230 as described herein and deployed distal to the embolus 2120. For example, creating a channel for flow ideally includes making a vessel at least about halfway-patent, or 50% of diameter of a vessel being open. According to embodiments, the channel created may be a cerebral equivalent of thrombolysis in myocardial infarction (TIMI) 0, TIMI 1, or TIMI 2, TIMI 3, and thrombolysis in cerebral infarction (TICI) and TICI 3. In these cases, blood flow is not accomplished to a desired degree. It is therefore desirable to remove the entire embolus. Thus, after embolus capture device 2200 is deployed distal to the embolus, it is retreated proximal until embolus 2120 is substantially inside of mesh basket 2210 in operation 2512. Thereafter, mesh basket 2210, embolus 2120, and microcatheter 2230 are removed.

The embolus capture devices of the present disclosure may be designed for over the wire deployment or rapid exchange deployment, according to embodiments.

In one embodiment, ischemic stroke reperfusion or clot capture is performed by a reperfusion device or embolus capture device comprising a NiTi cut tube.

One embodiment for ischemic stroke clot retrieval includes an eccentric design. This embodiment addresses the problem during clot removal of the thrombectomy device being forced off-center because of microcatheter positioning after the microcatheter/guidewire passes the embolus. This "off-centering" causes the device to miss the embolus when pulled proximal to attempt to capture it or fragmenting will occur because the device will shave the embolus. In some embodiments, an off center delivery system is used to capture the embolus. In some embodiments, the struts are designed or favored to the periphery of the artery as opposed to the center of the artery. In some embodiments, the struts are designed to accumulate in 270 degrees of the thrombectomy device allowing open space for the embolus to fall into. By making the attachment point off-center, the open area is increased. By making the device off-center from the point of attachment to the delivery system, the device must increase the chance of capturing the embolus, which is also off-center from the microcatheter.

The chart below illustrates several ischemic stroke delivery system assembly embodiment options:

| 1st Option | | 2nd Option | |
|---|---|---|---|
| Hypo: (24 TW) | .022" × .014" | Hypo: | .0215" × .0155" |
| Ribbon Coil: | .003" × .005" × .015" | Ribbon Coil: | .003" × .005" × .015" |
| PET Heat Shrink: | .027" × .00025" Wall | PET Heat Shrink: | .027" × .00025" Wall |
| or | .028" × .0004" Wall | | |
| 3rd Option | | 4th Option | |
| Hypo: | .022" × .014" | Hypo: | .0215" × .0155" |
| Ribbon Coil: | .003" × .010" × .015" | Ribbon Coil: | .003" × .010" × .015" |
| PET Heat Shrink: | .027" × .00025" Wall | PET Heat Shrink: | .027" × .0025" Wall |
| or | .028" × .0004" Wall | | |

In some embodiments, the delivery systems maintain an outer diameter at the solder joint of 0.024" max. In some embodiments, the PET heat shrink is installed over the distal 45 cm of the delivery device. In some embodiments, the distal tip of the delivery system is trimmed after installation of the PET heat shrink. In some embodiments, the distal and_proximal ends of the delivery system are deburred. In some embodiments, the delivery systems must accept a 0.010" guidewire.

FIG. 41 illustrates embodiments of a distal end of a hypotube assembly 4100 that includes a solder joint 4111 between a hypotube 4112 and a ribbon coil 4113 and a PET heat shrink 4114. FIG. 41 illustrates example outer diameter and length dimensions of the delivery system assembly.

The chart below illustrates dimensions for embodiments of the hypotube assembly, or delivery system.

| Design | Hypotube OD | Ribbon Coil | PET | PET Prox | PET @ Joint | PET Distal |
|---|---|---|---|---|---|---|
| 1 | .022" × .014" 24 TW | .003" × .005" × .015" | 0.027" × .00025" × 45 cm | .023" | .024" | .023" |
| 2 | .022" × .014" 24 TW | .003" × .010" × .015" | 0.027" × .0025" × 45 cm | .023" | .024" | .023" |
| 3 | .0215" × .0155" | .003" × .005" × .015" | 0.027" × .0004" × 45 cm | .022" | .025" | .0225"/.023" |
| 4 | .0215" × .0155" | .003" × .010" × .015" | 0.027" × .0004" × 45 cm | .022" | .025" | .0225"/.023" |
| 5 | .022" × .014" | .002" × .010" × .017" | 0.028" × .0004" × 45 cm | .022" | .0245" | .023"/.025" |

The embodiments disclosed in the tables above accept a 0.010 G.W. (guidewire) straight. In some embodiments, the distal tip of the hypotube 4112 is ground (e.g., to 0.017") to accept the inner diameter (e.g., 0.01") of the ribbon coil 4113. The distal tip of the hypotube 4112 is soldered to the proximate tip of the ribbon coil 4113. The PET 4114 is cut to 45 cm, the heat shrink is heated to 400 degrees Fahrenheit, and restrained while heated.

EXAMPLE 2

In Vitro Tracking Evaluation Test

A study was performed to evaluate in-vitro tracking of embodiments of delivery system. The testing equipment included: a FlowTek A201 with stroke model, a 5F CORDIS® ENVOY™ MPD guide catheter, a 135 cm×0.027" inner diameter CORDIS® MASS TRANSIT™ microcatheter, and a 0.010 diameter×200 cm length TRANSEND® guidewire. The study used the following numbered scoring system: (1) pass with no friction at all; (2) pass with acceptable friction; (3) pass with some friction; (4) pass with difficulty; (5) can't pass.

| Design # | Curve 1 | Curve 2 | Curve 3 | Curve 4 | PCOM | A1/M1 | M2/M3 |
|---|---|---|---|---|---|---|---|
| 1 | 2/3 | 2/3 | 2/3 | 2/3 | 2/3 | 2/3 | 2 |
| 2 | 3 | 3 | 3 | 3 | 3 | 3 | 2 |
| 3 | N/A | N/A | N/A | N/A | N/A | N/A | N/A |
| 4 | 2 | 2 | 2 | 2 | 2 | 2 | 2 |
| 5 | 1 | 1/2 | 1/2 | 1/2 | 1/2 | 1/2 | 1/2 |

The following notes were taken from the study regarding guidewire tracking. Design 1 passed fine until the PCOM segment with a score of 4. Design 2 experienced some friction requiring 300 cm of exchange wire with a score of 3/4. Design 4 scored a 5 at curve 4. Design 5 scored a 4 generally. Designs 3 and 4 had a 0.015" inner diameter and designs 1 and 2 had a 0.014" inner diameter. Design 5 had a 0.002"×0.010"×0.018" hypotube ribbon coil.

FIG. 42 illustrates an embodiment of a distal end of a delivery system assembly 4200. In one embodiment, the delivery system assembly 4200 includes a proximal hypotube 4212, a distal braid 4213 and a polyimide liner 4215. In one embodiment, the polyimide liner 4215 may be a braid. In one embodiment, the braid needs 0.0006" wire.

Strut thicknesses for the recanalization or reperfusion devices described herein can include 0.0040", 0.002", 0.0020", and 0.0009". The strut thicknesses may vary. The devices may be used for reperfusion and may be tethered. The devices may or may not be recapturable and may or may not include markers.

In some embodiments, the devices described herein are to be used for clot removal and comprise a clot basket or spiral basket. In one embodiment, the clot removal device comprises a woven retrieval basket. The woven retrieval basket may include features such as an over the wire design, low porosity fine wires in the basket area to support a clot (wire dia: 0.035 mm and 56-97 pics/cm), or thicker wires that open the basket and give it tensile strength (wire dia: 0.076 mm). The woven retrieval basket may also be fully automatable.

In another embodiment, a reperfusion catheter device includes a nitinol braid. In one embodiment, the braid includes 24 strands with a wire size of 0.076 mm, a braid angle of 42 degrees, an expanded diameter of 3.5 mm, and a collapsed diameter of approximately 0.030". Other disclosure can be found in U.S. Provisional No. 61/015,154, which is expressly incorporated herein by reference.

As excerpted from U.S. Provisional Application Ser. No. 61/044,392, filed Apr. 11, 2008 and from U.S. Utility application Ser. No. 12/422,105, filed Apr. 10, 2009, which are incorporated herein by reference, FIGS. 43A-43C illustrate embodiments of rapid exchange neuro-microcatheter delivery systems.

In some embodiments, microcatheter devices and therapy schemes are provided whereby access is maintained during capture of emboli/thrombi/clot material without compromise to reperfusion of blood flow. The instant disclosures include microcatheters having at least second lumens for vessel stability during removal of emboli and/or in adjunct therapy modes, these devices are referred to as "Rapid Exchange" or RX systems.

Devices, processes and systems facilitate and enable treatment of acute stroke conditions, providing reperfusion while therapy is made available by preserving structure in the arterial tree. Using a Rapid Exchange approach with at least dual lumens in a microcatheter facilitates embolus/clot removal without damaging sensitive vasculature.

The rapid exchange system described with reference to FIGS. 43A-43C allows and maintains arterial access to treatment sites, and provides enhanced support to the arterial tree, while working as a rapid exchange system. This enables secure capture of emboli/thrombi/clot material by providing support within the vessel. The RX support provided prevents the proximal vessel from buckling or kinking during tensioning upon embolus removal. This is a key feature, in that the literature is demonstrative of ovalizing, whereby stripping of the embolus from capture devices happens when buckling or kinking happens.

Several methods of treating stroke have been attempted, with varying degrees of success. However, according to the instant teachings, blood can be reperfused or emboli/thrombi/clot material can be removed from the neurovasculature consistently and safely with arterial support and access maintained during the procedure.

Other techniques used in addressing this issue comprise coextruded microcatheters having multi-lumen structures, as would be known to Artisans based on this disclosure.

According to the disclosure, an OTW system, using a guidewire (sizing ranges from 14 to 18, such as the TRANSEND® or SYNCRO® brands) and a microcatheter (0.010 to at least about 0.28 maximum) having a delivery system tube (such as the MASS TRANSIT® or RENEGADE® brands) approximately sized is combined with a rapid exchange system as discussed above. The OTW system may be configured to fit within a lumen of the RX system. A microcatheter may be configured to fit within another lumen of the RX system.

The rapid exchange delivery catheter functions with, for example CORDIS® brands of microcatheters available from them, and is assembled as detailed below in the claims, or as known to those skilled in the art.

Referring now to FIG. 43A, according to embodiments of the present disclosure, guidewire 4399 accesses and crosses a target lesion, providing a pathway for RX microcatheter 4301 having at least two lumens. Stroke device 4303 is shown in a state of transition from a first (collapsed) position to a second (expanded) position emerging from a lumen of RX microcatheter 4301. According to embodiments, guidewire 4399 may be at least partially disposed within one of the two lumens of RX microcatheter 4301.

Referring now to FIG. 43B, according to embodiments of the present disclosure, stroke device 4303 includes radiographic marking elements 4305 for visualization during placement. Referring now also to FIG. 43C, stroke device 4303 is shown in a fully expanded position, whereby it functions consistently and safely such that arterial support is maintained in virtue of guidewire 4399 keeping the arterial tree from mechanical stress, while embolus removal, clot capture and other procedures are done. Thus, reperfusion is established and therapy administered without risks to patients present with other devices. According to embodiments, as shown in FIG. 43C, stroke device 4303 may be tethered such that, while emplaced at a treatment site within a blood vessel, it remains accessible via a microcatheter and readily retrievable therein while maintaining reperfusion of the blood vessel. According to embodiments, stroke device 4303 may be emplaced on a long-term of permanent basis, or as needed based on the amount and type of recanalization prescribed. According to embodiments, stroke device 4303 is self-expandable, such that is may expand substantially radially when removed from within the catheter. According to embodiments, additional therapies may be provided while stroke device 4303 is fully expanded, for example, through another lumen of RX microcatheter 4301.

According to embodiments of the present disclosure, a process for making a neuro-monorail microcatheter is disclosed. The process may include cutting a first microcatheter at a distal end. A segment may be cut at about 5 cm to 50 cm from a distal end of the microcatheter. The segment of the first catheter may be aligned adjacent to a distal section of a second microcatheter. Guidewires may be placed in each of first and second microcatheters to maintain their respective alignments and keep their lumens open. A resin, such as Polyethylene terephthalate (PET), may be applied in short segments along the lengths of the first and second microcatheters to secure and maintain alignment and adjacent status of the finished device.

According to embodiments of the present disclosure, a first and second catheter, as described above, may be coextruded and skived, in lieu of the cutting discussed above, and joined as discussed above. Other disclosure can be found in U.S. Provisional No. 61/044,392, which is expressly incorporated herein by reference.

As excerpted from U.S. Provisional Application Ser. No. 61/166,725, filed Apr. 4, 2009, which is incorporated herein by reference, FIGS. 44-54 illustrate embodiments of balloon catheter and delivery systems, and methods of use thereof.

According to embodiments of the present disclosure, a device and method are disclosed for treating occlusions of blood vessels, veins, and arteries, including neurovasculature, such as above the carotid artery. Occlusions may be partial or complete, and may be attributable to one or more of emboli, thrombi, calcified lesions, atheroma, macrophages, lipoproteins, any other accumulated vascular materials, or stenosis. According to embodiments, the systems and methods of the present disclosure facilitate lysis of such occlusions.

Figure 44:
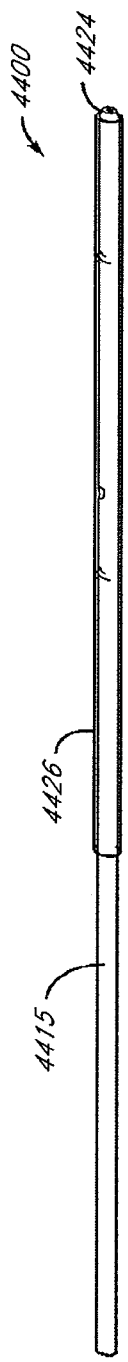
Figure 45:
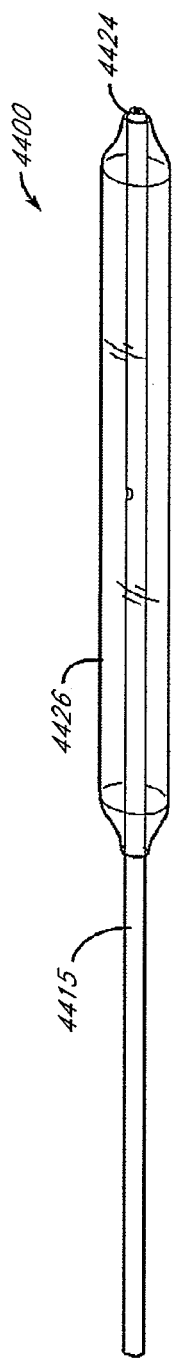
Figure 46:
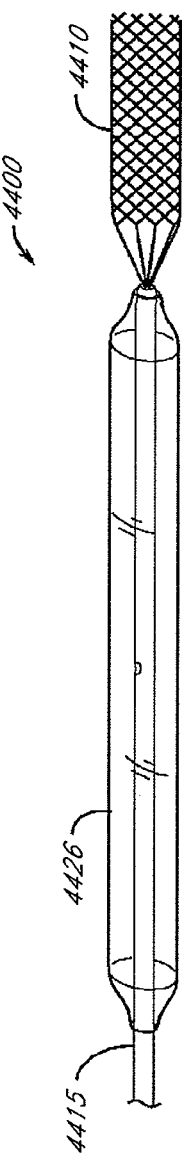

With reference to FIGS. 44-46, according to embodiments of the present disclosure, a balloon catheter and delivery system 4410 may include a catheter 4420 and a balloon 4426. The system 4410 may have a distal end 4424 and a proximal end 4422 (not shown).

Figure 47:
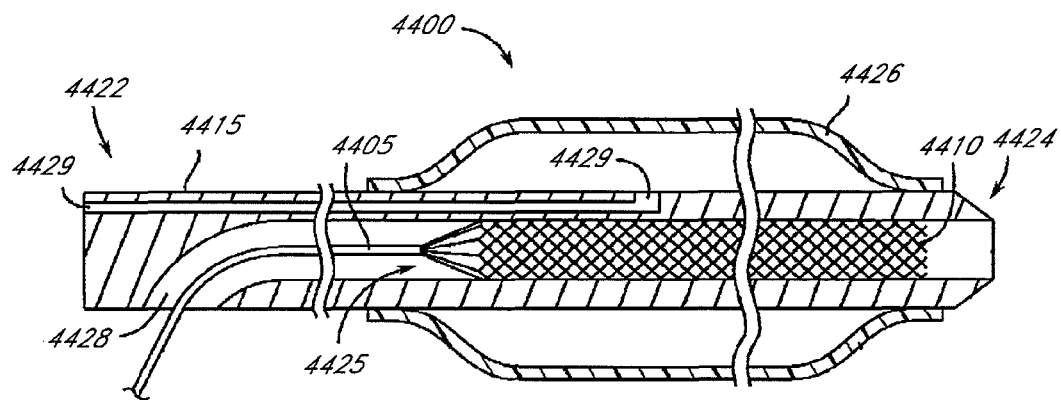

With reference to FIG. 47, according to embodiments of the present disclosure, a balloon catheter and delivery system 4410 may comprise a proximal end 4422, a distal end 4424 and at least one lumen. A catheter 4420 may be of any length for performance of minimally invasive vascular treatments. For example, for treatment of stroke, aneurysm, or other treatments within the brain of a patient, a catheter 4420 may have a length of between about 135 cm and about 150 cm.

The catheter 4410 may be of variable stiffness that is able to track to and through the tortuous anatomy or the cerebral vasculature (i.e., internal carotid artery, MCA, ACA, vertebral and basilar). The catheter 4410 may be one or two pieces and may have greater proximal pushability (stiffness) and greater distal flexibility (softness) to allow tracking to distal cerebral arteries.

According to embodiments, there may be provided at least one balloon 4426 near a distal end 4424 of a catheter 4420 for lumen dilatation, treatment of ICAD, vasospasm, flow arrest and remodeling of aneurysm necks during embolization coiling. According to embodiments, a balloon 4426 may be disposed outside the outer surface of catheter 4420, such that the catheter is concentrically disposed within a portion of balloon 4426, and such that balloon 4426 expands radially away from catheter 4420. The balloon 4426 may be a percutaneous transluminal angioplasty ("PTA") balloon. Such balloons are known in the art. According to embodiments, a plurality of balloons 4426 may be provided on an outer surface of catheter 4420. According to embodiments, a balloon 4426 may have a diameter in an inflated state of between about 0.010" and about 0.03".

A balloon 4426 may be comprised of materials such as Pebax, nylon, PTFE, polyethylene terephthalate ("PET"), polyurethane, polyester, an elastomeric material, or other suitable materials or mixtures thereof. A balloon 4426 may be of any length that facilitates adequate crossing of an occlusion. For example, a balloon 4426 may be between about 1.5 cm and about 4.0 cm in length.

According to embodiments, at least one inflation lumen 4429 may provide fluid communication to the balloon 4426 from the proximal end 4422 of the catheter 4420. An inflation lumen 4429 may provide a fluid to the inner portion of the balloon 4426, such that the fluid fills and inflates the balloon 4426. The inflation lumen 4429 may be open at or near proximal end 4422 of the catheter 4420, and may be configured to interface with a luer adaptor, fitting, handle, syringe, injector, plunger, or any other one or more selectable items for operation of the balloon catheter and delivery system by a user. Likewise, using ePTFE, FEP, PRFE, or other known and lubricious and/or drug eluting elements with the lumens 4428 and/or 4429 is contemplated.

According to embodiments, an expandable device 4430 may be configured to be disposable within the delivery lumen 4428. The expandable device 4430 may include a tether 38 and a cage-like structure 4436. Tether 4438 may be attached to the cage-like structure 4436 and may be selectively detachable. Tether 4438 may extend to or beyond the proximal end 4422 of catheter 4420. The expandable device 4430 may be disposable and trackable within the delivery lumen 4428 of the catheter 4420.

According to embodiments, at least a portion of a cage-like structure 4436 may be tapered at or near a point of attachment with a tether 4438. For example, a design may be provided tapering from the diameter of the tether 4438 to the largest diameter of the cage-like structure 4436. Likewise, alternate geometric configurations for this aspect of the instant teachings are contemplated to be within the scope of the present disclosure: everted, scalloped, and other variant ends, edges are prototyped and being used.

An example of an expandable device 4430 may be the IRIIS™ brand system for restoring blood flow in a thrombotic neurovascular occlusion in patients experiencing an ischemic stroke, by MindFrame®, Incorporated.

According to embodiments, a cage-like structure 4436 may be made of Nitinol to allow it to be compressed and loaded into an introducer for packaging. Similarly, "super-elastic" materials and memory-based materials likewise function, in accordance with the instant systems. According to embodiments, the cage-like structure 4436 may be compressible and expandable, such that it may maintain a compressed state when within a lumen and may maintain an expanded state when outside the lumen. According to embodiments, the cage-like structure 4436 may be "self-expanding", such that it expands once unsheathed from the delivery lumen 4428 of the catheter 4420.

According to embodiments, by attaching it to a delivery wire, the cage-like structure 4436 can be placed, retracted, repositioned and recaptured into a catheter. These features allow for the following: 1) perfusion of blood through artery during coiling; 2) perfusion from coiling herniation or prolapse; and 3) removal of the device, mitigating the use of Aspirin and Plavix.

According to embodiments, delivery lumen 4428 may have an inner diameter to accommodate the cage-like structure 4436. According to embodiments, at least one delivery lumen 4428 may provide a pathway through the catheter 4420 from about the proximal end 4422 of the catheter 4420 to about the distal end 4424 of the catheter 4420. A delivery lumen 4428 may be open at or near proximal end 4422 of the catheter 4420, and may be configured to interface with a luer adaptor, fitting, handle, syringe, injector, plunger, or any other one or more selectable items for operation of the balloon catheter and delivery system by a user. As discussed, PTFE, FEP, ePTFE and other lubricious and/or eluting elements are incorporated within at least the lumen 28.

According to embodiments, delivery lumen 4428 be lined with polytetrafluoroethylene ("PTFE") or a polymer thereof, alone or in combination with other materials, coatings, coverings, or delivery surfaces or substrates.

According to embodiments, the catheter 4420 and the expandable device 4430 may be configured to travel together, such that the expandable device 4430 may selectively accompany the catheter 4420 as the catheter 4420 travels through or is emplaced within a vasculature. For example, the catheter 4420 and the expandable device 4430 may be jointly delivered to a location while the cage-like structure 4436 remains within delivery lumen 4428.

According to embodiments, the catheter 4420 and the expandable device 4430 may be configured to be separately disposable, such that they may be moved relative to each other. For example, the expandable device 4430 may be advanced or retracted relative to the catheter 4420 by advancement or retraction of only the tether 4438 at the proximal end 4422 of the catheter 4420. Likewise, the catheter 4420 may be advanced or retracted relative to the expandable device 4430 by advancement or retraction of only the catheter 4420.

According to embodiments, catheter 4420 may be configured to provide tracking over a guide-wire (not shown). One or more lumens of catheter 4420 may provide a pathway for a guide-wire using an over-the-wire (OTW) system.

Figure 48:
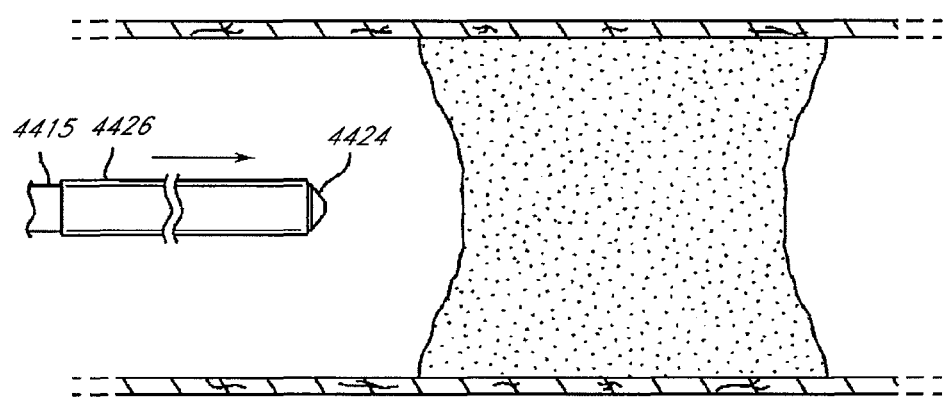

According to embodiments, a method is disclosed for treatment of a vascular occlusion, particularly a neurovascular occlusion. With reference to FIG. 48, according to embodiments of the present disclosure, a balloon catheter and delivery system 4410 may be provided to an occlusion.

Figure 49:
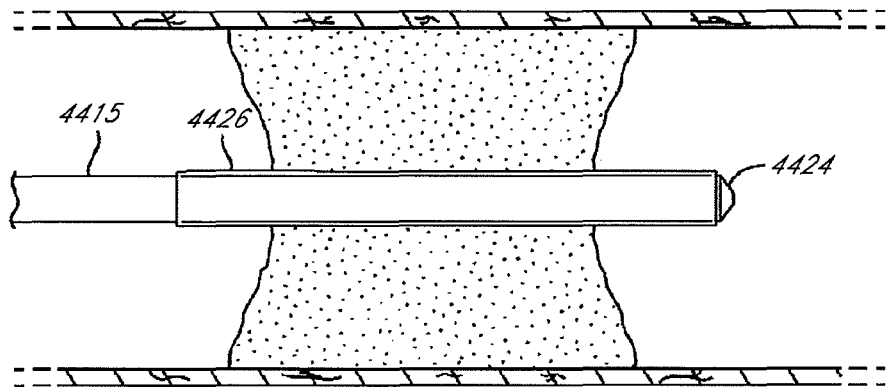

With reference to FIG. 49, according to embodiments of the present disclosure, a balloon catheter and delivery system 4410 may cross the occlusion by leading with distal end 4426 of catheter 4420. Crossing may be effectuated by pressure, force, ablation, or application of one of various types of energy at the distal end 4426 of the catheter 4420. Crossing may create an initial channel by displacement of the occlusion in the presence of the balloon catheter and delivery system 4410.

Figure 50:
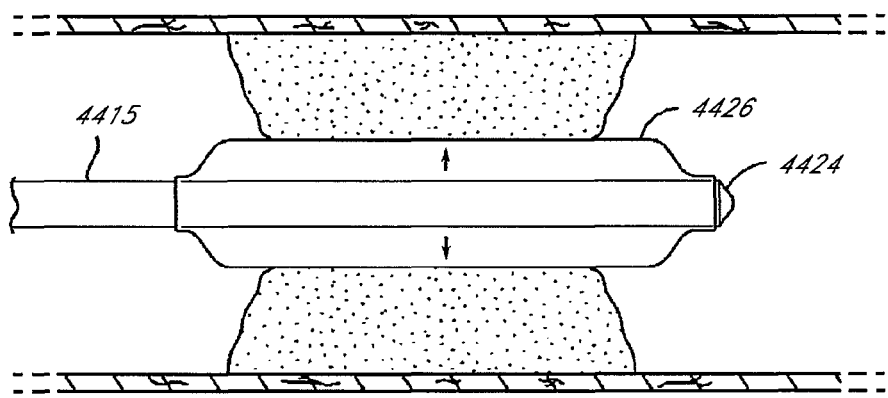

With reference to FIG. 50, according to embodiments of the present disclosure, a balloon 4426 may be inflated or a catheter 4420 may otherwise be dilated. Inflation of balloon 4426 may further displace or compress at least a portion of the occlusion away from the catheter 4420. Thereby, a broader channel may be created by balloon 4426, wherein the diameter or cross sectional area of the channel exceeds the diameter or cross sectional area of the catheter 4420.

Figure 51:
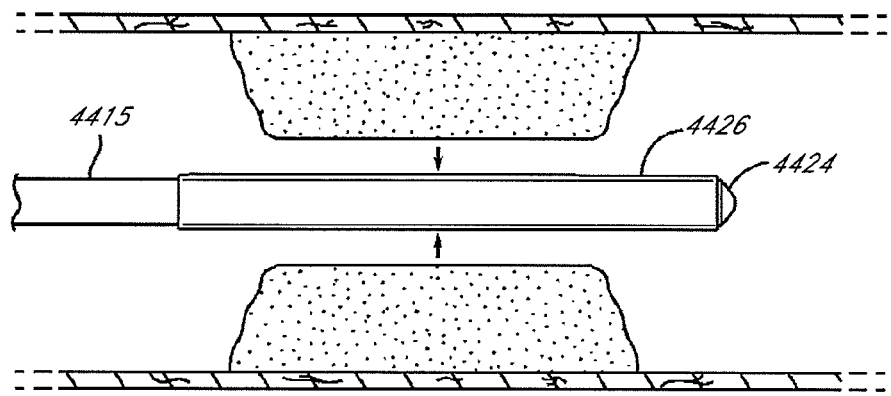

With reference to FIG. 51, according to embodiments of the present disclosure, the balloon 4426 may be deflated, whereby the broader channel exceeding the size of the catheter 4420 remains open at least temporarily.

Figure 52:
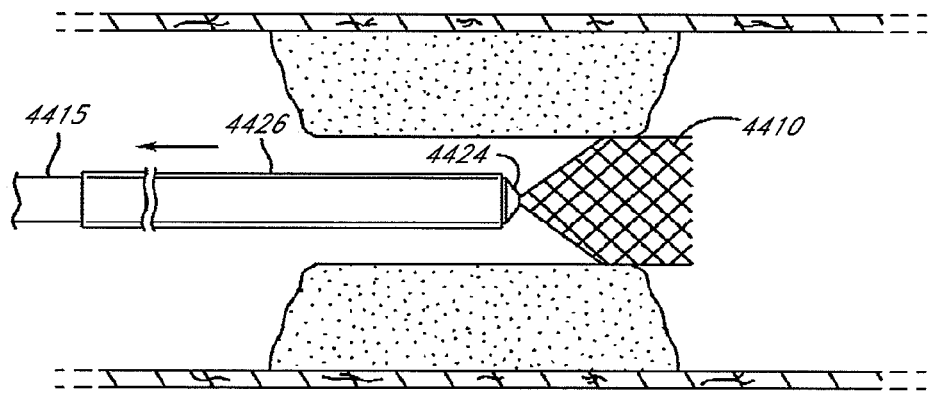

With reference to FIG. 52, according to embodiments of the present disclosure, the catheter 4420 may be withdrawn from an occlusion. The operation of withdrawing the catheter 4420 may simultaneously result in unsheathing and deployment of the cage-like structure 4436. Deployment of the cage-like structure 4436 may result in an expansion of any portion of the cage-like structure 4436 that is not within the lumen 4428 of the catheter 4420.

Figure 53:
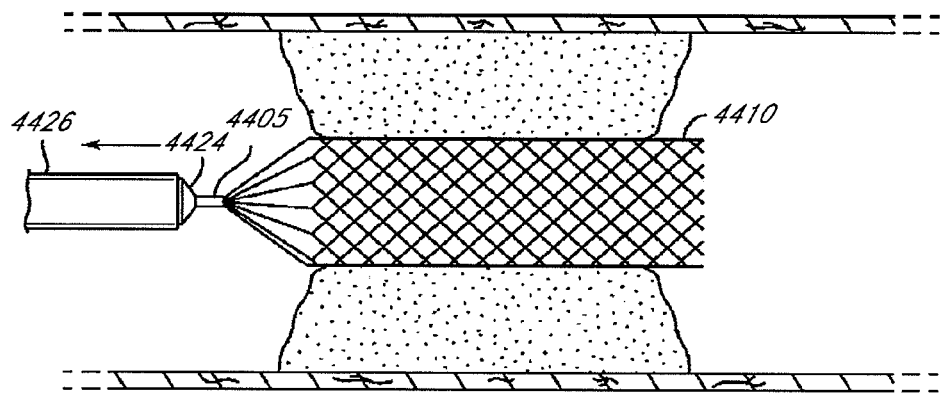

With reference to FIG. 53, according to embodiments of the present disclosure, the catheter 4420 may be withdrawn such that the cage-like structure 4436 may achieve a fully deployed state. For example, a fully deployed state may be achieved when the entire length of the cage-like structure 4436 is outside the delivery lumen 4428 of catheter 4420, or when at least a length of the cage-like structure 4436 corresponding to the length of the occlusion is outside the delivery lumen 4428 of catheter 4420. Expansion of the cage-like structure 4436 may maintain the approximate size and dimensions of the broader channel created by previously inflating balloon 4426.

Figure 54:
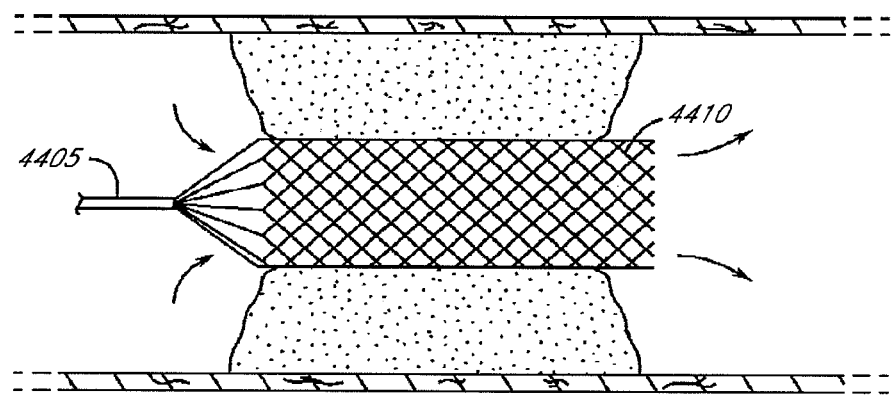

With reference to FIG. 54, according to embodiments of the present disclosure, the cage-like structure 4436 may achieve a temporary or long-term steady-state fully deployed state, wherein improved flow may be achieved through the occlusion. The flow through the channel may facilitate lysis of the occlusion and its constituent parts. The cage-like structure 4436 may maintain the channel created by the dilation or inflation of the balloon 4426, even as the channel deforms or is otherwise modified by the improved flow. According to embodiments, the cage-like structure 4436 may be maintained within the channel of the occlusion.

According to embodiments, the cage-like structure 4436 may be retracted into the delivery lumen 4428 of the catheter 4420, and the catheter 4420 may be removed from the location of the occlusion.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A blood-flow restoration system, comprising:
   a microcatheter having a lumen;
   an elongated member configured to be disposed within the lumen; and
   a self-expandable device coupled to a distal end of the elongated member, wherein the device comprises a tubular body formed from a plurality of cells that define an open-cell structure, the body having a proximal end, a distal end, and a middle section between the proximal and distal ends, wherein the device is configured to transition from a collapsed position to an expanded position when the device emerges from the lumen of the microcatheter, wherein the device comprises a mouth at the middle section of the body, the mouth being configured to accept passage of a clot into an interior of the body, the mouth being larger than any of the cells forming the open-cell structure, wherein the distal end of the body is closed in the expanded position, wherein the open-cell structure of the body comprises at least one free apex, and wherein at least a portion of the perimeter of the month is defined by the free apex.

2. The blood flow restoration system of claim 1, wherein the perimeter of the mouth is positioned at a radially outermost periphery of the body.

3. The blood flow restoration system of claim 1, wherein the middle section of the body is generally cylindrical.

4. The blood flow restoration system of claim 1, further comprising a guidewire configured to be disposed with the lumen of the microcatheter, wherein at least a portion of the guidewire is configured to be spaced apart from the body when the device is in the expanded position.

5. The blood flow restoration system of claim 1, wherein the device comprises a woven mesh.

6. The blood flow restoration system of claim 1, wherein the device is configured to compress the clot against an inner wall of the neurovasculature when the device is in the expanded configuration, thereby restoring blood flow through the neurovasculature downstream of the clot.

7. A blood-flow restoration system, comprising:
an elongated shaft having a lumen;
an elongated member configured to be disposed within the lumen of the elongated shaft; and
a self-expandable device coupled to a distal end of the elongated member, wherein the device comprises a tubular body having a plurality of cells that form an open-cell structure, wherein the body has a proximal portion, a distal portion, and an intermediate portion between the proximal and distal portions, wherein the device is configured to transition from a collapsed configuration to an expanded configuration when the device emerges from the lumen of the elongated shaft, wherein the device comprises an aperture formed at the intermediate portion of the body, the aperture being configured to accept passage of a clot into an interior of the body, wherein the aperture is larger than any of the cells forming the open-cell structure, wherein the open-cell structure of the body comprises at least one free apex, and wherein at least a portion of the perimeter of the aperture is defined by the free apex.

8. The blood flow restoration system of claim 7, wherein the perimeter of the aperture is positioned at a radially outermost periphery of the body.

9. The blood flow restoration system of claim 7, wherein the intermediate portion of the body is generally cylindrical.

10. The blood flow restoration system of claim 7, further comprising a guidewire configured to be disposed with the lumen of the elongated shaft, wherein at least a portion of the guidewire is configured to be spaced apart from the body when the device is in the expanded configuration.

11. The blood flow restoration system of claim 7, wherein the device is configured to compress the clot against an inner wall of the neurovasculature when the device is in the expanded configuration, thereby restoring blood flow through the neurovasculature downstream of the clot.

12. The blood flow restoration system of claim 7, wherein the distal portion of the body is tapered in the expanded configuration.

13. A blood-flow restoration system, comprising:
a microcatheter having a lumen;
an elongated member configured to be disposed within the lumen; and
a self-expandable device coupled to a distal end of the elongated member, wherein the device comprises a body having a proximal end, a distal end, and an intermediate portion between the proximal and distal ends, wherein the body defines an interior portion and an exterior portion, the interior and exterior portions being separated by a plurality of cells that form an open-cell structure, wherein the device is configured to transition from a collapsed configuration to an expanded configuration when the device emerges from the lumen of the microcatheter, wherein the device comprises a mouth at the intermediate portion of the body, the mouth being configured to accept passage of a clot from the exterior portion into the interior portion of the body, the mouth being larger than any of the cells forming the open-cell structure, wherein the distal end of the body is tapered in the expanded position, wherein the open-cell structure comprises at least one free apex, and wherein at least a portion of the perimeter of the mouth is defined by the free apex.

14. The blood flow restoration system of claim 13, wherein the perimeter of the mouth is positioned at a radially outermost periphery of the body.

15. The blood flow restoration system of claim 13, wherein the intermediate portion of the body is generally cylindrical.

16. The blood flow restoration system of claim 13, further comprising a guidewire configured to be disposed with the lumen of the microcatheter, wherein at least a portion of the guidewire is configured to be spaced apart from the body when the device is in the expanded configuration.

17. The blood flow restoration system of claim 13, wherein the device is configured to compress the clot against an inner wall of the neurovasculature when the device is in the expanded configuration, thereby restoring blood flow through the neurovasculature downstream of the clot.

* * * * *

UNITED STATES PATENT AND TRADEMARK OFFICE
CERTIFICATE OF CORRECTION

PATENT NO. : 11,337,714 B2
APPLICATION NO. : 16/561915
DATED : May 24, 2022
INVENTOR(S) : Ferrera et al.

It is certified that error appears in the above-identified patent and that said Letters Patent is hereby corrected as shown below:

On the Title Page

Item (56), in Column 2, under "Other Publications", Line 1, delete "Emolls" and insert -- Enrolls --, therefor.

Item (56), in Column 2, under "Other Publications", Line 6, delete "Emolls--" and insert -- Enrolls- --, therefor.

Item (57), in Column 2, under "Abstract", Line 9, delete "an cell" and insert -- a cell --, therefor.

In the Claims

In Column 34, in Claim 1, Line 59, delete "month" and insert -- mouth --, therefor.

Signed and Sealed this
Twenty-third Day of August, 2022

Katherine Kelly Vidal
*Director of the United States Patent and Trademark Office*